(12) United States Patent
Deschatelets et al.

(10) Patent No.: US 8,043,609 B2
(45) Date of Patent: *Oct. 25, 2011

(54) VIRAL COMPLEMENT CONTROL PROTEINS FOR EYE DISORDERS

(75) Inventors: Pascal Deschatelets, Lexington, KY (US); Paul Olson, Louisville, KY (US); Cedric Francois, Louisville, KY (US)

(73) Assignee: Potentia Pharmaceuticals, Inc., Louisville, KY (US)

( * ) Notice: Subject to any disclaimer, the term of this patent is extended or adjusted under 35 U.S.C. 154(b) by 426 days.

This patent is subject to a terminal disclaimer.

(21) Appl. No.: 11/612,751

(22) Filed: Dec. 19, 2006

(65) Prior Publication Data

US 2008/0075755 A1 Mar. 27, 2008

Related U.S. Application Data

(63) Continuation-in-part of application No. 11/247,886, filed on Oct. 8, 2005.

(60) Provisional application No. 60/616,983, filed on Oct. 8, 2004, provisional application No. 60/751,771, filed on Dec. 19, 2005, provisional application No. 60/760,974, filed on Jan. 19, 2006.

(51) Int. Cl.
*A61K 35/00* (2006.01)
*C07K 5/00* (2006.01)

(52) U.S. Cl. .................. 424/93.1; 424/85.1; 530/300

(58) Field of Classification Search .................. 424/93.1
See application file for complete search history.

(56) References Cited

U.S. PATENT DOCUMENTS

| | | | |
|---|---|---|---|
| 5,157,110 A | 10/1992 | Kotwal et al. | |
| 5,492,135 A | 2/1996 | Devore et al. | |
| 5,861,486 A | 1/1999 | Devore et al. | |
| 6,129,761 A | 10/2000 | Hubbell | |
| 6,140,472 A | 10/2000 | Rosengard et al. | |
| 6,197,934 B1 | 3/2001 | Devore et al. | |
| 6,204,365 B1 | 3/2001 | Devore et al. | |
| 6,331,313 B1 | 12/2001 | Wong et al. | |
| 6,551,595 B1 | 4/2003 | Rosengard et al. | |
| 6,692,759 B1 | 2/2004 | Wong et al. | |
| 6,897,290 B1 | 5/2005 | Atkinson et al. | |
| 7,084,106 B1 * | 8/2006 | Kotwal et al. | 514/2 |
| 7,108,986 B2 | 9/2006 | Korc et al. | |
| 2002/0102581 A1 | 8/2002 | Hageman et al. | |
| 2003/0017501 A1 | 1/2003 | Hageman et al. | |
| 2003/0207309 A1 | 11/2003 | Hageman et al. | |
| 2006/0263819 A1 | 11/2006 | Hageman et al. | |
| 2007/0238654 A1 | 10/2007 | Deschatelets et al. | |
| 2008/0075755 A1 | 3/2008 | Deschatelets et al. | |

FOREIGN PATENT DOCUMENTS

| | | |
|---|---|---|
| EP | 0422681 A1 | 4/1991 |
| WO | WO 00/47130 A1 | 8/2000 |
| WO | WO 00/71147 A1 | 11/2000 |
| WO | WO 01/84149 A1 | 11/2001 |
| WO | WO 2004/028635 A1 | 4/2004 |
| WO | WO 2005/023296 A1 | 3/2005 |
| WO | WO 2007/084765 A1 | 7/2007 |

OTHER PUBLICATIONS

Song et al. Molecular Biology of the Cell, 2004, vol. 15, pp. 1287-1296.*
Acosta, J. et al. "Complement and complement regulatory proteins as potential molecular targets for vascular diseases," Curr Pharm Des. (2004) 10(2):203-11, Bentham Science Publishers Ltd., Bussum, the Netherlands.
Acosta, J. et al. "Molecular basis for a link between complement and the vascular complications of diabetes," Proc Nat Acad Sci. (2000) 97 (10): 5450, National Academies of Science, Washington, DC.
Albrecht, J-C. & Fleckenstein, B. "New member of the multigene family of complement control proteins in *Herpesvirus saimiri*," J. Virol. (1992) 66: 3937-3940, American Society for Microbiology, Washington, DC.
Albrecht, J. et al. "*Herpesvirus saimiri* has a gene specifying a homologue of the cellular membrane glycoprotein CD59," Virology. (1992) 190: 527-530, Academic Press, London, UK.
Ambati, J. et al. "Age-related macular degeneration: Etiology, pathogenesis, and therapeutic strategies," Surv. Opthalmol. (2003) 48 (3): 257-293, Elsevier Inc., Amsterdam, The Netherlands.
Bora, P. S. et al. "Role of complement and complement membrane attack complex in laser-induced choroidal neovascularization," Journal of Immunology (2005) 174(1): 491-497, American Association of Immunologists, Inc., Bethesda, MD.
Francois, C. et al. "Compositions and methods for treatment of macular degeneration and related conditions," U.S. Appl. No. 11/375,587, filed Mar. 13, 2006. (Not yet published.).
Gerl, V. et al. "Extensive Deposits of Complement C3d and C5b-9 in the Choriocapillaris of Eyes of Patients with Diabetic Retinopathy," Investigative Ophthalmology and Visual Science (2002) 43 (4): 1104-1108, Association for Research in Vision and Opthalmology, Rockville, MD.

(Continued)

*Primary Examiner* — Bao Li
(74) *Attorney, Agent, or Firm* — Choate, Hall & Stewart LLP

(57) ABSTRACT

The present invention provides compositions and methods for treating and/or preventing age related macular degeneration and other conditions involving macular degeneration or choroidal neovascularization, ocular inflammation, or any combination of these. Certain of the compositions comprise a poxvirus complement control protein or a complement binding fragment or variant thereof. Other compositions comprise a poxvirus complement control protein linked to a moiety that binds to a component present on or at the surface of cell or noncellular molecular entity, e.g., a component present in the eye of a subject at risk of or suffering from age related macular degeneration or a related condition or choroidal neovascularization, ocular inflammation, or any combination of these. Certain of the methods comprise administering a poxvirus complement control protein or complement binding fragment or variant thereof to a subject.

14 Claims, 8 Drawing Sheets

(1 of 8 Drawing Sheet(s) Filed in Color)

OTHER PUBLICATIONS

Herold, et al. "Glycoprotein C of herpes simplex virus type 1 plays a principal role in the adsorption of virus to cells and in infectivity," J. Virol. (1991) 65: 1090-1098, American Society of Microbiology, Washington, DC.

International Preliminary Report on Patentability for PCT/US2005/036547 (Apr. 11, 2007).

International Search Report for PCT/US2005/036547 (Oct. 6, 2006).

Jaffe, G. "Safety and pharmacokinetics of an intraocular fluocinolone acetonide sustained delivery device," Invest. Ophthalmol. Vis. Sci. (2000) 41(11): 3569-75, Association for Research in Vision and Opthalmology, Rockville, MD.

Johnson, L et al. "Complement activation and inflammatory processes in drusen formation and age-related macular degeneration," Experimental Eye Research (2001) 73 (6):887-896, Academic Press, London, United Kingdom.

Kotwal, G. "Poxviral mimicry of complement and chemokine system components: what's the end game?" Immunol. Today (2000) 21(5), 242-248, Elsevier Science Publishers Ltd., London, United Kingdom.

Kotwal, G. et al. "Vaccinia virus encodes a secretory polypeptide structurally related to complement control proteins," Nature (1988) 335: 176-178, Nature Publishing Group, London, United Kingdom.

Makrides, S. "Therapeutic inhibition of the complement system," Pharm Rev., (1998) 50(1): 59-87, The American Society for Pharmacology and Experimental Therapeutics, Bethesda, MD.

Mettenleiter et al. "Interaction of glycoprotein gIII with a cellular heparinlike substance mediates adsorption of pseudorabies virus," J. Virol (1990) 64: 278-286, American Society for Microbiology, Washington, DC.

Reid, K. and Day, A. , "Structure-function relationships of the complement components," Immunol. Today (1989) 10:177-80, Elsevier Science Publishers Ltd., London, United Kingdom.

Rosengard, A. et al. "Variola virus immune evasion design: expression of a highly efficient inhibitor of human complement," Proc. Natl. Acad. Sci. (2002) 99(13): 8803-8813, National Academy of Sciences, Washington, DC.

Schreuers et al. "Glycoprotein gIII of pseudorabies virus is multifunctional," J. Virol. (1988) 62: 2251-2257, American Society for Microbiology, Washington, DC.

Smith, S. et al. "Conserved surface-exposed K/R-X-K/R motifs and net positive charge on poxvirus complement control proteins serve as putative heparin binding sites and contribute to inhibition of molecular interactions with human endothelial cells: a novel mechanism for evasion of host defense," J. Virol. (2000) 74(12), 5659-5666, American Society for Microbiology, Washington, DC.

Written Opinion for PCT/US2005/036547 (Oct. 6, 2006).

Yamane, K. et al. "Proteome analysis of human vitreous proteins." Mol Cell Proteomics (2003) 2(11):1177-87, American Society for Biochemistry and Molecular Biology, Inc., Bethesda, MD.

Yannuzzi L. et al. "Retinal angiomatous proliferation in age-related macular degeneration," Retina (2001) 21 (5):416-34, Lippincott Williams & Wilkins, Hagerstown, MD.

Zhang, J. et al. "Early Complement Activation and Decreased Levels of Glycosylphosphatidylinositol-Anchored Complement Inhibitors in Human and Experimental Diabetic Retinopathy," Diabetes (2002) 51 (12): 3499-3504, American Diabetes Association, Washington DC.

Liszewski, K.M. et al., "Structure and Regulatory Profile of the Monkeypox Inhibitor of Complement: Comparison to Homologs in Vaccinia and Variola and Evidence for Dimer Formation," J. Immunol. (2006) 176:3725-3734.

* cited by examiner

Figure 3A

Vaccinia virus complement control protein precursor: Accession number P10998

```
mkvesvtflt llgigcvlsc ctipsrpinm kfknsvetda nanynigdti eylclpgyrk
qkmgpiyakc tgtgwtlfnq cikrrcpspr didngqldig gvdfgssity scnsgyhlig
esksycelgs tgsmvwnpea picesvkcqs ppsisngrhn gyedfytdgs vvtyscnsgy
slignsgvlc sggewsdppt cqivkcphpt isngylssgf krsysyndnv dfkckygykl
sgsssstcsp gntwkpelpk cvr (SEQ ID NO: 1)
```

Figure 3B

Vaccinia virus complement control protein: Accession number 1RID_B

```
cctipsrpin mkfknsvetd ananynigdt ieylclpgyr kqkmgpiyak ctgtgwtlfn
qcikrrcpsp rdidngqldi ggvdfgssit yscnsgyhli gesksycelg stgsmvwnpe
apicesvkcq sppsisngrh ngyedfytdg svvtyscnsg yslignsgvl csggewsdpp
tcqivkcphp tisngylssg fkrsysyndn vdfkckygyk lsgsssstcs pgntwkpelp
kcvr (SEQ ID NO: 2)
```

```
VAC-COP C3L    CCTIPSRFDNMEFENSVEEDANARYNIGDTIEYLCLPGYREQRMGFIYAKCTGDGRTLESQCI
VAC-WR  C21L   ............................................................
CPV-GRI C17L   ..P......T....GP.---.-SH....................................
CPV-BRI IMP    ...............G............................................
VAR-BSH D15L   ............................................................
VAR-IND D12L   .......T....................................................
VAR-GAR E18L   ............................................................
MPV-ZAI D15L   Y...........-...............................................

VAC-COP C3L    IRECPSFRDIDNGQLDIGEVDFGESITTSCNSGYRLIGESESICELGSTGSMVWNPEAPICE
VAC-WR  C21L   ............................................................
CPV-GRI C17L   .............I....E......Q.............Y...................
CPV-BRI IMP    ..K..........I....E......Q.............Y.........K.........
VAR-BSH D15L   .............H...........T....Y...K................K.......
VAR-IND D12L   .............H...........T....Y...K................K.......
VAR-GAR E18L   .............H...........T....Y...K................K.......
MPV-ZAI D15L   ............................................................

VAC-COP C3L    SVKCQSPPSISNGRHNGIEDFTZDGSVYTSCNSGYSLIGNSGVLCSGEEKNDPPTCQ
VAC-WR  C21L   .........................................................
CPV-GRI C17L   .........................................................
CPV-BRI IMP    ....P....VT..........................IV.................
VAR-BSH D15L   .....L........N.......................N.................
VAR-IND D12L   .....L........N.......................N.................
VAR-GAR E18L   .....L........N.......................N.................
MPV-ZAI D15L   ..................I...I...............M...N.............

VAC-COP C3L    IVKCPHPTISNGYLSSGFRSYSTNDNVDFRCKYGYKLSGSSSSTCSPGNTHRPELFECVR  SEQ ID NO:3
VAC-WR  C21L   ...........................................................Q........  SEQ ID NO:4
CPV-GRI C17L   ...........................................................Q........  SEQ ID NO:5
CPV-BRI IMP    ....S.T......H.....EH......................................Q........  SEQ ID NO:6
VAR-BSH D15L   .....L...............T.....................................Q........  SEQ ID NO:7
VAR-IND D12L   .....L...............T.....................................Q........  SEQ ID NO:8
VAR-GAR E18L   ....Y.L...............T....................................Q........  SEQ ID NO:9
MPV-ZAI D15L   ........-....K.LAA...................................................  SEQ ID NO:10
```

Figure 4

| | | Inhibition of Hemolysis | Heparin Binding Activity | K+R | % K+R | pI | # of Putative Sites (K/R X K/R) |
|---|---|---|---|---|---|---|---|
| VCP/IMP/SPICE | | + | + | 23 | 9.43 | 8.80 | 4 |
| MPV Homolog of VCP | | + | N/D | 16 | 8.00 | 7.22 | 3 |
| rVCP | | + | + | 23 | 9.43 | 8.80 | 4 |
| rVCP SCR (2,3,4) | | − | + | 16 | 8.79 | 7.22 | 2 |
| rVCP SCR (1,2) | | − | + | 12 | 9.60 | 7.00 | 3 |
| rVCP SCR (2,3) | | − | − | 7 | 5.83 | 4.41 | 1 |
| rVCP SCR (3,4) | | − | + | 11 | 9.24 | 9.08 | 1 |

MKVERVTFLTLLGIGCVLSCCTIPSRPINMKFKNSVETDANANYNIGDTIEYLCL
PGYRKQKMGPIYAKCTGTGWTLFNQCIKRRCPSPRDIDNGHLDIGGVDFGSSIT
YSCNSGYYLIGEYKSYCKLGSTGSMVWNPKAPICESVKCQLPPSISNGRHNGY
NDFYTDGSVVTYSCNSGYSLIGNSGVLCSGGEWSNPPTCQIVKCPHPTILNGYL
SSGFKRSYSYNDNVDFTCKYGYKLSGSSSSTCSPGNTWQPELPKCVR (SEQ ID NO: 12)

Confocal micrographs of CNV (stained green) in the eyes of mice without (A) and with (B) injection of VCP (30 µg).

VIRAL COMPLEMENT CONTROL PROTEINS FOR EYE DISORDERS

CROSS-REFERENCE TO RELATED APPLICATIONS

This application is a continuation-in-part of U.S. Ser. No. 11/247,886, filed Oct. 8, 2005, which claims priority to and the benefit of provisional application U.S. Ser. No. 60/616,983 filed Oct. 8, 2004, each of which is incorporated herein by reference. This application claims priority to and the benefit of provisional applications U.S. Ser. No. 60/751,771, filed Dec. 19, 2005, and U.S. Ser. No. 60/760,974, filed Jan. 19, 2006, each of which is incorporated herein by reference.

BACKGROUND OF THE INVENTION

The macula is a small area in the retina of the eye, approximately 3 to 5 millimeters in size, adjacent to the optic nerve. It is the most sensitive area of the retina and contains the fovea, a depressed region that allows for high visual acuity and contains a dense concentration of cones, the photoreceptors that are responsible for color vision.

Macular degeneration is a term that refers to a number of different diseases characterized by degenerative changes in the macula, all of which lead to a loss of central vision. Age-related macular degeneration (ARMD) is the most common cause of functional blindness in developed countries for those over 50 years of age (Seddon, J M. Epidemiology of age-related macular degeneration. In: Ogden, T E, et al., eds. Ryan S J, ed-in-chief. *Retina* Vol II. 3rd ed. St. Louis, Mo.: Mosby; 2001:1039-50). The disease is characterized by progressive degeneration of the retina, retinal pigment epithelium (RPE), and underlying choroid (the highly vascular tissue that lies beneath the RPE, between the retina and the sclera). The retinal pigment epithelial layer is believed to be crucial for photoreceptor health. Cells in this layer recycle visual pigment (rhodopsin), phagocytose photoreceptor tips daily as part of rod and cone regeneration, and transport fluid across the membrane to the choroid, which is believed to help prevent detachment of the neural retina. Central vision deteriorates when cells in the RPE cease to function properly, which can lead to photoreceptor degeneration.

Despite extensive investigation, the pathogenesis of ARMD remains unclear, and the etiology of the molecular events that occur is not well understood. A variety of factors including oxidative stress, inflammation with a possible autoimmune component, genetic background (e.g., mutations), and environmental or behavioral features such as smoking and diet may contribute to the pathogenesis of ARMD in ways that are as yet poorly understood. Regardless of the underlying etiology, a clinical hallmark of ARMD is the appearance of drusen, localized deposits of lipoproteinaceous material that accumulate in the space between the RPE and Bruch's membrane, which separates the RPE from the choroidal vessels (choriocapillaris). Drusen are typically the earliest clinical finding in ARMD, and the existence, location, and number of drusen are used in classifying the disease into stages and for monitoring its progression (Ambati, J., et al., *Surv. Opthalmol.*, 48(3): 257-293, 2003; "Preferred Practice Pattern: Age-Related Macular Degeneration", American Academy of Ophthalmology, 2003). Drusen are typically the earliest clinical finding in ARMD.

ARMD has been classified into both "dry" and "wet" (exudative, or neovascular) forms. Dry ARMD is much more common than wet ARMD, but the dry form can progress to the wet form, and the two occur simultaneously in a significant number of cases. Dry ARMD is typically characterized by progressive apoptosis of cells in the RPE layer, overlying photoreceptor cells, and frequently also the underlying cells in the choroidal capillary layer. Confluent areas (typically at least 175 μm in minimum diameter) of RPE cell death accompanied by overlying photoreceptor atrophy are referred to as geographic atrophy. Patients with this form of ARMD experience a slow and progressive deterioration in central vision.

Wet ARMD is characterized by bleeding and/or leakage of fluid from abnormal vessels that have grown from the choroidal vessels (choriocapillaris) beneath the RPE and the macula, which can be responsible for sudden and disabling loss of vision. It has been estimated that much of the vision loss that patients experience is due to such choroidal neovascularization (CNV) and its secondary complications. A subtype of neovascular ARMD in which angiomatous proliferation originates from the retina and extends posteriorly into the subretinal space, eventually communicating in some cases with choroidal new vessels has been identified (Yannuzzi, L. A., et al., *Retina*, 21(5):416-34, 2001). This form of neovascular ARMD, termed retinal angiomatous proliferation (RAP) can be particularly severe. The existence of macular drusen is a strong risk factor for the development of both wet and dry forms of ARMD (Ambati, J., et al., supra).

Treatment options for ARMD are limited, and none are fully effective (Ambati, J., et al., *Surv. Opthalmol.*, 48(3): 257-293, 2003, and references therein). Thus there is a need in the art for new approaches to the treatment of ARMD and also of other diseases and conditions of the eye characterized by macular degeneration, choroidal neovascularization, retinal neovascularization, retinal angiomatous proliferation, and/or blood vessel leakage. Such diseases and conditions include, but are not limited to, diabetic retinopathy and retinopathy of prematurity.

There is also a need in the art for new approaches to the treatment of eye disorders characterized by ocular inflammation. Such disorders may or may not be characterized also by macular degeneration, choroidal neovascularization, retinal neovascularization, retinal angiomatous proliferation, and/or blood vessel leakage.

SUMMARY OF THE INVENTION

The present invention addresses the foregoing needs, among others. The invention provides a method of treating an eye disorder characterized by macular degeneration, choroidal neovascularization, retinal neovascularization, ocular inflammation, or any combination of these, comprising (i) providing a subject in need of treatment for the eye disorder; and (ii) administering a composition comprising a viral complement control protein (VCCP) or a complement inhibiting fragment or variant thereof to the subject.

The invention further provides a method of treating an eye disorder characterized by macular degeneration, choroidal neovascularization, retinal neovascularization, ocular inflammation, or any combination of these, comprising (i) providing a subject in need of treatment for the eye disorder; and (ii) administering a composition comprising a viral complement interfering protein (VCIP) or a complement inhibiting fragment or variant thereof to the subject.

The invention further provides a composition comprising: (i) a VCCP or a complement inhibiting fragment or variant thereof, and (ii) a moiety that binds to a component present in the eye of a subject at risk of or suffering from an eye disorder characterized by macular degeneration, choroidal neovascularization, retinal neovascularization, ocular inflammation, or any combination of these. The invention further provides a composition comprising: (i) a VCIP or a complement inhibiting fragment or variant thereof, and (ii) a moiety that binds to a component present in the eye of a subject at risk of or suffering from an eye disorder characterized by macular degeneration, choroidal neovascularization, retinal neovascularization, ocular inflammation, or any combination of these. In the foregoing compositions, the component can be a cellular marker or a noncellular entity, e.g., a molecule or complex that is present in deposits found in the eye of a subject with macular degeneration.

The invention further provides a composition comprising: (i) a VCCP or a complement inhibiting fragment or variant thereof, and (ii) an angiogenesis inhibitor. The invention further provides a composition comprising: (i) a VCIP or a complement inhibiting fragment or variant thereof; and (ii) an angiogenesis inhibitor.

The invention further provides a composition comprising: (i) a VCCP or a complement inhibiting fragment or variant thereof, and (ii) a soluble gel-forming material. The composition forms a gel following introduction into the body, e.g., upon contact with a physiological fluid. The invention further provides a composition comprising: (i) a VCIP or a complement inhibiting fragment or variant thereof, and (ii) a soluble gel-forming material. The composition forms a gel following introduction into the body, e.g., upon contact with a physiological fluid. In certain embodiments of the invention any of the compositions comprising a soluble gel-forming material further comprises an angiogenesis inhibitor. The composition may be formed into a gel implant in vitro and administered to or in the vicinity of the eye.

The invention further provides ocular and periocular implants and polymeric delivery vehicles comprising (i) a VCCP or a complement inhibiting fragment or variant thereof or (ii) a VCIP or a complement inhibiting fragment or variant thereof. In some embodiments of the invention the composition further comprises a moiety that binds to a component present in the eye of a subject at risk of or suffering from an eye disorder characterized by macular degeneration, choroidal neovascularization, retinal neovascularization, ocular inflammation, or any combination of these. In certain embodiments of the invention either of the foregoing compositions further comprises an angiogenesis inhibitor.

The invention further provides multimeric complexes comprising two or more different VCCPs or VCIPs. The invention further provides a supramolecular complex comprising at least one VCCP or VCIP.

The invention further provides methods of treating an eye disorder characterized by macular degeneration, choroidal neovascularization, retinal neovascularization, ocular inflammation, or any combination of these, comprising administering any of the inventive compositions to a subject at risk of or suffering from the eye disorder. The compositions can be administered as sole therapy or one or more other treatments for the disorder may also be administered either concurrently or sequentially. Such treatments include, but are not limited to, laser photocoagulation, photodynamic therapy (e.g., Visudyne®), or anti-angiogenic therapy.

Methods for testing the inventive compositions and methods are also provided.

Methods for making the inventive compositions are also provided.

In any of the embodiments of the present invention, the eye disorder can be a macular degeneration related condition, diabetic retinopathy, retinopathy of prematurity, or any condition featuring choroidal, retinal neovascularization, and/or ocular inflammation.

Included among the eye disorders that can be treated with the compositions and methods of the invention are eye disorders in which retinal angiomatous proliferation (RAP) is present. RAP involves abnormal proliferation of retinal blood vessels (retinal neovascularization) and is a feature of a subtype of neovascular ARMD, but the compositions and methods of the invention can be used to treat RAP due to any cause, whether or not associated with macular degeneration. The invention therefore provides a method of inhibiting an eye disorder characterized by retinal angiomatous proliferation comprising (i) providing a subject in need of treatment for the eye disorder; and (ii) administering a composition comprising a VCCP, a VCIP, or a complement inhibiting fragment or variant of either, to the subject. The composition can be administered using any of the methods described herein. In some embodiments the composition is delivered in close proximity to the posterior segment of the eye.

In any of the embodiments of the invention the VCCP can be a poxvirus VCCP (PVCCP) or a herpesvirus VCCP (HVCCP). In any of the embodiments of the invention, the PVCCP can be from vaccinia virus, variola virus, monkeypox virus, cowpox virus, etc. In any of the embodiments of the invention involving a fragment or variant of a VCCP, the fragment or variant may be at least 80% identical to the VCCP, at least 85% identical to the VCCP, at least 90% identical to the VCCP, or at least 95% identical to the VCCP, provided that the fragment or variant inhibits complement. In any of the embodiments of the invention involving a fragment or variant of a VCIP, the fragment or variant may be at least at least 80% identical to the VCIP, at least 85% identical to the VCIP, at least 90% identical to the VCIP, or at least 95% identical to the VCIP, provided that the fragment or variant inhibits complement.

Any of the compositions may comprise compstatin and/or an analog or derivative thereof. The methods of the invention may comprise administering compstatin or an analog or derivative thereof to a subject suffering from or at risk of an eye disorder characterized by macular degeneration, choroidal neovascularization, retinal neovascularization, ocular inflammation, or any combination of these. Compstatin or an analog or derivative thereof may be administered in a composition together with a VCCP, VCIP, or a fragment or variant of either. Alternately, compstatin or an analog or derivative thereof may be administered separately. Any of the delivery methods described herein may be employed. Compstatin and compstatin analogs, derivatives, etc., and their use for ocular disorders such as those described herein are further described in U.S. Ser. No. 60/726,447, filed Oct. 12, 2005, entitled "Compstatin and Analogs Thereof for Eye Disorders". See also U.S. Pat. No. 6,319,897 and WO2004/026328 (PCT/US2003/029653).

In any of the embodiments of the invention that features an angiogenesis inhibitor, the angiogenesis inhibitor may be any angiogenesis inhibitor known in the art. For example, the angiogenesis inhibitor may, but need not be, selected from the group consisting of: Macugen® or another VEGF nucleic acid ligand; Lucentis®, Avastin®), or another anti-VEGF antibody; combretastatin or a derivative or prodrug thereof such as Combretastatin A4 Prodrug (CA4P); VEGF-Trap; EVIZON™ (squalamine lactate); AG-013958 (Pfizer, Inc.); JSM6427 (Jerini A G), β2-glycoprotein 1 (β2-GP1), and a short interfering RNA (siRNA) that inhibits expression of one or more VEGF isoforms (e.g., $VEGF_{165}$) or inhibits expression of a VEGF receptor (e.g., VEGFR1).

Unless otherwise stated, the invention makes use of standard methods of molecular biology, cell culture, animal maintenance, ophthalmologic examination, and administration of therapeutic agents to subjects, etc., and uses art-accepted meanings of terms. This application refers to various patents and publications. The contents of all scientific articles, books, patents, and other publications, mentioned in this application are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; *Kuby Immunology*, 4$^{th}$ ed., Goldsby, R. A., Kindt, T. J., and Osborne, B. (eds.), W.H. Freeman, 2000, *Goodman and Gilman's The Pharmacological Basis of Therapeutics*, 10$^{th}$ Ed. McGraw Hill, 2001, Katzung, B. (ed.) *Basic and Clinical Pharmacology*, McGraw-Hill/Appleton & Lange; 9th edition (December 2003), *Ophthalmic Surgery: Principles and Practice*, 3$^{rd}$ ed., W.B. Saunders Company, 2002; Albert, D M and Lucarelli, M J (eds.), *Clinical Atlas of Procedures in Ophthalmic Surgery*, American Medical Association, 2003. In the event of a conflict or inconsistency between any of the incorporated references and the instant specification, the specification shall control, it being understood that the determination of whether a conflict or inconsistency exists is within the discretion of the inventors and can be made at any time.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1C depicts a normal eye. FIG. 1D depicts an eye suffering from dry ARMD. FIG. 1E depicts an eye suffering from exudative ARMD. ONL=outer nuclear layer; IS=inner segment; OS=outer segment; RPE=retinal pigment epithelial layer; BM=Bruch's membrane; CC=choriocapillaris. From Tezel, T., et al., *Trends in Molecular Medicine*, 10(9), 417-420, 2004.

FIGS. 3A and 3B show sequences of vaccinia virus complement control protein precursor (SEQ ID NO: 1) and the mature vaccinia virus complement control protein (SEQ ID NO: 2).

FIG. 4 shows a sequence comparison of mature complement control proteins from a variety of orthopoxvirus isolates (SEQ ID NO: 3-10). The corresponding genetic loci are as follows: SEQ ID NO: 3 is VAC-COP C3L, SEQ ID NO: 4 is VAC-WR C21L, SEQ ID NO: 5 is CPV-GRI C17L, SEQ ID NO: 6 is CPV-BRI IMP, SEQ ID NO: 7 is VAR-BSH D15L, SEQ ID NO: 8 is VAR-IND D12L, SEQ ID NO: 9 is VAR-GAR B18L, SEQ ID NO: 10 is MPV-ZAI D15L. Modified from Smith, S A, et al., *J. Virol.* 74(12), 5659-5666, 2000.

FIG. 5 shows a comparison of the SCR domain structure of a number of complement control proteins and fragments thereof, the number of K+R residues, % K+R residues, pI, number of putative heparin binding sites, and ability to inhibit hemolysis and/or bind to heparin. Modified from Smith, S A, et al., *J. Virol.* 74(12), 5659-5666, 2000. The domains are SCR modules. Thus, for example, rVCP SCR (2, 3, 4), is a recombinantly produced polypeptide containing SCRs 2, 3, and 4 from VCP.

FIG. 6 shows the amino acid sequence of SPICE (SEQ ID NO: 12).

DEFINITIONS

Figure 1A:
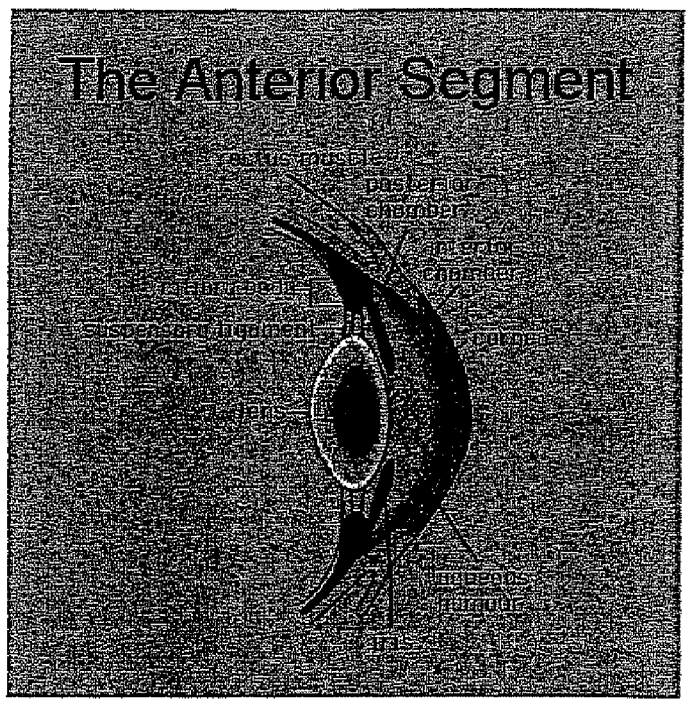
FIGS. 1A-1E show schematic representations of the anterior and posterior segments of the eye (1A and 1B) and the outer layers of the eye (1C-1E).

"Angiogenesis" or "angiogenic" refer to formation, growth, and/or development of new blood vessels.

The terms "angiogenesis inhibitor" and "antiangiogenic agent" are used interchangeably herein to refer to agents that are capable of inhibiting or reducing one or more processes associated with angiogenesis including, but not limited to, endothelial cell proliferation, endothelial cell migration, and capillary tube formation.

The terms "approximately" or "about" in reference to a number are generally include numbers that fall within a range of 5% in either direction (greater than or less than) of the number unless otherwise stated or otherwise evident from the context (except where such number would exceed 100% of a possible value).

"Biocompatible" refers to a material that is substantially non-toxic to cells in vitro, e.g., if its addition to cells in culture results in less than or equal to 20% cell death. A material is considered biocompatible with respect to a recipient if it is substantially nontoxic to the recipient's cells in the quantities and at the location used, and also does not elicit or cause a significant deleterious or untoward effect on the recipient's body, e.g., an immunological or inflammatory reaction, unacceptable scar tissue formation, etc.

"Biodegradable" means that a material is capable of being broken down physically and/or chemically within cells or within the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of. Preferably a biodegradable compound is biocompatible.

A "biological macromolecule" is a large molecule composed of smaller subunits of a type that are found in biological systems. Examples of biological macromolecules include polypeptides, nucleic acids, and polysaccharides. Typically a biological macromolecule contains at least 3 subunits (e.g., amino acids, nucleosides, monosaccharides, etc.). The biological macromolecule may, but need not be, a naturally occurring polypeptide, nucleic acid, or polysaccharide. The biological macromolecule may be modified, e.g., it may be conjugated to a nonbiological molecule such as synthetic polymer, etc.

"Choroidal neovascularization" (CNV) refers to the abnormal development, proliferation, and/or growth of blood vessels arising from the choriocapillaris. The blood vessels typically extend through Bruch's membrane, RPE layer, and/or subretinal space.

A "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin.

A "complement-inhibiting fragment" of a VCCP or VCIP is a polypeptide fragment of the VCCP or VCIP that inhibits complement, e.g., the polypeptide fragment inhibits complement activation.

A "complement-inhibiting variant" of a VCCP or VCIP is a polypeptide variant of the VCCP or VCIP that inhibits complement, e.g., the variant interferes with complement activation.

"Concurrent administration" as used herein with respect to two or more agents, e.g., therapeutic agents, is administration performed using doses and time intervals such that the administered agents are present together within the body, or at a site of action in the body such as within the eye) over a time interval in not less than de minimis quantities, i.e., they are present together in non-negligible quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks, etc. Accordingly, the agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart). According to various embodiments of the invention agents administered within such time intervals may be considered to be administered at substantially the same time. In certain embodiments of the invention concurrently administered agents are present at effective concentrations within the body (e.g., in the blood and/or at a site of action such as the retina) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The de minimis concentration of an agent may be, for example, less than approximately 5% of the concentration that would be required to elicit a particular biological response, e.g., a desired biological response.

An "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to achieve one or more of the following: (i) inhibit or prevent drusen formation; (ii) cause a reduction in drusen number and/or size (drusen regression); (iii) cause a reduction in or prevent lipofuscin deposits; (iv) inhibit or prevent visual loss or slow the rate of visual loss; (v) inhibit choroidal neovascularization or slow the rate of choroidal neovascularization; (vi) cause a reduction in size and/or number of lesions characterized by choroidal neovascularization; (vii) inhibit choroidal neovascularization or slow the rate of retinal neovascularization; (viii) cause a reduction in size and/or number of lesions characterized by retinal neovascularization; (ix) improve visual acuity and/or contrast sensitivity; (x) inhibit or prevent photoreceptor or RPE cell atrophy or apoptosis, or reduce the rate of photoreceptor or RPE cell atrophy or apoptosis; (xi) inhibit or prevent progression of non-exudative macular degeneration to exudative macular degeneration; (xii) reduce one or more indicia of inflammation, e.g., the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc.

An "expression control sequence" refers to a nucleotide sequence in a polynucleotide that regulates the expression (transcription and/or translation) of a nucleotide sequence operatively linked thereto.

"Exudative" macular degeneration is used herein synonymously with "wet" type macular degeneration, as those terms are generally understood in the art, i.e., to refer to a macular degeneration related condition such as ARMD characterized by neovascularization.

"Fibrillar collagen solids" means the dry collagen solid content of fibrillar collagen. Fibrillar collagen is an insoluble collagen material wherein the collagen molecules interact to form microfibrils which themselves aggregate by side-to-side and end-to-end association to form stabilized collagen fibrils.

"Fusion protein" refers to a polypeptide that contains two or more different polypeptides or portions thereof joined together to form a single polypeptide chain. A recombinant polynucleotide that encodes a fusion protein may be created by removing the stop codon from the polynucleotide that encodes the first polypeptide and appending a polynucleotide that encodes the second polypeptide in frame, so that the resulting recombinant polynucleotide encodes a single polypeptide comprising the two polypeptides.

"Herpesvirus" refers to members of a family of complex, double-stranded DNA viruses constituting the family Herpesviridae. The family includes the subfamilies Alphaherpesvirinae, which includes herpes simplex virus-1 and -2 (HSV-1 and HSV-2), varicella zoster virus (VZV), bovine herpesvirus-1 (BHV-1), pseudorabies virus (PRV), and equine herpesvirus-1 and -3 (EHV-1 and EHV-4) and Gammaherpesvirinae, which includes Epstein Barr virus (EBV) and lymphotrophic herpesvirus saimiri (HVS). The herpesvirus family is described in Fields, B N, et al., Fields Virology, 3rd ed., Lippincott Williams & Wilkins, 2001.

"Identity" refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. By gap is meant a portion of a sequence that is not occupied by a residue. For example, the sequence A K L - - - S I G (SEQ ID NO: 11) contains a gap of three residues. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between a sequence of interest and sequences in any of a variety of public databases. The algorithm of Karlin and Altschul (Karlin and Altschul, *Proc. Natl. Acad. Sci. USA* 87:22264-2268, 1990) modified as in Karlin and Altschul, *Proc. Natl. Acad. Sci. USA* 90:5873-5877, 1993 is incorporated into the NBLAST and XBLAST programs of Altschul et al. (Altschul, et al., *J. Mol. Biol.* 215:403-410, 1990). To obtain gapped alignments for comparison purposes, Gapped BLAST is utilized as described in Altschul et al. (Altschul, et al. *Nucleic Acids Res.* 25: 3389-3402, 1997). When utilizing BLAST and Gapped BLAST programs, the default parameters of the respective programs are used. A PAM250 or BLOSUM62 matrix may be used. See the Web site having URL www.ncbi.nlm.nih.gov for these programs. In a specific embodiment, percent identity of a sequence of interest and a second sequence is calculated using BLAST2 with default parameters.

The term "isolated" means 1) separated from at least some of the components with which it is usually associated in nature; 2) prepared or purified by a process that involves the hand of man; and/or 3) not occurring in nature. For example, a molecule that is removed from a cell that produces it, is "isolated". A chemically synthesized molecule is "isolated".

The term "linked", when used with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

"Liposomes" are artificial microscopic spherical particles formed by a lipid bilayer (or multilayers) enclosing an aqueous compartment. Liposomes are commonly used as a delivery vehicle for various types of molecules (such as proteins, small molecules, DNA, and RNA), including a number of different drugs and can be used for delivering certain of the compositions of the invention.

"Local administration" or "local delivery", in reference to delivery of a composition or agent of the invention, refers to delivery that does not rely upon transport of the composition or agent to its intended target tissue or site via the vascular system. The composition or agent may be delivered directly to its intended target tissue or site, or in the vicinity thereof, e.g., in close proximity to the intended target tissue or site. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site. It will be understood that once having been locally delivered a fraction of a therapeutic agent (typically only a minor fraction of the administered dose) may enter the vascular system and be transported to another location, including back to its intended target tissue or site.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and/or capillary endothelial cells. ARMD is the major macular degeneration related condition, but a number of others are known including, but not limited to, Best macular dystrophy, Sorsby fundus dystrophy, Mallatia Leventinese and Doyne honeycomb retinal dystrophy.

"Marker", for the purpose of the description of the invention, may refer to any molecular moiety (e.g., protein, peptide, mRNA or other RNA species, DNA, lipid, carbohydrate) that characterizes, indicates, or identifies a particular diseased or physiological state (e.g., apoptotic, cancerous, normal) or characterizes, indicates, or identifies one or more cell type(s), tissue type(s), or embryological origin. The presence or absence of certain marker(s), or the amount of certain marker(s), may indicate a particular physiological or diseased state of a patient, organ, tissue, or cell. A cellular marker is a marker found in or on a cell. A cellular marker may, but need not be, cell type specific. For example, a cell type specific marker is generally a protein, peptide, mRNA, lipid, or carbohydrate that is present at a higher level on or in a particular cell type or cell types of interest than on or in many other cell types. In some instances a cell type specific marker is present at detectable levels only on or in a particular cell type of interest. However, it will be appreciated that useful markers need not be absolutely specific for the cell type of interest. For example, certain CD molecules are present on the cells of multiple different types of leukocytes. In general, a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. More preferably the cell type specific marker is present at levels at least 4-5 fold, between 5-10 fold, or more than 10-fold greater than its average expression in a reference population. Preferably detection or measurement of a cell type specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

"Non-exudative" macular degeneration is used herein synonymously with "dry" type macular degeneration as those terms are generally used in the art, to refer to a macular degeneration related condition, e.g., ARMD, in which neovascularization that would be detectable using standard methods such as fluorescein angiography has not occurred.

"Operably linked" or "operably associated" refers to a relationship between two nucleic acid sequences wherein the expression of one of the nucleic acid sequences is controlled by, regulated by, modulated by, etc., the other nucleic acid sequences, or a relationship between two polypeptides wherein the expression of one of the polypeptides is controlled by, regulated by, modulated by, etc., the other polypeptide. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport, stability, or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence, or a polypeptide that is operatively linked to a second polypeptide, is covalently linked, either directly or indirectly, to such a sequence, although any effective three-dimensional association is acceptable.

"Plurality" means more than one.

"Polynucleotide" or "oligonucleotide" refers to a polymer of nucleotides. As used herein, an oligonucleotide is typically less than 100 nucleotides in length. A polynucleotide or oligonucleotide may also be referred to as a nucleic acid. Typically, a polynucleotide comprises at least three nucleotides. A nucleotide comprises a nitrogenous base, a sugar molecule, and a phosphate group. A nucleoside comprises a nitrogenous base linked to a sugar molecule. In a polynucleotide or oligonucleotide, phosphate groups covalently link adjacent nucleosides to form a polymer. The polymer may comprise or natural nucleosides found in DNA or RNA (e.g., adenosine, thymidine, guanosine, cytidine, uridine, deoxyadenosine, deoxythymidine, deoxyguanosine, and deoxycytidine), other nucleosides or nucleoside analogs, nucleosides containing chemically modified bases and/or biologically modified bases (e.g., methylated bases), intercalated bases, modified sugars, etc. The phosphate groups in a polynucleotide or oligonucleotide are typically considered to form the internucleoside backbone of the polymer. In naturally occurring nucleic acids (DNA or RNA), the backbone linkage is via a 3' to 5' phosphodiester bond. However, polynucleotides and oligonucleotides containing modified backbones or non-naturally occurring internucleoside linkages can also be used in the present invention. Such modified backbones include ones that have a phosphorus atom in the backbone and others that do not have a phosphorus atom in the backbone. Examples of modified linkages include, but are not limited to, phosphorothioate and 5'-N-phosphoramidite linkages. See Kornberg and Baker, *DNA Replication,* 2nd Ed. (Freeman, San Francisco, 1992), Scheit, *Nucleotide Analogs* (John Wiley, New York, 1980), U.S. Patent Pub. No. 20040092470 and references therein for further discussion of various nucleotides, nucleosides, and backbone structures that can be used in the polynucleotides or oligonucleotides described herein, and methods for producing them. Typically a polynucleotide of this invention is DNA or RNA.

Polynucleotides and oligonucleotides need not be uniformly modified along the entire length of the molecule. For example, different nucleotide modifications, different backbone structures, etc., may exist at various positions in the polynucleotide or oligonucleotide. Any of the polynucleotides described herein may utilize these modifications.

The polynucleotide may be of any size or sequence and may be single- or double-stranded. If single-stranded the polynucleotide may be the coding (sense) strand or non-coding (anti-sense) strand.

The polynucleotide may be provided by any means known in the art. In certain embodiments, the polynucleotide has been engineered using recombinant techniques (for a more detailed description of these techniques, please see Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may be synthesized using enzymatic techniques, either within cells or in vitro. The polynucleotide may also be chemically synthesized in a laboratory, e.g., using standard solid phase chemistry. The polynucleotide may be modified by chemical and/or biological means. In certain preferred embodiments, these modifications lead to increased stability of the polynucleotide. Modifications include methylation, phosphorylation, end-capping, etc.

The term "polynucleotide sequence" or "nucleic acid sequence" as used herein can refer to the nucleic acid material itself and is not restricted to the sequence information (i.e. the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated.

"Polypeptide", as used herein, refers to a polymer of amino acids. A protein is a molecule composed of one or more polypeptides. A peptide is a relatively short polypeptide, typically between about 2 and 60 amino acids in length. The terms "protein", "polypeptide", and "peptide" may be used interchangeably. Polypeptides used herein typically contain amino acids such as those that are naturally found in proteins. However, amino acids that are not naturally found in proteins (i.e., amino acids that either do or do not occur in nature and that can be incorporated into a polypeptide chain), and/or amino acid analogs can also or alternatively be used. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments the modification(s) lead to a more stable polypeptide (e.g., greater half-life in vivo or in vitro under conditions approximating physiological conditions) or a polypeptide having higher biological activity. Modifications may include cyclization of the peptide, the incorporation of D-amino acids, etc. Preferably the modification does not substantially interfere with the desired biological activity of the polypeptide. The natural or other chemical modifications such as those described above can occur anywhere in a polypeptide, including the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like.

Polypeptides of use in this invention (e.g., a VCCP, VCIP, collagen, etc.) may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or using methods involving chemical ligation of synthesized peptides (see, e.g., Kent, S., *J Pept Sci.*, 9(9):574-93, 2003 and U.S. Pub. No. 20040115774), or any combination of these.

The term "polypeptide sequence" or "amino acid sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. A polypeptide sequence presented herein is presented in an N-terminal to C-terminal direction unless otherwise indicated.

"Poxvirus" refers to a family of complex, double-stranded DNA viruses constituting the family Poxyiridae. The family includes the orthopoxviruses, a genus of the family Poxyiridae, subfamily Chordopoxyirinae, comprising many species infecting mammals, including human beings. Poxviruses are described in Fields, B N, et al., Fields Virology, $3^{rd}$ ed., Lippincott Williams & Wilkins, 2001. Orthopoxviruses include, but are not limited to, vaccinia virus, variola virus major, variola virus minor, cowpox virus, monkeypox virus, camelpox virus, swinepox virus, and ectromelia virus.

"Poxvirus complement control protein" refers to members of a family of homologous proteins encoded by a number of different poxviruses that bind to one or more complement pathway proteins and inhibit either the classical pathway of complement activation, the alternative pathway of complement activation, the lectin pathway, or any combination of these. Poxvirus complement control proteins are members of the complement control protein (CCP), also called regulators of complement activation (RCA) superfamily (Reid, K B M and Day, A J, *Immunol Today*, 10:177-80, 1989).

"Posterior segment of the eye" refers to the portion of the eye behind the lens, including the vitreous, choroid, and retina (including the macula).

"Purified", as used herein, means that an entity or substance is separated from one or more other entities or substances with which it was previously found before being purified. An entity or substance may be partially purified, substantially purified, or pure. A substance or entity such as a nucleic acid or polypeptide is considered pure when it is removed from substantially all other compounds or entities other than a solvent and any ions contained in the solvent, i.e., it constitutes at least about 90%, more preferably at least about 91%, 92%, 93%, 94%, 95%, 96%, 97%, 98%, 99%, or greater than 99% of the dry weight of the composition. A partially or substantially purified compound or entity such as a nucleic acid or polypeptide may be removed from at least 50%, at least 60%, at least 70%, or at least 80% by weight of the material with which it is naturally found, e.g., cellular material such as cellular proteins and/or nucleic acids. In certain embodiments the of a purified nucleic acid or polypeptide constitutes at least 10%, 20%, 30%, 40%, 50%, 60%, 70%, 80%, 90%, 95%, 99% or even more, by dry weight, of the total nucleic acid or polypeptide, respectively, in a composition. Methods for assessing purity are known in the art and include chromatographic methods, immunological methods, electrophoretic methods, etc. Any of the polynucleotides or polypeptides described herein may be purified.

"Recombinant host cells", "host cells", and other such terms, denote prokaryotic or eukaryotic cells or cell lines that have been used as recipients for an exogenous nucleic acid (typically DNA) such as an expression vector into which a nucleic acid portion that encodes a polypeptide of interest has been inserted. These terms include the progeny of the original cell into which the vector or other nucleic acid has been introduced. Appropriate unicellular host cells include any of those routinely used in expressing polynucleotides (e.g., eukaryotic, mammalian, and/or viral polynucleotides) including, for example, prokaryotes, such as *E. coli*; and eukaryotes, including for example, fungi, such as yeast (e.g., *Pichia pastoris*); insect cells (e.g., Sf9), plant cells, and animal cells, e.g., mammalian cells such as CHO, R1.1, B-W, L-M, African Green Monkey Kidney cells (e.g. COS-1, COS-7, BSC-1, BSC-40 and BMT-10) and cultured human cells. Terms such as "host cells", etc., are also used to refer to cells or cell lines that can be used as recipients for an exogenous nucleic acid, prior to its introduction. A "recombinant polynucleotide" is one that contains nucleic acid portions that are not found joined together in nature. A "recombinant polypeptide" is a polypeptide that is produced by transcription and translation of an exogenous nucleic acid by a recombinant host cell, typically after introduction of an expression vector that contains a portion that encodes the recombinant polypeptide into the host cell.

The term "regulatory element" or "regulatory sequence" in reference to a nucleic acid is generally used herein to describe a portion of nucleic acid that regulates one or more steps in the expression (particularly transcription, but in some cases other events such as splicing or other processing) of nucleic acid sequence(s) with which it is operatively linked. The term includes promoters and can also refer to enhancers and other transcriptional control elements. Promoters are regions of nucleic acid that include a site to which RNA polymerase binds before initiating transcription and that are typically necessary for even basal levels of transcription to occur. Such elements frequently comprise a TATA box. Enhancers are regions of nucleic acid that encompass binding sites for protein(s) that elevate transcriptional activity of a nearby or distantly located promoter, typically above some basal level of expression that would exist in the absence of the enhancer. In some embodiments of the invention, regulatory sequences may direct constitutive expression of a nucleotide sequence (e.g., expression in most or all cell types under typical physiological conditions in culture or in an organism); in other embodiments, regulatory sequences may direct cell or tissue-specific and/or inducible expression. For example, expression may be induced by the presence or addition of an inducing agent such as a hormone or other small molecule, by an increase in temperature, etc. Regulatory elements may also inhibit or decrease expression of an operatively linked nucleic acid. Such regulatory elements may be referred to as "negative regulatory elements".

"Retinal neovascularization" refers to the abnormal development, proliferation, and/or growth of blood vessels on or in the retina, e.g., on the retinal surface.

"Sequential administration" of two or more agents refers to administration of two or more agents to a subject such that the agents are not present together in the subject's body at greater than de minimis concentrations. Administration of the agents may, but need not, alternate. Each agent may be administered multiple times.

"Small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant or epitope recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. Binding of two or more molecules may be considered specific if the affinity (equilibrium dissociation constant, Kd) is at least $10^{-3}$ M, preferably $10^{-4}$ M, more preferably $10^{-5}$ M, e.g., $10^{-6}$ M, $10^{-7}$ M, $10^{-8}$ M, or $10^{-9}$ M under the conditions tested, e.g., under physiological conditions.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence. Percent identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L., *Biochemistry,* 3rd ed., 1988, according to which amino acids in the following groups possess similar features with respect to side chain properties such as size, charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P, which may be considered to fall within group (1). In another accepted classification, conservative substitutions occur within the following groups: (1) Non-polar: A, L, I, V, G, P, F, W, M; (2) Polar: S, T, C, Y, N, Q. (3) Basic: K, R, H; (4) Acidic: D, E. Amino acids with a small side chain (G, A, S, T, M) also form a group from among which conservative substitutions can be made.

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), non-human primates, or humans.

"Substantial sequence homology" as applied to a sequence means that the sequence displays at least approximately 60% identity, desirably at least approximately 70% identity, more desirably at least approximately 80% identity, and most desirably at least approximately 90% identity relative to a reference sequence. When two or more sequences are compared, any of them may be considered the reference sequence. % identity can be calculated using a FASTA, BLASTN, or BLASTP algorithm, depending on whether amino acid or nucleotide sequences are being compared. Default parameters may be used. A PAM250 or BLOSUM62 matrix may be used.

"Supramolecular complex" refers to an assembly comprising at least two entities that are physically associated with one another, in which one or more entities is not covalently linked to another entity but is instead associated with that entity by through one or more nonspecific noncovalent interactions mechanisms such as ionic interactions, hydrogen bonds, hydrophobic interactions, π-stacking, dative bonds, etc. For example, one or more entities may be entrapped, embedded, enclosed, or encapsulated within another entity, or entangled with another entity, or dissolved in another entity, or impregnated with another entity, or adsorbed to another entity, or bound to another entity, so as to maintain a physical association between the entities. The entities may be naturally occurring or synthetic. They may be, for example, polypeptides, non-polypeptide polymers, nucleic acids, lipids, small molecules, carbohydrates, etc. One or more of the entities may be a rigid or flexible polymer scaffold, a three-dimensional structure such as a microparticle, nanoparticle, liposome, dendrimer, etc. The supramolecular complex can contain any number or combination of molecules and/or other entities.

"Treating", as used herein, refers to providing treatment, i.e, providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur. Treating can include administering an agent to the subject following the development of one or more symptoms or manifestations indicative of a condition such as macular degeneration or diabetic retinopathy, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of this invention can be administered to a subject who has developed an eye disorder such as exudative or non-exudative ARMD or diabetic retinopathy or is at increased risk of developing such a disorder relative to a member of the general population. A composition of this invention can be administered prophylactically, i.e., before development of any symptom or manifestation of the condition. Typically in this case the subject will be at risk of developing the condition.

"Vector" is used herein to refer to a nucleic acid or a virus or portion thereof (e.g., a viral capsid) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof (e.g., viral capsids) that can be used to introduce nucleic acid molecules into cells are referred to as viral vectors. Useful viral vectors include adenoviruses, retroviruses, lentiviruses, vaccinia virus and other poxviruses, herpes simplex virus, and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Where sufficient information is lacking it may, but need not be, supplied by a host cell or by another vector introduced into the cell.

Expression vectors are vectors that include regulatory sequence(s), e.g., expression control sequences such as a promoter, sufficient to direct transcription of an operably linked nucleic acid. An expression vector comprises sufficient cis-acting elements for expression; other elements for expression can be supplied by the host cell or in vitro expression system. Such vectors typically include one or more appropriately positioned sites for restriction enzymes, to facilitate introduction of the nucleic acid to be expressed into the vector.

A "variant" of a particular polypeptide or polynucleotide has one or more alterations (e.g., additions, substitutions, and/or deletions, which may be referred to collectively as "mutations") with respect to the polypeptide or nucleic acid, which may be referred to as the "original polypeptide or polynucleotide". Thus a variant can be shorter or longer than the polypeptide or polynucleotide of which it is a variant. The terms "variant" encompasses "fragments". A "fragment" is a continuous portion of a polypeptide that is shorter than the original polypeptide. In certain embodiments of the invention a variant polypeptide has significant sequence homology to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In certain embodiments of the invention a variant polypeptide has substantial sequence homology to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In a non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In another non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In specific embodiments the sequence of a variant polypeptide has N amino acid differences with respect to an original sequence, wherein N is any integer between 1 and 10. In other specific embodiments the sequence of a variant polypeptide has N amino acid differences with respect to an original sequence, wherein N is any integer between 1 and 20. An amino acid "difference" refers to a substitution, insertion, or deletion of an amino acid.

In certain embodiments of the invention a fragment or variant possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, *J. Mol. Biol.*, 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., *Nucleic Acids Res.* 32(Web Server issue):W522-5, Jul. 1, 2004).

Preferably one, more than one, or all biological functions or activities of a variant or fragment is substantially similar to that of the corresponding biological function or activity of the original molecule. For example, an activity of a variant or fragment is considered substantially similar to the activity of the original molecule if the activity of the variant or fragment is at least 20%, at least 50%, at least 60%, at least 70%, at least 80%, or at least 90% of the activity of the original molecule, up to approximately 100%, approximately 125%, or approximately 150% of the activity of the original molecule. In other nonlimiting embodiments an activity of a variant or fragment is considered substantially similar to the activity of the original molecule if the amount or concentration of the variant needed to produce an effect is within 0.5 to 5-fold of the amount or concentration of the original molecule needed to produce that effect.

DETAILED DESCRIPTION OF CERTAIN EMBODIMENTS OF THE INVENTION

Overview

The present invention provides compositions and methods for treatment of eye disorders characterized by macular degeneration, choroidal neovascularization, retinal neovascularization, ocular inflammation, or any combination of the foregoing. The phrase "characterized by" is intended to indicate that macular degeneration, CNV, RNV, and/or ocular inflammation is a characteristic (i.e., typical) feature of the disorder. Macular degeneration, CNV, RNV, and/or macular degeneration may be a defining and/or diagnostic feature of the disorder. Exemplary disorders that are characterized by one or more of these features and can be treated with the compositions and methods of the invention include, but are not limited to, macular degeneration related conditions, diabetic retinopathy, retinopathy of prematurity, uveitis, keratitis, and scleritis.

As mentioned above, macular degeneration refers to a variety of degenerative conditions characterized by central visual loss due to deterioration of the macula. By far the most common of these conditions is age related macular degeneration (ARMD), which exists in both "dry" and "wet" forms.

Ocular inflammation can affect a large number of eye structures including the conjunctiva, cornea, episclera, sclera, uveal tract, retina, vasculature, optic nerve, and orbit. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. Uveitis can arise from a number of different causes and is associated with a number of different diseases, including, but not limited to, rheumatic diseases such as rheumatic diseases (e.g., ankylosing spondylitis and juvenile rheumatoid arthritis), certain infectious diseases such as tuberculosis and syphilis, other conditions such as sarcoidosis, systemic lupus erythematosus, chemical injury, trauma, surgery, etc. Keratis refers to inflammation of the cornea. Keratitis has a diverse array of causes including bacterial, viral, or fungal infection, trauma, and allergic reaction. Amoebic infection of the cornea, e.g., caused by Acanthamoeba, is a particular problem for contact lens wearers. Scleritis refers to inflammation of the sclera. Uveitis, keratitis, and scleritis, and methods for their diagnosis are well known in the art. Symptoms of the various inflammatory conditions that affect the eye can include, but are not limited to, eye pain, redness, light sensitivity, tearing, blurred vision, floaters. Ocular inflammation of various types is well known to occur in association with a variety of local or systemic diseases, some of which are noted above. In some instances the cause may remain unknown.

The invention provides a method of treating an eye disorder characterized by macular degeneration, choroidal neovascularization, retinal neovascularization, ocular inflammation, or any combination of these, comprising (i) providing a subject in need of treatment for the eye disorder; and (ii) administering a composition comprising a viral complement control protein (VCCP) to the subject. The invention further provides a method of treating an eye disorder characterized by macular degeneration, choroidal neovascularization, retinal neovascularization, ocular inflammation, or any combination of these, comprising (i) providing a subject in need of treatment for the eye disorder; and (ii) administering a composition comprising a complement inhibiting fragment or variant of a VCCP to the subject. The invention further provides a method of inhibiting CNV, RNV, or both, in the eye of a subject suffering from or at risk of an eye disorder characterized by macular degeneration, choroidal neovascularization, retinal neovascularization, or any combination of these, comprising the step of: administering a composition comprising a VCCP to or in close proximity to the posterior segment of the subject's eye.

The invention further provides a method of inhibiting ocular inflammation in the eye of a subject suffering from or at risk of an eye disorder characterized by ocular inflammation, comprising the step of: administering a composition comprising a VCCP to or in close proximity to the posterior segment of the subject's eye.

The events that occur in ARMD may be understood with reference to the various panels of FIG. 1. FIGS. 1A and 1B show structures present in the anterior and posterior segments of the eye, including the retina, which contains the macula. FIGS. 1C-1E depict the outer layers of a normal eye (1C), an eye suffering from dry ARMD (1D), and an eye suffering from exudative (wet) ARMD (1E). The outer nuclear layer (ONL), contains nuclei of rod and cone photoreceptors. Each photoreceptor contains an inner segment (IS) and outer segment (OS), the latter of which contains the pigment rhodopsin, which initiates the phototransduction cascade following exposure to light. The retinal pigment epithelial layer (RPE) lies below the photoreceptors and above Bruch's membrane, a layer of extracellular matrix that separates the RPE from a network of capillaries, the choriocapillaris (CC).

Dry ARMD is characterized by the existence of deposits known as drusen and the separation of the RPE from BM, which is accompanied by RPE atrophy and apoptosis and loss of underlying choriocapillaris and overlying photoreceptors, resulting in areas of geographic atrophy which can eventually coalesce to form large patches. In exudative ARMD, new blood vessels grow from the choriocapillaris through Bruch's membrane and can extend into the RPE and photoreceptor cell layers (choroidal neovascularization). These blood vessels can bleed and leak fluid, frequently resulting in sudden visual loss due to events such as RPE and/or retinal detachment. Eventually a fibrovascular scar may form, leading to irreversible visual loss. In some forms of neovascular ARMD, angiomatous proliferation originates from the retina and extends posteriorly into the subretinal space, eventually communicating in some cases with choroidal new vessels. This form of neovascular ARMD, termed retinal angiomatous proliferation (RAP), can be particularly severe. It has been suggested that angiomatous proliferation within the retina is the first manifestation of the vasogenic process in this form of neovascular ARMD. Dilated retinal vessels and pre-, intra-, and subretinal hemorrhages and exudate evolve, surrounding the angiomatous proliferation as the process extends into the deep retina and subretinal space.

The present invention provides compositions and methods that inhibit one or more of the events or processes that takes place in ARMD. The invention is based at least in part on the discovery that certain viral proteins, e.g., viral complement control proteins (VCCPs) are particularly suitable as therapeutic agents for macular degeneration and related conditions, for diabetic retinopathy, and for choroidal and/or retinal neovascularization due to these causes or others. For example, as described in Example 2, vaccinia virus complement control protein (VCP) was shown to be effective in significantly inhibiting the development of CNV in an animal model, i.e., VCP was effective in preventing at least some of the CNV that would otherwise have occurred. To the best of the inventors' knowledge, this work represents the first demonstration that administration of an inhibitor of complement activation to a subject is effective in inhibiting and at least partially preventing development of neovasculature in the eye and is the first demonstration that these agents will be effective treatments for eye disorders discussed herein.

Other viral proteins of use in the invention include, but are not limited to, viral complement interfering proteins. To facilitate understanding of the invention, the complement system will first be briefly outlined. Further information is found in the references cited herein. Subsequent sections describe the viral proteins of the present invention, compositions containing them, methods of use, etc.

Complement Pathways

The complement system plays a crucial role in a number of physiological processes including the response to injury and defense against foreign entities such as infectious agents. The complement system is also known to play a role in a number of diseases (Makrides, S C, *Pharm Rev.,* 50(1): 59-87). The complement system comprises more than 30 serum and cellular proteins that are involved in two major pathways, known as the classical and alternative pathways (*Kuby Immunology,* 2000).

The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylatoxins and mediate multiple reactions in the acute inflammatory response. C3a and C5a are also chemotactic factors that attract immune system cells such as neutrophils. C3 and C5 convertase activity is controlled by a number of endogenous members of the Regulators of Complement Activation (RCA) family, also called Complement Control Protein (CCP) family, which includes complement receptor type 1 (CR1; C3b:C4b receptor), complement receptor type 2 (CR2), membrane cofactor protein (MCP; CD46), decay-accelerating factor (DAF), factor H (fH), and C4b-binding protein (C4bp). Makrides, 1998, and references therein describe the complement system and its components. RCA proteins are also described in U.S. Pat. No. 6,897,290.

The alternative pathway is initiated by microbial surfaces and various complex polysaccharides. In this pathway, C3b, resulting from cleavage of C3, which occurs spontaneously at a low level, binds to targets on cell surfaces and forms a complex with factor B, which is later cleaved by factor D, resulting in a C3 convertase. Cleavage of C3 and binding of another molecule of C3b to the C3 convertase gives rise to a C5 convertase. C3 and C5 convertases of this pathway are regulated by CR1, DAF, MCP, and fH. The mode of action of these proteins involves either decay accelerating activity (i.e., ability to dissociate convertases), ability to serve as cofactors in the degradation of C3b or C4b by factor I, or both.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

A third complement pathway, the lectin complement pathway is initiated by binding of mannose-binding lectin (MBL) and MBL-associated serine protease (MASP) to carbohydrates. In the human lectin pathway, MASP-1 and MASP-2 are involved in the proteolysis of C4, C2 and C3, leading to a C3 convertase described above.

Figure 2:
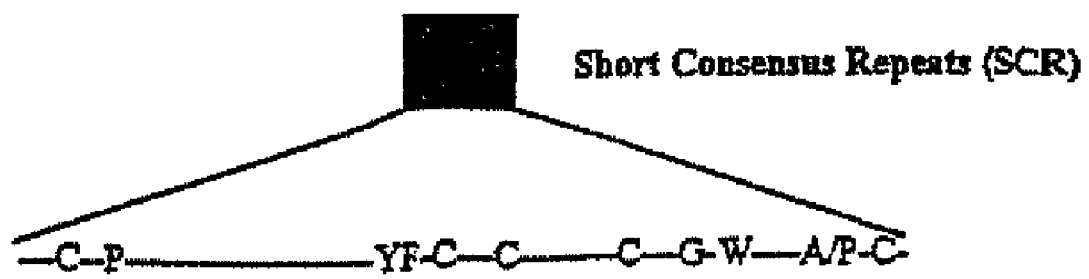
FIG. 2 shows a consensus sequence for a short consensus repeat (SCR), a module found in complement control proteins. From Smith, S A, et al., *J. Virol.* 74(12), 5659-5666, 2000.

As mentioned above, complement activity is regulated by various mammalian proteins referred to as complement control proteins (CCPs). These proteins differ with respect to ligand specificity and mechanism(s) of complement inhibition (Lisczewski, M K and Atkinson, J P, in *The Human Complement System in Health and Disease,* eds. Volanakis, J E and Frank, M M, Dekker, New York, pp. 149-66, 1998). They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains (Reid, K B M and Day, A J, Immunol Today, 10:177-80, 1989). These domains, consisting of approximately 50-70 amino acids, typically about 60 amino acids, are characterized by a conserved motif that includes four disulfide-bonded cysteines (two disulfide bonds), proline, tryptophan, and many hydrophobic residues. FIG. 2 shows an SCR consensus sequence. It is to be understood that any particular SCR may differ from the consensus at one or more positions.

Virus Complement Control Proteins and Methods of Use Thereof

The present invention provides a method of treating an eye disorder characterized by macular degeneration, choroidal neovascularization, retinal neovascularization, or any combination of these, comprising steps of: (i) providing a patient at risk of or suffering from the eye disorder; and (ii) administering a composition comprising a VCCP to the subject. The invention further provides a method of treating an eye disorder characterized by macular degeneration, choroidal neovascularization, retinal neovascularization, or any combination of these, comprising steps of: (i) providing a patient at risk of or suffering from the eye disorder; and (ii) administering a composition comprising a complement inhibiting variant or fragment of a VCCP to the subject. Viral complement control proteins (VCCPs) encoded by members of the poxvirus or herpesvirus families are of particular use in the present invention.

Poxviruses and herpesviruses are families of large, complex viruses with a linear double-stranded DNA genome. A number of these viruses infect animals and can cause a range of diseases, the most feared of which in humans is smallpox. Certain of these viruses encode a number of immunomodulatory proteins that are believed to play a role in pathogenesis by subverting one or more aspects of the normal immune response and/or fostering development of a more favorable environment in the host organism (Kotwal, G J, *Immunology Today,* 21(5), 242-248, 2000). Among these are viral complement control proteins. Poxvirus complement control proteins are members of the complement control protein (CCP) superfamily and typically contain 4 SCR modules. The invention features the discovery that these proteins possess features that make them particularly advantageous for treatment and prevention of macular degeneration related conditions and for treatment and prevention of choroidal neovascularization.

Thus in certain embodiments of the invention the VCCP is a poxvirus complement control protein (PVCCP). The PVCCP can comprise a sequence encoded by, e.g., vaccinia virus, variola major virus, variola minor virus, cowpox virus, monkeypox virus, ectromelia virus, rabbitpox virus, myxoma virus, Yaba-like disease virus, or swinepox virus. In other embodiments the VCCP is a herpesvirus complement control protein (HVCCP). The HVCCP can comprise a sequence encoded by a *Macaca fuscata* rhadinovirus, cercopithecine herpesvirus 17, or human herpes virus 8. In other embodiments the HVCCP comprises a sequence encoded by herpes simplex virus saimiri ORF 4 or ORF 15 (Albrecht, J C &

Fleckenstein, B., J. Virol., 66, 3937-3940, 1992; Albrecht, J., et al., Virology, 190, 527-530, 1992).

The VCCP may inhibit the classical complement pathway, the alternate complement pathway, the lectin pathway, or any combination of these. In certain embodiments of the invention the VCCP, e.g., a PVCCP, binds to C3b, C4b, or both. In certain embodiments of the invention the PVCCP comprises one or more putative heparin binding sites (K/R-X-K/R) and/or possesses an overall positive charge. Preferably the PVCCP comprises at least 3 SCR modules (e.g., modules 1-3), preferably 4 SCR modules. The PVCCP protein can be a precursor of a mature PVCCP (i.e., can include a signal sequence that is normally cleaved off when the protein is expressed in virus-infected cells) or can be a mature form (i.e., lacking the signal sequence).

Vaccinia complement control protein (VCP), the first poxvirus complement control protein to be identified, is a virus-encoded protein secreted from vaccinia infected cells. VCP is 244 amino acids in length, contains 4 SCRs, and is naturally produced by intracellular cleavage of a 263 amino acid precursor. VCP runs as an 35 kD protein in a 12% SDS/polyacrylamide gel under reducing conditions and has a predicted molecular mass of about 28.6 kD. VCP is described in U.S. Pat. Nos. 5,157,110 and 6,140,472, and in Kotwal, G K, et al., *Nature*, 355, 176-178, 1988. FIGS. 3A and 3B show the sequence of the precursor and mature VCP proteins, respectively. VCP has been shown to inhibit the classical pathway of complement activation via its ability to bind to C3 and C4 and act as a cofactor for factor I mediated cleavage of these components as well as promoting decay of existing convertase (Kotwal, G K, et al., *Science*, 250, 827-830, 1990; McKenzie et al., *J. Infect. Dis.*, 1566, 1245-1250, 1992). It has also been shown to inhibit the alternative pathway by causing cleavage of C3b into iC3b and thereby preventing the formation of the alternative pathway C3 convertase (Sahu, A, et al., *J. Immunol.*, 160, 5596-5604, 1998). VCP thus blocks complement activation at multiple steps and reduces levels of the proinflammatory chemotactic factors C3a, C4a, and C5a.

VCP also possesses the ability to strongly bind heparin in addition to heparan sulfate proteoglycans. VCP contains two putative heparin binding sites located in modules 1 and 4 (Jha, P and Kotwal, G J, and references therein). VCP is able to bind to the surface of endothelial cells, possibly via interaction with heparin and/or heparan sulfate at the cell surface, resulting in decreased antibody binding (Smith, S A, et al., *J. Virol.*, 74(12), 5659-5666, 2000). VCP can be taken up by mast cells and possibly persist in tissue for lengthy periods of time, thereby potentially prolonging its activity (Kotwal, G J, et al., In G P. Talwat, et al. (eds), 10$^{th}$ International Congress of Immunology., Monduzzi Editore, Bologna, Italy, 1998). In addition, VCP can reduce chemotactic migration of leukocytes by blocking chemokine binding (Reynolds, D, et al., in S. Jameel and L. Villareal (ed., *Advances in animal virology*. Oxford and IBN Publishing, New Delhi, India, 1999). VCP and other PVCCPs have a relatively small size relative to mammalian CCPs, which is advantageous for delivery. The crystal structure of VCP has been determined (Murthy, K H M, et al., *Cell*, 104, 301-311, 2001). In addition, solution structures of various recombinantly produced proteins containing 2 or 3 SCRs from VCP have been determined.

Variola virus major and minor encode proteins that are highly homologous to VCP and are referred to as smallpox inhibitor of complement enzymes (SPICE) (Rosengard, A M, et al., *Proc. Natl. Acad. Sci.*, 99(13), 8803-8813. U.S. Pat. No. 6,551,595). SPICE from various variola strains sequenced to date differs from VCP by about 5% (e.g., about 11 amino acid differences). Similarly to VCP, SPICE binds to C3b and C4b and causes their degradation, acting as a cofactor for factor I. However, SPICE degrades C3b approximately 100 times as fast as VCP and degrades C4b approximately 6 times as fast as VCP. The amino acid sequence of SPICE is presented in FIG. 6 (SEQ ID NO: 12) and can be described as follows. Referring to FIG. 6, a signal sequence extends from amino acid 1 to about amino acid 19. Four SCRs extend from about amino acid 20 to amino acid 263. Each SCR is characterized by four cysteine residues. The four cysteine residues form two disulfide bonds in the expressed protein. The boundaries of each SCR are best defined by the first and fourth cysteine residues in the sequence that forms the disulfide bonds of the SCR. An invariant tryptophan residue is present between cysteine 3 and cysteine 4 of each SCR. SCR1 extends from amino acid 20 or 21 to amino acid 81. Both residues are cysteines that may be involved in disulfide bonding. SCR2 extends from amino acid 86 to amino acid 143. SCR3 extends from amino acid 148 to amino acid 201. SCR4 extends from amino acid 206 to amino acid 261. The SCRs include the complement binding locations of SPICE. SPICE or any of the portions thereof that inhibit complement activation, e.g., SPICE and SPICE-related polypeptides containing four SCRs, such as those described in U.S. Pat. No. 6,551,595, are of use in the present invention.

Complement control proteins from cowpox virus (referred to as inflammation modulatory protein, IMP) and monkeypox virus (referred to herein as monkeypox virus complement control protein, MCP) have also been identified and sequenced (Miller, C G, et al., *Virology*, 229, 126-133, 1997 and Uvarova, E A and Shchelkunov, S N, *Virus Res.*, 81(1-2), 39-45, 2001). MCP differs from the other PVCCPs described herein in that it contains a truncation of the C-terminal portion of the fourth SCR.

It will be appreciated that the exact sequence of complement control proteins identified in different virus isolates may differ slightly. Such proteins fall within the scope of the present invention. Complement control proteins from any such isolate may be used, provided that the protein has not undergone a mutation that substantially abolishes its activity. Thus the sequence of a VCCP such as SPICE or VCP may differ from the exact sequences presented herein or under the accession numbers listed in Table 1. It will also be appreciated that a number of amino acid alterations, e.g., additions, deletions, or substitutions such as conservative amino acid substitutions, may be made in a typical polypeptide such as a VCCP without significantly affecting its activity, such that the resulting protein is considered equivalent to the original polypeptide. For example, up to about 10% of the amino acids, or up to about 20% of the amino acids may frequently be changed without significantly altering the activity. Also, of course, domains known to have similar functions can be substituted for one another. Such domains may be found within a single polypeptide (e.g., repeated domains) or within different, homologous polypeptides. The effect of any particular amino acid alteration(s) or domain substitutions can readily be determined.

FIG. 4 shows a sequence alignment of a variety of poxvirus complement control proteins from isolates of variola major and minor, vaccinia, cowpox virus, and monkeypox virus. FIG. 5 shows a comparison of the SCR domain structure of a number of complement control proteins and fragments thereof, the number of K+R residues, % K+R residues, pI, number of putative heparin binding sites, and ability to inhibit hemolysis (indicative of complement inhibiting activity) and/or bind to heparin.

Without limitation, any of the viral polypeptides identified by accession number in Table 1 below is of use in various embodiments of the invention.

TABLE 1

Representative Viral Complement Control Proteins

| Virus | Protein | Accession | Virus Type |
|---|---|---|---|
| Variola | D12L | NP_042056 | Orthopoxvirus |
| | D15L (SPICE) | AAA69423 | Orthopoxvirus |
| Vaccinia | VCP | AAO89304 | Orthopoxvirus |
| Cowpox | CPXV034 | AAM13481 | Orthopoxvirus |
| | C17L | CAA64102 | Orthopoxvirus |
| Monkeypox | D14L | AAV84857 | Orthopoxvirus |
| Ectromelia virus | Complement control protein | CAE00484 | Orthopoxvirus |
| Rabbitpox | RPXV017 | AAS49730 | Orthopoxvirus |
| Macaca fuscata rhadinovirus | JM4 | AAS99981 | Rhadinavirus (Herpesvirus) |
| Cercopithecine herpesvirus 17 | Complement binding protein (ORF4) | NP_570746 | Herpesvirus |
| Human herpes virus 8 | Complement binding protein (ORF4) | AAB62602 | Herpesvirus |

Viral Complement Interfering Proteins

In addition to the VCCPs described above, there are a number of other viral proteins that interfere with one or more steps in a complement pathway. These proteins are also of use in the present invention. Unlike the VCCPs, certain of these proteins do not necessarily display clear homology to cellular complement regulators. For example, HSV-1, HSV-2, VZV, PRV, BHV-1, EHV-1, and EHV-4 all encode versions of a conserved glycoprotein known as gC (Schreurs, et al., *J. Virol.*, 62, 2251-2257, 1988; Mettenleiter, et al, *J. Virol.*, 64, 278-286; 1990; Herold, et al., *J. Virol.*, 65, 1090-1098; 1991). With the exception of VZV, the gC protein encoded by these viruses binds to C3b (Friedman, et al., *Nature*, 309, 633-634, 1984; Huemer, et al., *Virus Res.*, 23, 271-280, 1993) gC1 (from HSV-1) accelerates decay of the classical pathway C3 convertase and inhibits binding of properdin and C5 to C3. Purified EBV virions possess an activity that accelerates decay of the alternative pathway C3 convertase and serves as a cofactor for the complement regulatory protein factor 1 (Mold et al., *J Exp Med*, 168, 949-969, 1988). The foregoing proteins are referred to collectively as virus complement interfering proteins (VCIPs). By any of a variety of means, such as interfering with one or more steps of complement activation, accelerating decay of a complement component, and/or enhancing activity of a complement regulatory protein, these VCIPs are said to inhibit complement. Any of these proteins, or derivatives thereof, e.g., fragments or variants thereof, can be used as a therapeutic agent in the invention. As in the case of VCCPs, will be appreciated that the exact sequence of VCIPs identified in different virus isolates may differ slightly. Such proteins fall within the scope of the present invention. In general, VCIPs may be used in a manner similar to the methods described herein for VCCPs, and wherever a method or composition involving a VCCP is described, it should be understood that the invention also provides similar methods involving a VCIP, even if not specifically set forth herein, unless indicated otherwise.

Fragments and Variants of a VCCP or VCIP

In certain embodiments of the invention a fragment or variant of a VCCP or VCIP is administered to a subject to treat or prevent an eye disorder characterized by macular degeneration, choroidal neovascularization, retinal neovascularization, or any combination of these. A fragment of a VCCP or VCIP contains fewer amino acids than the VCCP or VCIP while a variant may contain fewer, more, or the same number of amino acids as the VCCP or VCIP. Preferred fragments and variants of a PVCCP possess at least one of the following activities: (i) ability to bind to C3, C3b, or both; (ii) ability to act as a cofactor for factor I cleavage of C3; (iii) ability to bind to C4, C4b, or both; (iv) ability to act as a cofactor for factor I cleavage of C4; (v) ability to accelerate decay of existing C3 convertase of the classical pathway, alternate pathway, or both; (vi) ability to bind heparin; (vii) ability to bind to heparan sulfate proteoglycans; (viii) ability to reduce chemotactic migration of leukocytes; (ix) ability to block chemokine (e.g, MIP-1α) binding, e.g., to the surface of a cell (e.g., a leukocyte or endothelial cell surface); (x) ability to inhibit antibody binding to class I MHC molecules; (xi) ability to inhibit the classical complement pathway; (xii) ability to inhibit the alternative complement pathway; and (xiii) ability to inhibit complement-mediated cell lysis. Preferred PVCCP fragments and variants display complement binding activity, by which is meant ability to detectably bind to one or more complement components, preferably selected from the group consisting of: C3, C3b, C4, and C4b. Preferred fragments or variants of HVCCPs may also display ability to detectably bind to one or more complement components. Preferably the binding of the VCCP to the complement component is specific. It will be understood that a VCCP may be able to bind to only a single complement component or may be able to bind to more than one different complement component. Preferred VCCP fragments and variants are able to detectably inhibit the classical complement pathway, alternate complement pathway, or both. Complement inhibiting or complement component binding activity can be measured using any of a variety of methods known in the art.

Preferably a fragment or variant displaying any of the above activities displays such activity at a level at least 10%, at least 20%, at least 30%, at least 40%, or at least 50% of the activity of VCP. In yet more preferred embodiments of the invention the fragment or variant displays at least 60%, at least 70%, at least 80%, at least 90%, or about 100% of the activity of VCP. In other preferred embodiments the fragment or variant displays at least 10%, at least 20%, at least 30%, at least 40%, or at least 50% of the activity of SPICE. In yet more preferred embodiments of the invention the fragment or variant displays at least 60%, at least 70%, at least 80%, at least 90%, or about 100% of the activity of SPICE. In certain embodiments a fragment or variant displays one or more activities at a greater level than VCP or at a greater level than SPICE. In certain embodiments of the invention a fragment or variant displays an activity at a level at least 10%, at least 20%, at least 30%, at least 40%, or at least 50% of the activity of SPICE. In yet more preferred embodiments of the invention the fragment or variant displays at least 60%, at least 70%, at least 80%, at least 90%, or about 100% of the activity of SPICE. In certain embodiments a fragment or variant displays one or more activities at a greater level than SPICE.

In general, fragments and variants of a VCIP fulfill similar criteria as those described above for fragments or variants of a VCCP, except that the relevant activity is complement interfering activity or complement component binding activity of the naturally occurring VCIP.

Certain variants of a naturally occurring VCCP or VCIP contain one or more conservative amino acid substitutions with respect to the naturally occurring form. Certain variants of a naturally occurring VCCP contain only conservative amino acid substitutions with respect to the naturally occurring form.

The invention encompasses the use of VCCPs or VCIPs discussed herein that differ from their naturally occurring counterparts by one or more amino acid substitutions, additions, or deletions. Each amino acid added to, deleted from, or altered in the naturally occurring amino acid sequence with respect to the naturally occurring sequence is considered to constitute an amino acid difference. The minimum number of such additions, deletions, or alterations that must be performed to arrive at the fragment or variant is considered to be the number of differences. In certain embodiments of the invention a VCCP or VCIP contains 1, 2, 3, 4, or 5 amino acid differences, 5-10 amino acid differences, 10-15 amino acid differences, 15-25 amino acid differences, 25-50 amino acid differences, or 50-100 amino acid differences with respect to its naturally occurring counterpart. In certain embodiments of the invention the number of amino acid differences between a naturally occurring VCCP or VCIP and a fragment or variant thereof for use in the invention is 5% or less, 10% or less, or 25% or less of the total number of amino acids in the naturally occurring protein. Preferred fragments of a VCCP comprise at least 3 SCR modules, preferably 4 SCR modules.

In certain embodiments of the invention a fragment or variant of a naturally occurring VCCP is at least 20% identical, at least 30% identical, at least 40% identical, at least 50% identical, at least 60% identical, at least 70% identical, at least 80% identical, at least 90% identical, at least 95% identical to its naturally occurring counterpart, over one or more SCR modules, e.g., 1, 2, 3, or 4 SCR modules. The amino acid portion is preferably at least 20 amino acids in length, more preferably at least 50 amino acids in length.

In certain embodiments of the invention a fragment or variant displays significant sequence homology to a naturally occurring PVCCP encoded by a vaccinia virus, variola major virus, variola minor virus, cowpox virus, or monkeypox virus. Preferably the fragment or variant possesses ability to bind to one or more complement components. Preferably the fragment or variant displays substantial sequence homology to a naturally occurring PVCCP over the length of the fragment or variant. The PVCCP fragment or variant may inhibit the classical complement pathway, the alternate complement pathway, or both. In certain embodiments of the invention the PVCCP fragment or variant binds to C3b, C4b, or both. In certain embodiments of the invention the PVCCP fragment or variant comprises one or more putative heparin binding sites (K/R-X-K/R) and/or possesses an overall positive charge.

In preferred embodiments of the invention the PVCCP fragment or variant comprises at least 3 SCR modules (e.g., modules 1-3), preferably 4 SCR modules. Preferably each of the SCR modules displays significant sequence homology or, more preferably, substantial sequence homology, to an SCR module found in a naturally occurring PVCCP, e.g., VCP or SPICE. Preferably the multiple SCR modules are arranged in an N to C manner so as to maximize overall identity to a naturally occurring PVCCP. If the sequence of a PVCCP fragment or variant contains an SCR domain that differs from the SCR consensus sequence at one or more positions, in certain embodiments of the invention the amino acid(s) at the one or more differing positions is identical to that found at a corresponding position in the most closely related SCR found in a naturally occurring PVCCP. In certain embodiments the PVCCP variant comprises at least one SCR module from a first PVCPP and at least one SCR module from a second PVCPP. In certain embodiments the PVCCP variant comprises at least one SCR module from a PVCCP and at least one SCR from a mammalian complement control protein (RCA protein). Any number of SCR modules, e.g., 1, 2, 3, 4, or more can come from any particular PVCCP or RCA protein in various embodiments of the invention. All such combinations and permutations are contemplated, even if not explicitly set forth herein.

Generally a fragment or variant of a naturally occurring VCCP or VCIP possesses sufficient structural similarity to its naturally occurring counterpart that it is recognized by a polyclonal antibody that recognizes the naturally occurring counterpart. In certain embodiments of the invention a fragment or variant of a VCCP possesses sufficient structural similarity to VCP or SPICE so that when its 3-dimensional structure (either actual or predicted structure) is superimposed on the structure of VCP or SPICE, the volume of overlap is at least 70%, preferably at least 80%, more preferably at least 90% of the total volume of the VCP structure. A partial or complete 3-dimensional structure of the fragment or variant may be determined by crystallizing the protein as described for VCP (Murthy, 2001). Alternately, an NMR solution structure can be generated, which has been performed for various VCP fragments (Wiles, A P, et al., *J. Mol. Biol.* 272, 253-265, 1997). A modeling program such as MODELER (Sali, A. and Blundell, T L, *J. Mol. Biol.,* 234, 779-815, 1993), or any other modeling program, can be used to generate a predicted structure. The model can be based on the VCP structure and/or any known SCR structure. The PROSPECT-PSPP suite of programs can be used (Guo, J T, et al., *Nucleic Acids Res.* 32(Web Server issue):W522-5, Jul. 1, 2004). Similar methods may be used to generate a structure for SPICE.

Fragments or variants of a VCCP or VCIP may be generated by any available means, a large number of which are known in the art. For example, VCCPs, VCIPs, and fragments or variants thereof can be produced using recombinant DNA technology as described below. Sequences for a VCCP or VCIP fragment may be chemically synthesized, produced using PCR amplification from a cloned VCCP or VCIP sequence, generated by a restriction digest, etc. Sequences for a VCCP variant may be generated by random mutagenesis of a VCCP sequence (e.g., using X-rays, chemical agents, or PCR-based mutagenesis), site-directed mutagenesis (e.g., using PCR or oligonucleotide-directed mutagenesis, etc. Selected amino acids can be changed or added.

While not wishing to be bound by any theory, it is likely that amino acid differences between naturally occurring PVCCPs occur at positions that are relevant in conferring differences in particular properties such as ability to bind heparin, activity level, etc. For example, VCP and SPICE differ at only 11 amino acids, but SPICE has a much higher activity as a cofactor for cleavage of C3b (e.g., cleavage occurs at a much faster rate with SPICE than with VCP). The amino acid differences are likely to be responsible for the differential activities of the two proteins. The amino acids at these positions are attractive candidates for alteration to identify variants that have yet greater activity.

Any variant or fragment may be tested as described below, e.g., using in vitro assays, virus-based assays, and/or by administering the variant or fragment to an animal that constitutes an experimental model for an eye disorder such as a macular degeneration related condition or diabetic retinopathy, e.g., an animal exhibiting choroidal neovascularization. A variant or fragment that treats or prevents one or more features of macular degeneration, diabetic retinopathy, and/or choroidal neovascularization in the animal is identified as a potentially useful therapeutic agent. Such agents may be further tested in other animal model systems and/or in human subjects.

It should be understood that the invention includes embodiments in which any of the methods of the invention in which a VCCP or VCIP is used are practiced using one or more effective fragments or variants of the VCCP or VCIP.

Producing a VCCP, VCIP, or a Fragment or Variant Thereof

A VCCP, VCIP, or a fragment or variant of either may be produced using any suitable method known in the art. For purposes of brevity, the following discussion refers to VCCPs, but it will be understood that the same methods can also be applied in the case of VCIPs. According to one approach, appropriate host cells (e.g., RK-13, L cells, etc.) can be infected with a virus that encodes a VCCP. The cells are maintained in culture and secrete VCCP into the medium. Medium is harvested, and the VCCP is purified therefrom using standard techniques such as concentration and column chromatography. U.S. Pat. No. 5,157,110 describes methods for obtaining a substantially pure preparation of VCP from virus-infected cells. Immunoaffinity chromatography with antibodies that specifically bind to the VCCP can be used. While not wishing to be bound by any theory, the relatively small size of certain VCCP such as PVCCPs (compared, for example, to a number of mammalian CCPs), facilitates their expression and purification.

Recombinant DNA technology can be used to produce a VCCP or a VCCP fragment or variant according to methods that are well known in the art. Suitable methods for producing any polypeptide of choice using recombinant DNA technology are described in U.S. Pub. No. 20030219406 and in numerous standard reference works. Briefly, a polynucleotide that encodes the VCCP or VCCP fragment or variant is obtained. The polynucleotide can be obtained, e.g., by cloning or PCR from virus or virus-infected cells. Polynucleotides encoding VCCPs have already been isolated and are available. Furthermore, a number of poxvirus and herpesvirus genomes encoding VCCPs have been completely sequenced. The polynucleotide is inserted into a suitable expression vector to generate a recombinant polynucleotide. The expression vector is selected such that it can direct expression of the recombinant polynucleotide in a host cell, resulting in production of a recombinant polypeptide. Thus once inserted into the expression vector, the coding sequence for the polynucleotide should be located in suitable proximity to appropriate expression control elements, e.g., regulatory elements such as a promoter, initiation signals, termination signals, polyadenylation signals, etc., depending upon the particular host cell into which the expression vector is to be introduced. One of ordinary skill in the art will be able to select appropriate expression control elements.

Numerous expression vectors suitable for use in prokaryotic or eukaryotic host cells are known in the art. Either plasmid or viral vectors can be used. For example, for expression in *E. coli* the pALTER™ or PinPoint™ vectors (Promega) can be used. For expression in *S. cerevisiae* pYES vectors, which contain a GAL promoter to drive expression, can be used. For expression in *Pichia pastoris* the pHIL-S1 vector can be used. *Pichia pastoris* expression systems have been used for expression of high levels of recombinant VCP and fragments thereof (Sahu, 1998). For expression in insect cells, a coding sequence can be inserted into a transfer vector such as pFastBac™ or pPolh (Sigma-Aldrich), which is then used to create a recombinant baculovirus that is used to infect insect cells. For expression in plant cells, a plant virus vector such as an alfalfa mosaic virus or tobacco mosaic virus vector, or *Agrobacterium tumefaciens* mediated gene transfer can be used. Transgenic plants or animals expressing the protein can be generated and used as a source. Methods for producing transgenic plants and animals are well known in the art.

For expression in mammalian cells, numerous vectors containing promoters functional in mammalian cells, such as the cytomegalovirus (CMV) promoter, herpes simplex virus (HSV) promoter, SV40 promoters, retroviral LTR, etc. are available. The promoter can be inducible or constitutive. In certain embodiments the expression vector comprises sites that permit homologous recombination into a host cell genome.

In certain embodiments of the invention the recombinant polypeptide comprises a signal sequence, also referred to as a signal peptide, so that the polypeptide is secreted. A variety of signal sequences are known in the art. Signal sequences are typically characterized by a core of hydrophobic amino acids which are generally cleaved from the mature protein during secretion in one or more cleavage events. Such signal peptides may contain processing sites that allow cleavage of the signal sequence from the mature proteins as they pass through the secretory pathway. Optionally any signal peptide present in the native VCCP or VCIP is removed and replaced with a signal peptide sequence from another polypeptide. In certain embodiments of the invention the recombinant polypeptide comprises a portion encoding a tag, e.g., a metal affinity tag (MAT) such as a 6×-His tag, HA tag, Myc tag, FLAG tag, GST tag, etc. Such tags may simplify the detection, isolation and/or purification of the protein. The recombinant polypeptide may comprise a cleavage site, which may be encoded by the inserted polynucleotide or by the vector. For example, the vector may comprise a portion that encodes a cleavage site upstream or downstream of a portion that encodes a tag, so that when a polynucleotide that encodes a VCCP or a VCCP fragment or variant is inserted between the portion that encodes the tag and the portion that encodes a cleavage site, the resulting open reading frame encodes a fusion protein containing a portion that comprises VCCP or a VCCP fragment or variant and a cleavage site. Cleavage of the fusion protein at the cleavage site releases the encoded VCCP or VCCP fragment or variant. The cleavage site may be a site for cleavage by chemical means (e.g., cyanogen bromide) or by enzymatic means (e.g., by a protease such as trypsin, chymotrypsin, thrombin, pepsin, *Staphylococcus aureus* V8 protease, and Factor Xa protease). Including a cleavage site allows the tag to be readily be removed from the translated polypeptide, if desired. Sequences encoding a signal sequence, tag and/or cleavage site may be present within a vector into which a particular polynucleotide is inserted and need not be present within the inserted polynucleotide itself. Members of the pFLAG™ and pMAT™ series of vectors (Sigma-Aldrich) can be used for expression of proteins with a FLAG or MAT tag in prokaryotic or mammalian cells.

The expression vector is introduced into an appropriate host cell using any of a variety of methods known in the art including calcium-mediated transformation, electroporation, calcium-phosphate transfection, cationic lipid-mediated transfection, microparticle bombardment, etc. Cells that have taken up the expression vector are typically selected by growth in or on a selective medium. A stable cell line can be generated. Alternately, transient transfection can be used. The cells are maintained in culture for a period of time to allow production of the recombinant polypeptide. Cells and/or medium are then harvested, and the polypeptide is purified. The invention thus provides polynucleotides, expression vectors, and host cells, that encode a VCCP or fragment or variant thereof and also polynucleotides, expression vectors, and host cells that encode a polypeptide containing a portion that comprises a VCCP or fragment or variant thereof and portion that binds to a cell or noncellular molecular entity (i.e., a binding moiety).

See, e.g., Hardin, C., et al., (Eds.), "Cloning, Gene Expression and Protein Purification: Experimental Procedures and Process Rationale", Oxford University Press, Oxford, 2001, for further information regarding production of recombinant polypeptides and purification of polypeptides.

In certain embodiments of the invention rather than administering a VCCP, VCCP fragment or variant, or a polypeptide comprising a VCCP or a VCCP fragment or variant and a binding moiety that binds to a component present on or at the surface of a cell or noncellular molecular entity to a subject, recombinant cells that produce the polypeptide are administered. Such cells may be generated similarly to the recombinant host cells used for protein expression (i.e., by introduction of a nucleic acid such as an expression vector that encodes the VCCP or VCCP fragment or variant into the cell). Preferably a stable cell line is generated. The cells may be, for example, neural stem cells, RPE stem cells, RPE cells, etc. These cells may help reconstitute damaged RPE and/or photoreceptors. In other embodiments of the invention any other cell type may be used. Autologous cells may be used. The cells can be introduced into the vitreous cavity or elsewhere.

Assessing Properties of a VCCP or VCIP or a Fragment or Variant Thereof

Any suitable method can be used for assessing any of the properties of a VCCP, VCIP, or a fragment or variant thereof, and such determination requires no more than routine experimentation. A number of in vitro assays can be used. For example, ability of an agent to inhibit the classical or alternative complement pathway may be assessed by measuring complement-mediated hemolysis of erythrocytes (e.g., antibody-sensitized or unsensitized rabbit or sheep erythrocytes), by human serum or a set of complement components in the presence or absence of the agent. An agent inhibits complement if it decreases hemolysis in this inhibition assay to a statistically significant degree ($p<0.05$). The $IC_{50}$ of recombinantly produced VCP for inhibition of the classical and alternative pathways (i.e., concentration required for 50% inhibition) has been measured (Sahu, 1998). In certain embodiments of the invention a VCCP or VCCP fragment or variant has an $IC_{50}$ that is less than 5 times the $IC_{50}$ of VCP (either recombinantly produced VCP or VCP purified from virus-infected cells can be used). Preferably the fragment or variant has an $IC_{50}$ that is less than 4 times, less than 3 times, less than 2 times that of VCP. Preferably the $IC_{50}$ is approximately equal to that of VCP (e.g., within 10% of the value for VCP), or even less than that of VCP. In certain embodiments of the invention a VCCP or VCCP fragment or variant has an $IC_{50}$ that is less than 5 times the $IC_{50}$ of SPICE (either recombinantly produced SPICE or SPICE purified from virus-infected cells can be used). Preferably the fragment or variant has an $IC_{50}$ that is less than 4 times, less than 3 times, less than 2 times that of SPICE. Preferably the $IC_{50}$ is approximately equal to that of SPICE (e.g., within 10% of the value for SPICE), or even less than that of SPICE.

The ability of an agent to bind to one or more complement components can be assessed using an ELISA assay. For example, the wells of a microtiter plate are coated with the agent. Complement component(s) are added to the wells. After a period of incubation the wells are washed, and bound complement components are detected using antibodies. A direct ELISA assay has been used to quantitatively measure the ability of recombinantly produced VCP to bind to C3 and fragments thereof (Sahu, 1998). Preferably the dissociation constant ($K_d$) of a VCCP or VCCP fragment or variant with respect to one or more complement components (e.g., C3, C3b, and/or C4b) is less than 100 times the $K_d$ of VCP with respect to the same component, preferably less than 10 times the $K_d$, more preferably less than 5 times or less than 2 times. Preferably the $K_d$ is approximately equal to that of VCP, or even lower than that of VCP. In certain embodiments of the invention the dissociation constant ($K_d$) of a VCCP or VCCP fragment or variant with respect to one or more complement components (e.g., C3, C3b, and/or C4b) is less than 100 times the $K_d$ of SPICE with respect to the same component, preferably less than 10 times the $K_d$, more preferably less than 5 times or less than 2 times. Preferably the $K_d$ is approximately equal to that of SPICE, or even lower than that of SPICE.

The ability of a VCCP fragment or variant, e.g., a PVCCP or PVCCP fragment or variant, to act as a cofactor for factor I mediated cleavage of a complement component, e.g., C3, C3b, etc., and the rate of such cleavage, may be determined by incubating the agent with the complement component and factor I for a period of time. Following incubation samples are subjected to electrophoresis to separate the components and cleavage products by size. Complement components and cleavage products thereof may be visualized using, for example, Coomassie staining, immunoblotting using antibodies that recognize the component, etc. A time course may be performed. Preferably the rate is more than 0.1 times the rate of VCP-activated cleavage, more preferably more than 0.5 times the rate of VCP-activated cleavage, yet more preferably approximately equal to the rate of VCP-activated cleavage, or even greater. In certain embodiments of the invention the rate is more than 1 times the rate of SPICE-activated cleavage, more preferably more than 0.5 times the rate of SPICE-activated cleavage, yet more preferably approximately equal to the rate of SPICE-activated cleavage, or even greater.

The ability of an agent to bind heparin may be assessed by ELISA assay or by flowing the agent through a heparin column and collecting and analyzing unbound material for presence of the agent (where a diminished amount of the agent indicates that the agent has bound to heparin in the column) Methods for assessing the ability of an agent to bind to cells, e.g., endothelial cells, include flow cytometry (Smith, 2000). Chemotaxis inhibition by an agent or cellular uptake of an agent can be measured using well established chemotaxis or uptake assays. In any of the above methods, the agent may be tested at a range of different dilutions. In certain embodiments of the invention a PVCCP or PVCCP fragment or variant displays one or more of these activities at a level up to 10-fold lower than that of VCP or SPICE, more preferably up to 5-fold lower than that of VCP or SPICE, more preferably at approximately the same level as that of VCP or SPICE, or at an even greater level.

Virus-based assays can also be used. For example, it is known that expression of VCP inhibits antibody-dependent neutralization of vaccinia virus and virus-infected cells, and reduces cellular influx and inflammation. Deletion of the VCP gene reduces pathogenicity. The activity of a VCCP or VCCP fragment or variant can be tested by introducing a virus that expresses the molecule (e.g., a recombinant virus) into appropriate host cells and/or animals and measuring any one or more of these parameters.

The foregoing methods are described in a number of references cited herein (U.S. Pat. No. 5,157,110 or U.S. Pat. No. 6,551,595; Sahu, 1998; Smith, 2000; Rosengard, 2002, etc.). Any of these methods or variants thereof, or others known in the art, can be used.

Targeting VCCPs, VCIPs, or Fragments of Variants Thereof

The invention provides a composition comprising (i) a VCCP, a VCIP, or a complement inhibiting fragment or variant of either; and (ii) a binding moiety that binds to a component present in the eye of a subject at risk of or suffering from an eye disorder characterized by macular degeneration, choroidal neovascularization, retinal neovascularization, or any combination of these, e.g, a macular degeneration related condition, diabetic retinopathy, or retinopathy of prematurity. The composition can be used to treat or prevent any of the foregoing disorders. Preferably the binding moiety and the VCCP, VCIP, or fragment or variant of either, are linked. The linkage can be covalent or noncovalent and can be direct or indirect in various embodiments of the invention. The binding moiety can be, for example, an antibody or ligand, as discussed below. According to certain embodiments of the invention the component is a cellular marker. In other embodiments of the invention the component is a drusen constituent. The cellular marker can be any marker that is expressed on or at the surface of a cell, preferably an endothelial cell or retinal pigment epithelial cell. In certain embodiments of the invention the cellular marker is a cell type specific marker. For purposes of brevity, the discussion below refers primarily to VCCPs. However, the invention includes embodiments in which a VCCP fragment or variant or a VCIP or a VCIP fragment or variant is used.

In general, the component can be any molecule present on or at the surface of a cell or noncellular molecular entity. By "on or at the surface of the cell or noncellular molecular entity" is meant that the component is accessible to molecules present in the extracellular environment so that it can be recognized and bound by the moiety. The component may be entirely extracellular. The component may be inserted into the cell membrane. In certain embodiments of the invention the component may be partly or entirely within the membrane, in which case the entity must partially penetrate the membrane to gain access. In general, the component is not located in the cytoplasm of a cell. As long as a sufficient portion of the component is exposed or accessible so that it can be recognized and bound, it will be said to be present on or at the surface. In preferred embodiments of the invention the component is a cellular marker, e.g., a cell type specific marker. Where the target is a molecular entity other than a cell, the component can be any chemical entity present on or at the surface of the molecule that is recognizable by an antibody or ligand.

A number of cellular markers that are expressed on or at the surface of endothelial cells and can be used to target a VCCP to endothelial cells in the eye (e.g., in the choroidal vasculature) are disclosed in U.S. Ser. No. 10/923,940. Tissue factor (TF), a molecule involved in hemostasis, is a preferred marker. Briefly, tissue factor is a cell membrane-bound glycoprotein (MW 46 kDa) and a member of the class 2 cytokine receptor family. It is composed of a hydrophilic extracellular domain, a membrane-spanning hydrophobic domain, and a cytoplasmic tail of 21 residues, including a non-disulfide-linked cysteine. Upon exposure to blood, perivascular cell-bound TF binds to factor VII (FVII), a vitamin K-dependent serine protease. TF is expressed on endothelial cells lining the luminal surface of various forms of pathological neovasculature, including pathological vasculature associated with the exudative (wet) form of age-related macular degeneration and diabetic retinopathy but typically is not expressed (or is expressed at a much lower level) in normal vasculature, thus providing a specific and accessible target. By linking a VCCP or VCIP to factor VII or a derivative thereof, the VCCP is targeted to cells that express TF, e.g., endothelial cells in pathological neovasculature. Integrin alpha(v)beta(3) is another preferred marker.

A number of markers are expressed on or at the surface of retinal pigment epithelial cells. These include, but are not limited to, CD68 antigen (Elner S G, *Exp Eye Res.* 1992 July; 55(1):21-8), claudin (Nishiyama K, et al., *Anat Rec.* 2002 Jul. 1; 267(3):196-203, the protein encoded by the RPE65 gene (Nicoletti A., et al., *Invest Opthalmol Vis Sci.* 1998 March; 39(3):637-44), CD45 and ICAM-1 (Limb, G A, et al., *Curr Eye Res.* 1997 October; 16(10):985-91). See also Chowers, I., et al., Studies on retinal and retinal pigment epithelial gene expression, Novartis Found Symp. 2004; 255:131-45, 145-6, 177-8 for additional examples.

A large number of molecular components have been identified in drusen. Such components are suitable noncellular molecular entities to which a VCCP of the present invention can be targeted. These constituents include $\alpha$1-antichymotrypsin, $\alpha$1-antitrypsin, Alzheimer amyloid $\beta$ peptide, advanced glycation end products, amyloid P component, apolipoproteins B and E, carbohydrate moieties recognized by various lectins, cholesterol esters, clusterin, complement factors, cluster differentiation antigen, complement receptor 1, factor X, heparan sulfate proteoglycan, human leukocyte antigen DR, immunoglobulin light chains, major histocompatibility complex class II antigens, membrane cofactor protein, peroxidized lipids, phospholipids and neutral lipids, tissue inhibitor of matrix metalloproteinases-3, transthyretin, ubiquitin, and vitronectin (Zarbin, M A, *Arch Opthalmol.* 122:598-614, 2004). A number of these components are also found in deposits associated with a variety of different diseases including atherosclerosis.

In certain preferred embodiments of the invention the binding moiety is linked to a VCCP. In other embodiments the binding moiety comprises a portion that binds to another molecule to which a VCCP is attached. Suitable binding moieties include antibodies that specifically bind to a cellular marker or noncellular molecular entity such as a drusen constituent and ligands that specifically bind to a cellular marker or noncellular molecular entity such as a drusen constituent. In general, the linkage between the binding moiety and the VCCP can be covalent or noncovalent and can be direct or indirect in various embodiments of the invention. Similarly, a moiety that binds to a noncellular marker such as a drusen constituent may be linked to a VCCP or to another molecule to which a VCCP is attached.

In those embodiments of the invention in which the binding moiety is an antibody, the antibody may be any immunoglobulin or a derivative thereof which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. Monovalent, bivalent or multivalent antibodies can be used. The antibody may be a chimeric or "humanized" antibody in which, for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Preferably the antibody specifically binds to its target on the cell surface, e.g., to a cell-type specific marker. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture.

In certain embodiments of the invention it is preferable to use F(ab')2 or F(ab') fragments rather than antibodies that contain an Fc portion since the Fc portion may have a pro-inflammatory effect or cause other undesirable effects. However, in certain embodiments of the invention it is preferred to use antibodies comprising an Fc domain. F(ab')$_2$ fragments can be generated, for example, through the use of an Immunopure F(ab')$_2$ Preparation Kit (Pierce) in which the antibodies are digested using immobilized pepsin and purified over an immobilized Protein A column. The digestion conditions (such as temperature and duration) may be optimized by one of ordinary skill in the art to obtain a good yield of F(ab')$_2$. The yield of F(ab')$_2$ resulting from the digestion can be monitored by standard protein gel electrophoresis. F(ab') can be obtained by papain digestion of antibodies, or by reducing the S—S bond in the F(ab')$_2$.

In various embodiments of the invention an appropriate binding moiety to which a VCCP is linked can be any molecule that specifically binds to a target molecule (e.g., polypeptide or a portion thereof such as a carbohydrate moiety), through a mechanism other than an antigen-antibody interaction. Such a binding moiety is referred to as a "ligand". For example, in various embodiments of the invention a ligand can be a polypeptide, peptide, nucleic acid (e.g., DNA or RNA), carbohydrate, lipid or phospholipid, or small molecule (e.g., an organic compound, whether naturally-occurring or artificially created that has relatively low molecular weight and is not a protein, polypeptide, nucleic acid, or lipid, typically with a molecular weight of less than about 1500 g/mol and typically having multiple carbon-carbon bonds).

Ligands may be naturally occurring or synthesized, including molecules whose structure has been invented by man. Examples of ligands include, but are not limited to, hormones, growth factors, or neurotransmitters that bind to particular receptors. For example, Factor VII is a ligand for TF. Exemplary TF binding moieties are FVII, activated FVII (FVIIa), inactive FVIIa, antibodies that bind to tissue factor, engineered polypeptides, aptamers, and small molecules that bind to tissue factor. Inactive FVII or inactive FVIIa is a derivative of FVII or FVIIa that is catalytically inactivated in the active site, e.g., by derivatization with an inhibitor. Many irreversible serine protease inhibitors, which generally form covalent bonds with the protease active site, are known in the art. Examples of suitable inhibitors include peptide halomethyl ketones, e.g., peptide chloromethyl ketones (see, Williams et al., *J. Biol. Chem.* 264:7536-7540, 1989 and U.S. Pat. No. 5,817,788). In some embodiments FVII or FVIIa activity is inhibited by substitution, deletion, and/or insertion of one or more amino acids in FVII. Generally the substitution(s), insertion(s), and/or deletion(s) are made at or adjacent to a catalytic site residue. In certain embodiments, the alteration(s) is a substitution or deletion of Ser344, Asp242, and/or His193. As mentioned above, TF binds to factor VII that is normally present in the blood. Thus according to one embodiment of the invention a VCCP is linked to a TF binding moiety. The binding moiety binds to TF, present on endothelial cells in choroidal neovasculature, thereby providing an increased amount of the VCCP at the cell surface and preventing additional complement activation.

It will also be appreciated that fragments or variants of the above-mentioned polypeptide ligands differing in sequence from their naturally occurring counterparts but retaining the ability to bind to endothelial cells or retinal pigment epithelial cells can also be used. In certain embodiments of the invention a polypeptide ligand contains 5 or fewer amino acid differences, 10 or fewer amino acid differences, 25 or fewer amino acid differences, 50 or fewer amino acid differences, or 100 or fewer amino acid differences with respect to its naturally occurring counterpart. In certain embodiments of the invention the number of amino acid differences between a naturally occurring polypeptide ligand and a fragment or variant thereof for use in the invention is 5% or less, 10% or less, or 25% or less of the total number of amino acids in the naturally occurring polypeptide.

In certain embodiments of the invention a fragment or variant of a naturally occurring polypeptide ligand is at least 70% identical, at least 80% identical, at least 90% identical, at least 95% identical, over an amino acid portion that constitutes at least 10%, at least 20%, at least 30%, at least 40%, at least 50%, at least 60%, at least 70%, at least 80%, or at least 90%, or 100% of the length of the naturally occurring counterpart. For example, variant that exhibits at least 50%, at least 60%, at least 70%, at least 80%, at least 90%, or greater sequence identity, over the relevant portion of the sequence could be used, wherein % identity is determined as described above. The amino acid portion is preferably at least 20 amino acids in length, more preferably at least 50 amino acids in length. Alternately, a fragment or variant can display significant or, preferably, substantial homology to a naturally occurring counterpart. Generally a fragment or variant of a naturally occurring polypeptide ligand possesses sufficient structural similarity to its naturally occurring counterpart that it is recognized by an antibody (e.g., a polyclonal or monoclonal antibody) that recognizes the naturally occurring counterpart. Peptide ligands can be identified using phage display (Arap W, et al, *Nature Medicine* 8(2):121-7, 2002); Zurita A J, et al., *J Control Release,* 91(1-2):183-6, 2003; Pasqualini, R. & Ruoslahti, E. *Nature* 380, 364-366, 1996; Pasqualini, R., et al., *Trends Mol. Med.* 8, 563-571, 2002).

In certain embodiments of the invention the ligand is an aptamer that binds to a cell type specific marker. In general, an aptamer is an oligonucleotide (e.g., DNA or RNA or) that binds to a particular protein. Aptamers are typically derived from an in vitro evolution process called SELEX, and methods for obtaining aptamers specific for a protein of interest are known in the art. See, e.g., Brody E N, Gold L. *J Biotechnol.* 2000 March; 74(1):5-13.

Small molecules can also be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., *Pharm. & Ther.* 86: 201-215, 2000).

In certain embodiments of the invention binding moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the cell binding moiety is not an Fc portion of an immunoglobulin molecule.

Methods for covalently or noncovalently linking a VCCP fragment or variant to a binding moiety are known in the art and are described in U.S. Ser. No. 10/923,940. General methods for conjugation and cross-linking are described in "Cross-Linking", Pierce Chemical Technical Library, available at the Web site having URL www.piercenet.com and originally published in the 1994-95 Pierce Catalog and references cited therein, in Wong S S, *Chemistry of Protein Conjugation and Crosslinking*, CRC Press Publishers, Boca Raton, 1991; and G. T. Hermanson, *Bioconjugate Techniques*, Academic Press, Inc., 1995. See also, Allen, T. M., *Nature Reviews Cancer*, 2, 750-763, 2002, which describes methods of making targeted therapeutic agents. For example, according to certain embodiments of the invention a bifunctional crosslinking reagent is used to couple a VCCP with an antibody or ligand. In general, bifunctional crosslinking reagents contain two reactive groups, thereby providing a means of covalently linking two target groups. The reactive groups in a chemical crosslinking reagent typically belong to various classes including succinimidyl esters, maleimides, pyridyldisulfides, and iodoacetamides. Bifunctional chelating agents may also be used.

Alternately, the VCCP or the VCCP fragment or variant and the moiety can be produced as a fusion protein. Thus the invention provides a fusion protein comprising: (i) a first domain comprising a VCCP or complement inhibiting VCCP fragment or variant; and (ii) a second domain comprising a binding moiety that binds to a cellular marker or noncellular molecular entity present in the eye of a subject suffering from or at risk of a macular degeneration related condition or CNV. The first domain may be at the N or C terminus of the fusion protein. The fusion protein may contain one or more additional domains at either the N or C terminus or between the first and second domains.

Targeted VCCPs can be used for treatment of a number of conditions other than macular degeneration related conditions, diabetic retinopathy, or CNV. For such purposes the binding moiety need not bind to a site in the eye. In general, the binding moiety is selected to target the complement inhibiting protein to any site in the body at which complement inhibition is desired. For example, the compounds can be used to treat atherosclerosis, Alzheimer's disease, CNS injury (including spinal cord injury), transplant rejection, or any other disease in which complement activation plays a role (e.g., certain forms of glomerulonephritis, certain inflammatory conditions), etc. They can be used to prevent complement activation during cardiac bypass surgery or ischemia/reperfusion in myocardial infarction or stroke. Atherosclerotic plaques, organ transplants (e.g., xenotransplants, allotransplants, etc.) may be targeted. The targeted compositions can also be used in vitro, e.g., to treat platelets (which are considered cells for purposes of the invention) or other blood preparations in order to inhibit complement, or to treat organs prior to transplantation. Appropriate binding moieties, e.g., cell binding moieties or moieties that bind to a component in an atherosclerotic plaque, an Alzheimer's disease plaque (e.g., β-amyloid), etc. are used to target the VCCP to the plaque. A Gal (1,3-Gal) epitope on the surface of a transplanted organ can be targeted.

Modifications

VCCPs, VCIPs, VCCP or VCIP fragments or variants, and VCCPs, VCIPs, or VCCP or VCIP fragments or variants linked to a binding moiety can be modified by addition of a molecule such as polyethylene glycol (PEG) or similar molecules to stabilize the compound, reduce its immunogenicity, increase its lifetime in the body, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458 (2002; Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476 (2002; Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. Thus in some embodiments a VCCP, VCIP, or fragment or variant of either is modified with one or more polypeptide or non-polypeptide components, e.g., the VCCP, VCIP, or fragment or variant of either is pegylated or conjugated to another moiety. VCCPs, VCCP fragments and variants, and VCCPs or VCCP fragments or variants can be provided as multimers or as part of a supramolecular complex.

Pharmaceutical Compositions and Delivery Vehicles and Methods

Suitable preparations, e.g., substantially pure preparations of a VCCP, VCIP, or a fragment or variant of either may be combined with pharmaceutically acceptable carriers, diluents, solvents, etc., to produce an appropriate pharmaceutical composition. The invention therefore provides a variety of pharmaceutically acceptable compositions for administration to a subject comprising (i) a VCCP; and (ii) a pharmaceutically acceptable carrier, adjuvant, or vehicle. The invention therefore provides a variety of pharmaceutically acceptable compositions for administration to a subject comprising (i) a complement inhibiting VCCP fragment or variant; and (ii) a pharmaceutically acceptable carrier, adjuvant, or vehicle. The invention further provides a pharmaceutically acceptable composition comprising (i) a VCCP linked to a moiety that binds to a component present on or at the surface of a cell or noncellular molecular entity; and (ii) a pharmaceutically acceptable carrier, adjuvant, or vehicle. The moiety may be an antibody or ligand. The component may be a marker such as a cell type specific marker for RPE or endothelial cells, a drusen constituent, etc. Similar compositions comprising a VCIP or a complement inhibiting fragment or variant thereof are also provided.

In certain embodiments of the invention the pharmaceutical composition detectably inhibits neovascularization in an eye, following administration to a subject. In other words, administration of the compound measurably reduces neovascularization relative to the expected level in the absence of the composition. In certain embodiments of the invention the pharmaceutical composition detectably inhibits inflammation in an eye, following administration to a subject. In other words, administration of the compound measurably reduces inflammation relative to the expected level in the absence of the composition. It is to be understood that the pharmaceutical compositions of the invention, when administered to a subject, are preferably administered for a time and in an amount sufficient to treat or prevent the disease or condition for whose treatment or prevention they are administered.

Further provided are pharmaceutically acceptable compositions comprising a pharmaceutically acceptable derivative (e.g., a prodrug) of any of the compounds of the invention, by which is meant any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also able to detectably inhibit complement, e.g., inhibit complement activation.

In various embodiments of the invention an effective amount of the pharmaceutical composition is administered to a subject by any suitable route of administration including, but not limited to, intravenous, intramuscular, by inhalation, by catheter, intraocularly, orally, rectally, intradermally, by application to the skin, etc.

Inventive compositions may be formulated for delivery by any available route including, but not limited to parenteral, oral, by inhalation to the lungs, nasal, bronchial, ophthalmic, transdermal (topical), transmucosal, rectal, and vaginal routes. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered either locally to the eye or intravenously.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of a compound, can also be incorporated into the compositions.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringability exists.

Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Preferred methods of local administration include, e.g., choroidal injection, transscleral injection or placing a scleral patch, selective arterial catheterization, intraocular administration including transretinal, subconjunctival bulbar, intravitreous injection, suprachoroidal injection, subtenon injection, scleral pocket and scleral cutdown injection, by osmotic pump, etc. The agent can also be alternatively administered intravascularly, such as intravenously (IV) or intraarterially. In choroidal injection and scleral patching, the clinician uses a local approach to the eye after initiation of appropriate anesthesia, including painkillers and ophthalmoplegics. A needle containing the therapeutic compound is directed into the subject's choroid or sclera and inserted under sterile conditions. When the needle is properly positioned the compound is injected into either or both of the choroid or sclera. When using either of these methods, the clinician can choose a sustained release or longer acting formulation. Thus, the procedure can be repeated only every several months or several years, depending on the subject's tolerance of the treatment and response.

Intraocular administration of drugs intended for treatment of macular degeneration and other intraocular conditions is well known in the art. See, e.g., U.S. Pat. Nos. 5,632,984 and 5,770,589. U.S. Pat. No. 6,378,526 provides methods for intrascleral injection of a therapeutic or diagnostic material at a location overlying the retina, which provide a minimally invasive technique for delivering the agent to the posterior segment of the eye.

In certain embodiments of the invention a composition is delivered to the vicinity of the eye, e.g., in close proximity to the posterior segment of the eye. The "vicinity of the eye" refers to locations within the orbit, which is the cavity within the skull in which the eye and its appendages are situated. Typically the compositions would be delivered close to their intended target within the eye, e.g., close to (within several millimeters of) the portion of the sclera that overlies the posterior segment of the eye, or immediately adjacent to the exterior surface of the sclera.

A number of polymeric delivery vehicles for providing controlled release have been used in an ocular context and can be used to administer the compositions of the invention. Various polymers, e.g., biocompatible polymers, which may be biodegradable, can be used. For example, U.S. Pat. No. 6,692,759 describes methods for making an implantable device for providing controlled release of therapeutic agents in the eye. Other useful polymers and delivery systems for ocular administration of a therapeutic agent have been described. The active agent may be released as the polymer degrades. Polymers that have been used for drug delivery include, but are not limited to, poly(lactic-co-glycolic acid), polyanhydrides, ethylene vinyl acetate, polyglycolic acid, chitosan, polyorthoesters, polyethers, polylactic acid, and poly (beta amino esters). Peptides, proteins such as collagen and albumin, and dendrimers (e.g., PAMAM dendrimers) have also been used. Any of these can be used in various embodiments of the invention.

Poly(ortho esters) have been introduced into the eye and demonstrated favorable properties for sustained release ocular drug delivery (Einmahl, S., *Invest. Opthalmol. Vis. Sci.,* 43(5), 2002). Polylactide particles have been used to target an agent to the retina and RPE following intravitreous injection of a suspension of such particles (Bourges, J-L, et al, *Invest. Opthalmol. Vis. Sci.,* 44(8), 2003). A macroscopic implantable device suitable for introduction into the posterior or anterior segment of the eye is referred to herein as an ocular implant (Jaffe, G., *Invest. Opthalmol. Vis. Sci.,* 41(11), 2000; Jaffe, G., *Ophthalmology*). Such devices are also referred to as "inserts" in the art. One of skill in the art will appreciate that "ocular insert" encompasses devices designed to be put behind the eyelid, e.g., into the upper or lower formix. The device may be comprised of a plurality of nanoparticles or microparticles impregnated with the agent. Methods for making microparticles and nanoparticles are known in the art. Generally, a microparticle will have a diameter of 500 microns or less, e.g., between 50 and 500 microns, between 20 and 50 microns, between 1 and 20 microns, between 1 and 10 microns, and a nanoparticle will have a diameter of less than 1 micron. Preferably the device is implanted into the space occupied by the vitreous humor. The ocular implant may comprise a polymeric matrix. The invention also provides periocular implants, which are macroscopic implantable device suitable for introduction in the vicinity of the eye, e.g., in close proximity to the eye. In certain embodiments the periocular implant is made of similar materials to those described above.

As mentioned above, cells that express a VCCP, VCIP, or fragment or variant of either, can be implanted into the eye. U.S. Pat. No. 6,436,427 provides a method for delivering biologically active molecules to the eye by implanting biocompatible capsules containing a cellular source of the biologically active molecule.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the agents described above, in certain embodiments of the invention, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (Hansen C B, et al., *Biochim Biophys Acta.* 1239(2):133-44, 1995; Torchilin V P, et al., *Biochim Biophys Acta,* 1511(2): 397-411, 2001; Ishida T, et al., *FEBS Lett.* 460(1):129-33, 1999). One of ordinary skill in the art will appreciate that the materials and methods selected for preparation of a controlled release formulation, implant, etc., should be such as to retain activity of the compound. For example, it may be desirable to avoid excessive heating of polypeptides, which could lead to denaturation and loss of activity.

The invention also encompasses gene therapy, in which a nucleic acid that encodes a VCCP, VCIP, or fragment or variant of either in operable association with regulatory elements sufficient to direct expression of the fragment or variant is introduced into a subject. Nucleic acids can be introduced into a subject by any of a number of methods. For instance, a pharmaceutical preparation of a nucleic acid therapeutic can be introduced systemically, e.g., by intravenous injection. Expression of the polypeptide in particular target cells may result from specificity of transfection provided by the vector, cell-type or tissue-type expression due to the transcriptional regulatory sequences controlling expression of the gene, or a combination thereof. Alternatively, initial delivery of the nucleic acid can be more limited. For example, the vector can be locally introduced into the eye using any of the methods described above for ocular administration.

A pharmaceutical composition comprising a nucleic acid therapeutic of the invention can consist essentially of the nucleic acid or a gene therapy vector comprising in an acceptable diluent, or can comprise a slow release matrix in which the nucleic acid or gene therapy vector is encapsulated or embedded. The gene therapy vector can be a plasmid, virus, or other vector. Alternatively, the pharmaceutical composition can comprise one or more cells which produce a therapeutic nucleic acid or polypeptide such as a VCCP, VCIP, or fragment or variant of either. Preferably such cells secrete the fragment or variant thereof into the extracellular space or bloodstream.

Viral vectors that have been used for gene therapy protocols include, but are not limited to, retroviruses, lentiviruses, other RNA viruses such as poliovirus or Sindbis virus, adenovirus, adeno-associated virus, herpes viruses, SV 40, vaccinia and other DNA viruses. Replication-defective murine retroviral or lentiviral vectors are widely utilized gene transfer vectors. Chemical methods of gene therapy involve carrier-mediated gene transfer through the use of fusogenic lipid vesicles such as liposomes or other vesicles for membrane fusion. A carrier harboring a nucleic acid of interest can be conveniently introduced into the eye or into body fluids or the bloodstream. The carrier can be site specifically directed to the target organ or tissue in the body. Cell or organ-specific DNA-carrying liposomes, for example, can be developed and the foreign nucleic acid carried by the liposome absorbed by those specific cells. Carrier mediated gene transfer may also involve the use of lipid-based compounds which are not liposomes. For example, lipofectins and cytofectins are lipid-based compounds containing positive ions that bind to negatively charged nucleic acids and form a complex that can ferry the nucleic acid across a cell membrane. Cationic polymers are known to spontaneously bind to and condense nucleic acids such as DNA into nanoparticles. For example, naturally occurring proteins, peptides, or derivatives thereof have been used. Synthetic cationic polymers such as polyethylenimine (PEI), polylysine (PLL) etc., are also known to condense DNA and are useful delivery vehicles. Dendrimers can also be used.

Many of the useful polymers contain both chargeable amino groups, to allow for ionic interaction with the negatively charged DNA phosphate, and a degradable region, such as a hydrolyzable ester linkage. Examples of these include poly(alpha-(4-aminobutyl)-L-glycolic acid), network poly(amino ester), and poly (beta-amino esters). These complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid. It has been proposed that such agents may act as a "proton sponge" within the endosome.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The invention further provides pharmaceutical compositions comprising two or more molecular species of the invention, each comprising a moiety that binds to a cellular marker or noncellular molecular entity, wherein the binding moieties in each molecular species bind to a different cellular marker. The invention further provides pharmaceutical compositions comprising one or more molecular species of the invention and an additional active agent. The additional active agent may be an agent that is effective for treatment of a macular degeneration related condition, diabetic retinopathy, CNV and/or ocular inflammation. In certain embodiments of the invention the additional active agent is selected from the group consisting of: angiogenesis inhibitors, antiinflammatory agents, antiangiogenic steroids, and growth factors. Angiogenesis inhibitors are discussed further below. The additional active agent can be an antibiotic or an antiinflammatory agent not necessarily effective specifically for treatment of a macular degeneration related condition, diabetic retinopathy, CNV, or ocular inflammation.

Angiogenesis Inhibitors

Certain embodiments of the present invention make use of one or more angiogenesis inhibitors. Angiogenesis inhibitors can be divided into several groups based on their primary mechanism of action. One group includes cytotoxic agents that damage or kill target cells (e.g., endothelial cells) or that trigger an immune-mediated response that results in damage to or killing of target cells. A second group includes agents that do not substantially damage or kill endothelial cells but instead inhibit their proliferation, migration, capillary tube formation, or other processes associated with angiogenesis. Angiogenesis inhibitors falling into either or both of these groups can be used.

Angiogenesis inhibitors include, but are not limited to, Macugen® or another VEGF nucleic acid ligand; Lucentis®, Avastin®, or another anti-VEGF antibody; combretastatin or a derivative or prodrug thereof such as Combretastatin A4 Prodrug (CA4P); VEGF-Trap; EVIZON™ (squalamine lactate); AG-013958 (Pfizer, Inc.); JSM6427 (Jerini A G); a short interfering RNA (siRNA) that inhibits expression of one or more VEGF isoforms (e.g., $VEGF_{65}$); and an siRNA that inhibits expression of a VEGF receptor (e.g., VEGFR1). Other angiogenesis inhibitors include various endogenous or synthetic peptides such as angiostatin, arresten, canstatin, combstatin, endostatin, thrombospondin, and tumstatin. Other antiangiogenic molecules include thalidomide and its antiangiogenic derivatives such as iMiDs (Bamias A, Dimopoulos M A. Eur J Intern Med. 14(8):459-469, 2003; Bartlett J B, Dredge K, Dalgleish A G. *Nat Rev Cancer.* 4(4):314-22, 2004). β2-glycoprotein 1 (β2-GP1) is an angiogenesis inhibitor of particular interest in the present invention.

Macugen (Pfizer, Eyetech) is a VEGF nucleic acid ligand (also referred to as an aptamer) that binds to and inhibits $VEGF_{165}$ (U.S. Pat. No. 6,051,698). Lucentis (Genentech) is a humanized antibody fragment that binds and inhibits Vascular Endothelial Growth Factor A (VEGF-A). (Gaudreault, J., et al., *Invest Opthalmol. Vis. Sci.* 46, 726-733 (2005) and references therein. Avastin (Genentech) is a full length humanized antibody that also binds to VEGF. Cand5 (Acuity Pharmaceuticals, Philadelphia, Pa.) is a short interfering RNA (siRNA) designed to inhibit expression of VEGF. sima-027 (Sima Therapeutics; Boulder Colo.) is a chemically modified siRNA designed to inhibit expression of the VEGF receptor known as VEGFR1.

β2-GP1, also known as apolipoprotein H, (apoH) (GenBank entry for the complete human β2 glycoprotein 1 is NP_000033), is an abundant plasma glycoprotein that circulates either as a free protein or associated with lipoproteins. (Polz et al., FEBS Letters 102:183-186, 1979; Wurm, H., Int. J. Biochem. 16:511-515, 1984). It is a ~54-kDa single-chain glycoprotein consisting of 326 amino acids. β2-GP1 and methods for its production are further described in U.S. Pub. No. 20030219406. As used herein, the term β2-GP1 is used to refer to both the intact form of β2-GP1 and the nicked form of β2-GP 1. Nicked β2-GP1 is a β2-GP1 polypeptide that is cleaved at Lys 317/Thr 318. In a preferred embodiment, the portions of nicked β2-GP1 remain linked by disulfide bond(s). As used herein, the term β2-GP1 polypeptide includes β2-GP1 having a sequence identical to the native human form (SEQ ID NO: 13) and variants and fragments thereof. The amino acid sequence of β2-GP1 varies between species, and such variations fall within the scope of the term "β2-GP1". In certain embodiments of the invention a variant or fragment has significant or substantial sequence homology to native human β2-GP1. In specific embodiments a β2-GP1 polypeptide is at least 80% identical to SEQ ID NO: 13, or at least 90% identical to SEQ ID NO: 13 over at least 80%, at least 90%, or approximately 100%, e.g., 100%, of SEQ ID NO: 13. In some embodiments a fragment lacks one or more of domains I-V of SEQ ID NO: 13.

Compositions Comprising a VCCP or VCIP and a Gel-Forming Material

The invention provides a variety of compositions comprising a soluble gel-forming and a therapeutic agent, wherein said therapeutic agent is effective for treating an eye disorder characterized by macular degeneration, CNV, RNV, or any combination of these. In various embodiments of the invention the therapeutic agent is a VCCP or VCIP, or a complement inhibiting fragment or variant of either. The composition may comprise one or more additional therapeutic agents effective for treating the eye disorder. Suitable agents are described elsewhere herein.

The invention encompasses the recognition that compositions comprising a soluble gel-forming material are of particular use for the delivery of biological macromolecules such as polypeptides, polynucleotides, or carbohydrates to the posterior segment of the eye. Certain embodiments of the invention therefore provide a uniquely favorable system for delivery of macromolecules such as polypeptides or polynucleotides to the posterior segment of the eye for treatment of eye disorders. The gel-forming material is initially at least partially soluble but is capable of forming a gel under appropriate conditions. The system is designed to localize biological macromolecules in sufficient concentration to provide sustained delivery while at the same time allowing the macromolecule to be released in sufficient amounts so that it can diffuse to a site of action in the posterior segment of the eye, e.g., the retina, RPE, subretinal space, Bruch's membrane, and/or choriocapillaris. In addition, the gel may protect the biological macromolecule from degradation, e.g., by endogenous proteases or nucleases.

A variety of biological macromolecules useful for the treatment of eye disorders characterized by macular degeneration, CNV, RNV, ocular inflammation, or any combination of the foregoing, can be delivered using the gel-forming compositions of the invention. Any of the agents mentioned herein, e.g., angiogenesis inhibitors such as Macugen, Lucentis, β2-GP1, etc., can be delivered either singly or in combination with one or more other agents. The compositions can also be used to deliver agents that are not biological macromolecules. The invention therefore provides a composition comprising: (i) a therapeutic agent effective for the treatment of an eye disorder characterized by macular degeneration, CNV, RNV, ocular inflammation, or any combination of the foregoing; and (ii) a soluble gel-forming material. In certain embodiments of the invention the agent is a complement inhibitor, e.g., a VCCP or VCIP. The complement inhibitor may, but need not be, a polypeptide or peptide.

In accordance with certain embodiments of the invention, a solution containing the gel-forming material and a therapeutic agent is prepared by combining the gel-forming material and therapeutic agent in solution using any suitable method, e.g., by adding the therapeutic agent to a solution containing the gel-forming material. In certain embodiments the composition forms a gel following introduction into the body, e.g., upon contact with a physiological fluid. The composition can also form a gel upon contact with a fluid such as phosphate buffered saline, or other fluid containing appropriate ions. Thus the composition can be injected at an appropriate location, e.g., in close proximity to the posterior segment of the eye, where it forms a gel. Alternately, a preshaped gel implant can be made, e.g., by introducing the solution into a mold or cavity of the desired shape and allowing gel formation to occur in the presence of a suitable concentration of a salt. The salt can be added either prior to or following the introduction of the solution into the mold or cavity. The mold or cavity can be, e.g., any structure that contains a hollow space or concave depression into which a solution can be introduced. In another embodiment, a film or membrane is formed from the gel-forming solution containing a therapeutic agent.

Release of the agent from the gel can occur by any mechanism, e.g., by diffusion of the agent out of the gel, as a result of breakdown of the gel, or both. In certain embodiments of the invention the gel-forming material also comprises at least some solid material in addition to soluble material.

A variety of different gel-forming materials can be used in the present invention. Preferably the gel is a hydrogel, by which is meant a gel that contains a substantial amount of water. Preferably the material and the gel that it forms are biocompatible. Preferably the material and the gel that it forms are biodegradable.

In certain embodiments of the invention soluble collagen is used as the gel-forming material. The invention encompasses the recognition that gel-forming compositions comprising a soluble collagen are particularly advantageous for the delivery of biological macromolecules such as polypeptides, polynucleotides, or carbohydrates to the posterior segment of the eye. The collagen is initially soluble, e.g., in an aqueous medium, and forms a solution that has a low viscosity but is capable of rapid formation of a gel under appropriate conditions, e.g., conditions encountered upon administration to a mammalian subject. In accordance with certain embodiments of the invention, a solution containing the soluble collagen and a therapeutic agent is prepared by combining the soluble collagen and therapeutic agent in solution using any suitable method, e.g., by adding the therapeutic agent to a solution containing soluble collagen. The composition is delivered locally to an appropriate location in or near the eye of a mammalian subject, typically to an area outside of and in close proximity to the posterior segment of the eye. The solution rapidly forms a gel at or close to of the site of administration. The therapeutic agent is entrapped within the gel. The therapeutic agent diffuses out of the gel or is released as the gel degrades over time, thereby providing a continuous supply of the agent to tissues and structures that are either in direct physical contact with the gel or located nearby. In certain embodiments the solution is administered behind the sclera of the eye, as discussed further below. Delivery can be accomplished by injection (e.g., using a 30 gauge needle or the like), by catheter, etc., as further described below.

A variety of different collagen preparations can be used in the present invention provided that the collagen is initially soluble and is capable of rapidly forming a gel under appropriate conditions. Suitable collagen preparations, and methods for their manufacture, are described, e.g., in U.S. Pat. Nos. 5,492,135; 5,861,486; 6,197,934; 6,204,365; and WO 00/47130, but the invention is not limited to such preparations or methods. These collagens are prepared in soluble form and rapidly form a gel upon exposure to physiological fluids or other fluids having suitable concentration of ions. In accordance with the present invention, injecting or otherwise introducing the collagen solution to the eye or near the eye results in gel formation, presumably induced by contact with physiological fluids. However it is noted that the invention is in no way limited by the mechanism by which gel formation occurs. In addition, as noted above, the gel can be formed in vitro and then implanted at an appropriate location, e.g., in close proximity to the posterior segment of the eye.

One suitable method of preparing a soluble collagen solution involves extracting collagen from a natural source, acid solubilizing the collagen, and dialyzing the solubilized collagen against a solution containing a chelating agent, e.g., a metal chelating agent such as ethylenediamine tetraacetic acid, disodium salt dihydrate (EDTA), while raising the pH. One or more dialysis steps against a solution such as deionized water lacking the chelating agent may also be performed. Unlike standard collagen solutions that undergo spontaneous fibrillogenesis at neutral pH and room temperature, collagen solutions for use in the present invention remain in solution during storage for extended periods of time and rapidly undergo gel formation when exposed to physiological fluids. While not wishing to be bound by any theory, the chelating agent may alter the concentration of one or more cations and thereby prevent fibrillogenesis that would otherwise occur as the pH is raised. The chelating agent may have other desirable effects on the collagen solution, and in certain embodiments of the invention the collagen solution comprises a chelating agent, e.g., EDTA. The chelating agent may remain in the collagen solution following dialysis or may be added to the collagen solution. The concentration of the chelating agent may range, for example, between about 0.02M and about 0.05M, e.g., between about 0.025M and about 0.035M. Other chelating agents may also be used including, but not limited to, those described in U.S. Pat. No. 5,861,486.

In certain embodiments the collagen solution has a concentration of soluble collagen ranging between 1 mg/ml and 100 mg/ml, e.g., between 10 mg/ml and 70 mg/ml, between 20 mg/ml and 50 mg/ml, e.g., 30 mg/ml, etc. In certain embodiments of the invention the pH of the collagen solution is between 6.0 and 8.0, e.g., between 6.5 and 7.5, e.g., 7.0.

In certain embodiments of the invention the collagen composition further comprises a fibrillar component comprising collagen solids, e.g., fibrillar collagen solids. One aspect of the invention is the selection of suitable concentrations of soluble collagen and collagen solids that result in a gel that retains the agent within the gel so as to provide sustained delivery for a desired period of time while also permitting release of the agent from the gel in sufficient concentration to be effective at its site of action in the posterior segment of the eye. For example, certain collagen compositions contain between 0.5 mg/ml and 30 mg/ml fibrillar collagen solids, or between 1 mg/ml and 20 mg/ml fibrillar collagen solids, e.g., 2 mg/ml, 3 mg/ml, 4 mg/ml, 5 mg/ml, 6 mg/ml, 8 mg/ml, 10 mg/ml, etc. In terms of percent fibrillar collagen solids on a weight/volume basis, certain collagen compositions contain between 0.05 and 3% fibrillar collagen solids or between 0.1 and 2% fibrillar collagen solids, e.g., 0.2%, 0.3%, 0.4%, 0.5%, 0.6%, 0.8%, 1%, 1.2%, etc. Any suitable fibrillar component can be used in the collagen compositions of the invention. Fibrillar collagen solids can be prepared using a variety of methods. For example, fibrillar collagen may be reconstituted collagen prepared from animal sources such as bovine hide (Frontiers in Matrix Biology, Vol. 10, pp. 1-58, in *Methods of Connective Tissue Research*, Eds. Robert, Moczar, and Moczar, S. Karger, Basel, 1985). Fibrillar collagen may be prepared from human or animal sources as described in U.S. Pat. Nos. 4,969,912 and 5,322,802. The fibrillar collagen solids are suspended in solution at a concentration typically ranging from about 10-100 mg/ml. The collagen suspension containing fibrillar collagen solids is combined with, e.g., added to, a soluble collagen composition either prior to or following addition of the therapeutic agent to a solution comprising soluble collagen.

Without wishing to be bound by any theory, the presence of fibrillar collagen solids may have any of a variety of advantageous effects. By way of non-limiting example, the fibrillar collagen solids may increase the in vivo stability of the collagen gel, e.g., they may decrease the rate of breakdown of the gel. The fibrillar collagen solids may increase the stability of a therapeutic agent contained in the gel and/or decrease or modulate the rate at which the agent is released from the gel by diffusion and/or breakdown of the gel.

In some embodiments of the invention the soluble collagen preparation comprises a chemical cross-linking agent. The agent may crosslink collagen molecules and/or fibrils to one another and/or may crosslink a therapeutic agent such as a VCCP or VCIP to a collagen molecule or fibril. Typical cross-linking agents crosslink collagen amine groups to one another or to amine, carboxyl, phenol, sulfonyl, or carbohydrate groups of therapeutic agents. Suitable cross-linking agents include, but are not limited to, those described in WO 00/47130. Without wishing to be bound by any theory, cross-linking may stabilize the collagen gel (e.g., decrease its rate of breakdown) and/or decrease the rate of release of the therapeutic agent from the gel.

The collagen preparations preferably form a gel within 5 minutes (300 seconds) following contact with physiological fluids. More preferably the collagen preparations form a gel within 90 seconds, 2 minutes (120 seconds) or within 3 minutes (180 seconds) following contact with physiological fluids. Preparations that form a gel within shorter time periods, e.g., within 5-90 seconds, or longer time periods, e.g., 3-5 minutes, can also be used.

Any of collagen types I-XXVIII, or mixtures thereof, can be used in the present invention. The collagen can be purified from natural sources (e.g., human tissue or animal tissue such as bovine, rabbit, etc.) as described in the above-referenced patents and publications. Alternatively, the collagen can be manufactured using recombinant DNA techniques, in which case the sequence can be of human or animal origin. See, e.g., U.S. Pat. Nos. 5,593,854 and 5,667,839. Methods for the production of proteins, e.g., a polypeptide of interest such as a collagen chain, using recombinant DNA technology are well known in the art. Suitable methods include those described above. The term "collagen" includes collagen fragments. Thus in certain embodiments the soluble collagen comprises or consists of a collagen fragment or combination of fragments. In certain embodiments a complete collagen polypeptide chain is used.

A variety of modified or derivatized collagens are also of use in various embodiments of the invention. See, e.g., U.S. Pat. No. 5,201,764. For example, collagen can be acylated with one or more acylating agents such as glutaric anhydride, succinic anhydride, and maleic anhydride and at least one other acylating agent selected from the group consisting of methacrylic anhydride, beta-styrene sulfonyl chloride, ethylene-maleic anhydride copolymer, styrene-maleic anhydride copolymer or poly(vinyl) sulfonic acid.

Other gel-forming materials of use in the invention include, but are not limited to, hyaluronic acid and modified forms thereof, polysaccharides such as alginate and modified forms thereof, self-assembling peptides, etc. See, e.g., U.S. Pat. No. 6,129,761 for further description of alginate and modified forms thereof, hyaluronic acid and modified forms thereof, and additional examples of soluble gel-forming materials that are of use in various embodiments of the present invention. As described therein, other polymeric hydrogel precursors include polyethylene oxide-polypropylene glycol block copolymers such as Pluronics™ or Tetronics™ which are crosslinked by hydrogen bonding and/or by a temperature change, as described in Steinleitner et al., *Obstetrics & Gynecology*, 77:48-52 (1991); and Steinleitner et al., *Fertility and Sterility*, 57:305-308 (1992). Other materials which may be utilized include proteins such as fibrin or gelatin. Polymer mixtures also may be utilized. For example, a mixture of polyethylene oxide and polyacrylic acid which gels by hydrogen bonding upon mixing may be utilized.

Typically a gel-forming material of use in the invention is capable of being at least partly dissolved, or in certain embodiments of the invention substantially or fully dissolved, e.g., in an aqueous medium. For example, at least 50%, at least 60%, at least 70%, at least 80%, at least 90%, at least 95%, or more, by weight, of the gel-forming material present in a gel-forming composition may be dissolved. In certain embodiments essentially 100% of the material is dissolved.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., *ASAID Trans.*, 38:154-157 (1992).

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. In some embodiments a self-assembling peptide, such as those described in U.S. Pat. No. 6,800,481 is used. These peptides self-assemble to form a hydrogel structure upon contact with monovalent cations, e.g., such as those present in extracellular fluid.

In embodiments of the invention in which the gel is formed by cross-linking polymer chains to one another, the composition can include an appropriate cross-linking agent, which is selected according to the particular polymer. Alternately, the cross-linking agent can be administered after administration of the composition containing the gel-forming material, at substantially the same location. Any of these gels can be formed in vitro, e.g., as described above for gels, and implanted at an appropriate location in the eye or in the vicinity of the eye.

In certain embodiments of the invention the composition contains cells that produce and secrete a VCCP or VCIP or fragment or variant of either instead of, or in addition to, containing the VCCP or VCIP or fragment or variant itself. In these embodiments, the gel may be resistant to degradation, so that it traps the cells therein for a sustained period of time.

Figure 1B:
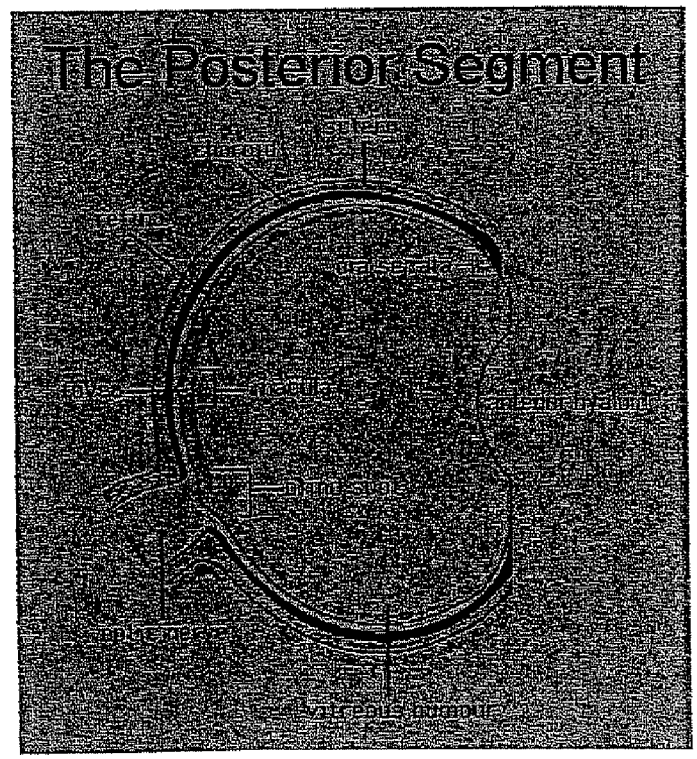
Figure 1C:
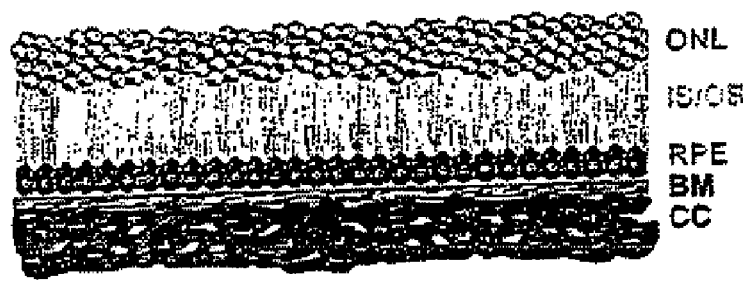
Figure 1D:
Figure 1E:
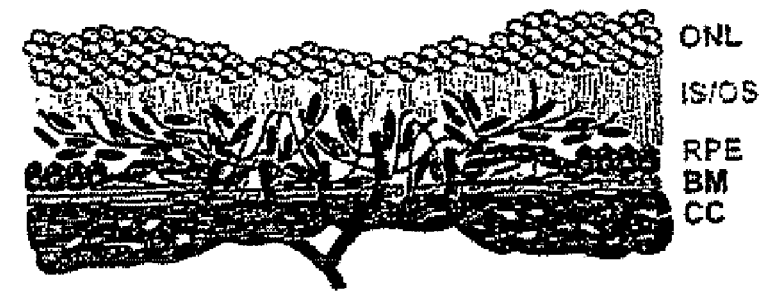

Methods of Administration, Dose, and Dosing Regimens for a Composition Comprising a Gel-Forming Material Any suitable method may be used to administer the gel-forming compositions of the invention to a location in or near the posterior segment of the eye. As shown in FIGS. 1A and 1B, the eye can be divided into an anterior segment and a posterior segment. The sclera, which is a thin, avascular layer of tissue, covers the outside of the eye around the posterior segment and part of the anterior segment and is continuous with the cornea, the transparent covering of the front of the eye. The choroid and retina underlie the sclera. The optic nerve transmits nerve impulses from the retina along the visual pathways.

The composition may be administered by a periocular approach, which term is used to refer to any route of administration that locally delivers a composition into the region outside the eye, i.e., exterior to the sclera. The composition is thus delivered to an area outside of and in close proximity to the posterior segment of the eye. In certain embodiments a composition administered in close proximity to the posterior segment of the eye is administered such that at least one edge or surface of the gel is within 10 mm of at least one point on the exterior surface of the portion of the sclera that covers the outside of the posterior segment of the eye. Preferably at least one edge or surface of the gel is within 5 mm of at least one point on the exterior surface of the portion of the sclera that covers the outside of the posterior segment of the eye. In certain embodiments at least one edge or surface of the gel is within 1-2 mm of at least one point on the exterior surface of the portion of the sclera that covers the outside of the posterior segment of the eye, or within 1 mm or less of at least one point on the exterior surface of the portion of the sclera that covers the outside of the posterior segment of the eye.

Periocular administration may be accomplished using, e.g., retrobulbar, peribulbar, sub-Tenon, or subconjunctival injection, by subretinal injection, by suprachoroidal injection, or by use of a catheter or cannula directed to any of the regions accessed by the afore-mentioned techniques. Most commonly a syringe is used, but a pump or any other source of pressure could also be used. In certain preferred embodiments of the invention the composition is administered adjacent to the sclera, outside the eye, e.g., by retrobulbar, sub-Tenon, or subconjunctival injection. At least one surface of the gel may be in direct contact with the sclera. Methods suitable for administration of local anesthesia for ophthalmic surgery are of use to deliver a composition of the invention. See, e.g., Dutton, J J, et al., "Anesthesia for intraocular surgery", *Surv Opthalmol.* 46(2):172-84, 2001; Canavan, K. S., et al., "Sub-Tenon's administration of local anaesthetic: a review of the technique", *British Journal of Anaesthesia*, 90(6), 787-793, 2003. See also, Spaeth, supra, and Albert and Lucarelli, supra. Compositions delivered according to these standard techniques are considered to be delivered in close proximity to the posterior segment of the eye. The composition forms a gel which, in certain embodiments of the invention at least partially overlies the macula. In certain embodiments of the invention the composition is administered into the sclera itself, e.g., by injection or using a catheter or cannula (see, e.g., U.S. Pat. No. 6,378,526). The therapeutic agent is released from the composition and diffuses from its site of release across the sclera and into the eye, where it reaches a site of activity at the retina. Alternately, a gel structure formed in vitro can be implanted in or in the vicinity of the eye.

The amount and concentration of the therapeutic agent(s) in a composition comprising a gel-forming material can vary depending on a number of factors including, but not limited to, the identity of the therapeutic agent(s), the condition being treated and its severity, the presence or absence of solids and/or chemical cross-linking agents in the composition, the total amount of composition administered (which itself can vary based on various considerations such as the anatomy of the patient, etc.) For example, in the case of a composition comprising soluble collagen, the amount and concentration may vary depending upon the amount of fibrillar collagen in the composition. It may be desirable to employ a concentration and/or total amount of therapeutic agent(s) that will maximize the total amount of agent delivered to the eye, while keeping the concentration actually released from the gel below that which could cause unacceptable side effects. In certain embodiments of the invention the total amount and concentration of the agent(s) are selected to provide an effective concentration of the agent at the retina over a period of at least 4 weeks, e.g., 4-6 weeks, 6 weeks or greater, 8 weeks or greater, etc.

The dosing interval (i.e., the time between individual administrations of an inventive composition) and the dose of the therapeutic agent delivered with each administration can vary. In certain embodiments the composition is delivered at times more than 6 weeks apart, e.g., 2, 3, 4, 5, or 6 months apart, or any intervening number of weeks, e.g., 8, 10, 12, 14, 16 weeks, etc. In other embodiments the composition is delivered at even greater time intervals, e.g., at times 7, 8, 9, 10, 11, or 12 months apart. In other embodiments the time interval is 6 weeks or less. Of course the time interval can vary. For example, the time intervals between doses can alternate between 6 weeks or less and more than 6 weeks. In certain embodiments the average time interval between administrations of an inventive composition is at least 6 weeks, e.g., 2, 3, 4, 5, or 6 months, or any intervening number of weeks, e.g., 8, 10, 12, 14, 16 weeks, etc. In certain embodiments of the invention the composition is administered multiple times at time intervals on average at least 6 weeks apart, at least 8 weeks apart, at least 10 weeks apart, at least 12 weeks apart, etc. Typically the composition is administered at least 2, 5, 10, 20, 50, or more times. The composition can and often will be administered indefinitely to a subject suffering from or at risk of a macular degeneration related condition, CNV, RNV, ocular inflammation, etc.

The total amount of therapeutic agent and its concentration in the gel can also vary. Exemplary, nonlimiting, doses are between approximately 0.1 and 100 mg/dose for each eye to be treated, e.g., between approximately 0.5 and 50 mg/dose, between 1 and 10 mg/dose, etc. Exemplary, nonlimiting concentrations of a therapeutic agent in a composition of the invention are between approximately 0.1 and 100 mg of the therapeutic agent per milliliter of collagen solution, e.g., the concentration may be between 1 and 50 mg/ml, between 1 and 10 mg/ml, etc.

In some embodiments a dose of a first therapeutic agent such as a VCCP or VCIP is administered intravitreally, and a composition of the invention comprising a second therapeutic agent, which can be the same as or different to the first therapeutic agent, is administered to the subject using a periocular administration technique, with the two administrations occurring within a reasonably narrow period of time, e.g., within up to about 6 weeks of one another. The intravitreal administration may provide an initial high concentration of the therapeutic agent at the retina. The periocular administration then provides a sustained release of the therapeutic agent over time.

Testing Therapeutic Potential in Animal Models

A number of different animal models that attempt to replicate one or more features of macular degeneration, diabetic retinopathy, choroidal neovascularization, and/or ocular inflammation are known in the art. A compound of the invention can be administered in various doses to mice, rats, dogs, primates, etc. that have either spontaneous or macular degeneration and/or choroidal neovascularization or in which macular degeneration and/or choroidal neovascularization have been induced by a treatment. The ability of the compound to prevent or treat one or more signs or symptoms of macular degeneration (e.g. CNV, accumulation of lipofuscin in and/or drusen beneath the RPE, photoreceptor atrophy or hypertrophy, altered RPE pigmentation, photoreceptor loss, altered electroretinogram, etc.) is assessed. Visual examination, photography, histopathology, immunohistology, etc., can be used.

Useful models include animals (e.g., mice, Yucatan pigs, etc.) in which choroidal neovascularization is induced by laser treatment (Bora, P. S., et al., *Proc. Natl. Acad. Sci.* 100(5): 2679-2684, 2003; Zacks, D N, et al., *Invest Opthalmol Vis Sci.* 243(7):2384-91, 2002). Other models include animals that have been treated with a variety of agents such as lipid hydroperoxide (Tamai, K., et al., *Exp Eye Res.* 74(2): 301-8, 2002), pellets comprising growth factors, etc. Animals genetically engineered to overexpress or underexpress one or more genes are also useful. For example, transgenic mice (mcd/mcd mice) that express a mutated form of cathepsin D that is enzymatically inactive display features associated with geographic atrophy (Rakoczy, P E, et al, *Am. J. Path.*, 161(4), 1515-1524, 2002). Adeno-associated virus (AAV) mediated expression of vascular endothelial growth factor induces choroidal neovascularization in rats (Wang, F., et al., *Invest Opthalmol Vis Sci.* 44(2):781-90, 2003). One animal model is a transgenic mouse deficient in either monocyte chemoattractant protein (Ccl-2) or its cognate chemokine receptor (Ccr-2) (Ambati, J., et al., *Nat. Med.* 9(11):1390-7, 2003; U.S. Ser. No. 10/685,705—U.S. publication 20040177387). Aged mice with a deficiency in either of these proteins exhibit a number of features of ARMD including accumulation of lipofuscin in and drusen beneath the RPE, photoreceptor atrophy, and CNV. Methods for testing the efficacy of a candidate agent using this mouse model are disclosed in U.S. publication no. 20040177387. In general, a candidate agent is administered to the mouse either before or after development of features of ARMD, and at least one eye is monitored for development or regression of drusen and/or lipofuscin accumulation therein, for affect of the candidate agent on Bruch's membrane, affect on retinal degeneration, and/or for affect on choroidal neovascularization.

The candidate agent can be administered systemically or locally. The agent can be delivered orally, intravenously, intraperitoneally, intravitreously, transsclerally or topically. The agent can be delivered by intravitreal injection, transclerally, by sustained release implant, etc. The eye can be analyzed by ophthalmoscopy, angiography, histopathology or a combination thereof. Any of these methods can be used to assess efficacy of a candidate agent in any animal model. Models also exist for diabetic retinopathy.

Animal models for ocular inflammation are also known in the art. For example, experimental allergic uveitis is a well-known model system (Singh, V K., et al., *Indian J Med Res.*, 107:53-67, 1998). Endotoxin-induced uveitis is another useful model (Kozhich, A. T., et al., *Investigative Ophthalmology and Visual Science,* 41:1823-1826, 2000.)

The examples discussed herein are but a few of the model systems in which efficacy of the compounds of the invention can be assessed.

Compounds that show promising results in animal studies are tested in humans, e.g., using standard protocols and endpoints for clinical trials for therapies for ARMD or diabetic retinopathy.

Identifying Subjects and Assessing Response

The methods of the invention may include providing a subject to which a composition of the invention is to be administered. The subject is typically at risk of or suffering from an eye disorder characterized by macular degeneration, choroidal neovascularization, retinal neovascularization, or any combination of these. The composition is administered to the subject with the intent of treating or preventing such condition. Thus the subject will typically have been identified as being at risk of or suffering from such a condition. Methods for diagnosis of macular degeneration and choroidal neovascularization and for assessing response to therapy are known in the art. Any suitable tests and criteria can be used to identify a subject at risk of or suffering from a macular degeneration related condition, diabetic retinopathy, or choroidal neovascularization and/or to measure a response to therapy. Visual acuity can be measured using, for example, a Snellen chart, a Bailey-Lovie chart, a decimal progression chart, a Freiburg visual acuity test, a measurement of minimum angle of resolution (MAR) etc. Metamorphopsia (visual distortion) may be measured using an Amsler chart. Contrast sensitivity may be measured using a Pelli-Robson chart. Diagnostic studies include, but are not limited to, standard ophthalmologic examination of the fundus, stereo biomicroscopic examination of the macula, intravenous fundus fluorescein angiography, fundus photography, indocyanine green video-angiography, and optical coherence tomography. A subject displaying an abnormality on one or more of these diagnostic studies (e.g., a subject that falls outside a range that is considered normal for a healthy eye) may be treated in accordance with the present invention.

Subjects may be classified as having early, intermediate, or advanced ARMD in accordance with the classification scheme used in the Age-Related Eye Diseases Study (AREDS), which is set forth in guidelines developed American Academy of Ophthalmology (American Academy of Ophthalmology, Age Related Macular Degeneration Preferred Practice Pattern™, 2003; available for download at URL www.aao.org/aao/education/library/ppp/amd_new.cfm). A subject falling into any of these categories may be treated in accordance with the present invention. If the subject has already developed CNV, the subject may have classic CNV, occult CNV, or a mixture of the two. Of course alternate classification schemes, of which a variety is described in the literature, could also be used.

ARMD is known to have a genetic component, based on studies showing an increased incidence of ARMD in individuals with relatives suffering from ARMD (e.g., twin studies). Therefore, a subject may be considered at risk of developing ARMD if he or she has one or more close relatives (e.g., parent, grandparent, sibling, cousin, uncle, aunt), who has received a diagnosis of ARMD. Individuals who smoke and/or consume a high fat diet are also at increased risk. The incidence of ARMD increases with age. Therefore, an individual over approximately 50 years of age, generally at least 60 or at least 70 years of age may be considered at increased risk. An individual having drusen and one or more additional risk factors may be at particular risk for developing ARMD. An individual with multiple drusen, particularly if large and with indistinct borders, may be at particular risk. An individual with RPE hyperpigmentation or hypopigmentation or geographic atrophy may be at particular risk. Specific genetic mutations are associated with various less common macular degeneration related conditions. A subject who has received a diagnosis of diabetes is at risk of developing diabetic retinopathy.

Response to therapy can be assessed by any of the methods mentioned above. Numerous studies have been conducted to assess the efficacy of a variety of different therapies in restoring vision, preventing visual loss, and/or resulting in improvement or slowing progression of ARMD or choroidal neovascularization as judged by diagnostic tests such as those described above. One of ordinary skill in the art will be able to select appropriate criteria by which to judge the efficacy of therapy.

In addition to protocols and endpoints that have typically been employed in evaluating therapies for ARMD, the present invention contemplates testing the inventive compositions to establish their utility in inhibiting progression from the dry form of ARMD to the wet form. Accordingly, in some embodiments the compositions are administered to subjects who have been diagnosed with the dry type of ARMD. The ability of the composition to inhibit progression of the dry form of ARMD to wet type ARMD is assessed.

In one example, subjects with the dry type of ARMD are divided into two groups. One group receives a single retrobulbar or sub-Tenon injection of the inventive composition in the vicinity one eye, e.g., in close proximity to the posterior segment of the eye, while the other group either receives either no treatment or a single intravitreal injection of another therapeutic agent such as Macugen or Lucentis into one eye. The groups are monitored over a period of 6 months to 2 years to determine the percentage of subjects that progress to the wet type of ARMD.

In another example, subjects with the dry type of ARMD are divided into two groups. One group receives a single retrobulbar or sub-Tenon injection of the inventive composition in the vicinity of one eye, e.g., in close proximity to the posterior segment of the eye, every 6 months while the other group either receives either no treatment or a single intravitreal injection of another therapeutic agent such as Macugen or Lucentis into one eye every 6 months. The groups are monitored over a period of 1-2 years (or longer) to determine the percentage of subjects that progress to the wet type of ARMD. In another non-limiting example, subjects with dry type ARMD are divided into two groups. One group receives a retrobulbar or sub-Tenon injection of the inventive composition in the vicinity of one eye, e.g., in close proximity to the posterior segment of the eye, every 3-6 months while the other group receives either no treatment or receives treatment with Macugen or Lucentis according to the protocols used for treating wet type ARMD, i.e., intravitreal injection every 4-6 weeks. The groups are monitored for a period of 1-2 years (or longer) to determine the percentage of subjects that progress to the wet form of ARMD.

In another example the ability of an inventive composition to inhibit progression of early ARMD (AREDS 2) to intermediate ARMD (AREDS 3) is assessed. Subjects with early ARMD are divided into two groups, one of which receives an inventive composition as described in either of the two examples above while the other receives either no therapy or an alternative therapy such as Lucentis or Macugen as described in either of the two examples above. The groups are monitored for a period of time (e.g., as described above) to determine the percentage of subjects that progress from early to intermediate ARMD.

In another example the ability of an inventive composition to inhibit progression of intermediate ARMD (AREDS 3) to advanced ARMD (AREDS 4) is assessed. Subjects with intermediate ARMD are divided into two groups, one of which receives an inventive composition as described in either of the two examples above while the other receives either no therapy or an alternative therapy such as Lucentis or Macugen as described in either of the two examples above. The groups are monitored for a period of time (e.g., as described above) to determine the percentage of subjects that progress from intermediate to advanced ARMD.

In addition to monitoring progression of ARMD, the incidence of side effects and complications may also be monitored. Consideration of side effects is an important aspect when evaluating the overall outcome and risk/benefit ratio of a therapy. For example, if two therapies are equally efficacious in terms of inhibiting progression of or treating ARMD, the therapy with a lower incidence of side effects is typically preferred for most subjects. In certain embodiments of the invention therapy of a macular degeneration related condition such as ARMD, or CNV or RNV from any cause, using a composition of the invention is associated with fewer side effects over time (e.g., over a 1-2 year period) than therapy with FDA-approved therapy for ARMD.

Therapeutic Applications

The compositions of the invention can be administered to a subject to treat a macular degeneration related condition (e.g., ARMD), diabetic retinopathy, retinopathy of prematurity, persistent hyperplastic vitreous syndrome, choroidal neovascularization, and/or any condition characterized by ocular inflammation, etc. The subject may have exudative or non-exudative ARMD. In certain embodiments of the invention that subject has exudative ARMD but does not have RAP while in other embodiments the subject does have RAP. In certain embodiments of the invention the subject suffers from ocular inflammation but does not suffer from ARMD, diabetic retinopathy, retinopathy of prematurity, persistent hyperplastic vitreous syndrome, or CNV.

One particularly advantageous use for the compositions and methods of the invention is to inhibit progression of non-exudative ARMD to exudative ARMD or to inhibit progression of non-exudative ARMD to a more severe form. For example, in certain embodiments of the invention an inventive composition inhibits progression of early ARMD (AREDS 2) to intermediate ARMD (AREDS 3) or to advanced ARMD (AREDS 4). In certain embodiments of the invention the composition inhibits progression of intermediate ARMD (AREDS 3) to advanced ARMD (AREDS 4). Any of the compositions of the invention may be used for these purposes in various embodiments of the invention. In a specific embodiment a composition of the invention, e.g., a gel-forming composition of the invention, is used for treating subjects with non-exudative ARMD, e.g., to prevent or inhibit progression to exudative ARMD. In certain embodiments the subject has not developed detectable CNV and the composition prevents or delays the development of CNV. For example, the subject may have dry ARMD, and the composition prevents or delays the onset of wet ARMD. In certain embodiments the subject has developed detectable CNV and the composition slows the rate of progression of CNV and/or causes regression of existing CNV. In certain embodiments the subject has not developed detectable RNV and the composition prevents or delays the development of RNV. In certain embodiments the subject has developed detectable RNV and the composition slows the rate of progression of RNV and/or causes regression of existing RNV. The composition can be administered once or multiple times to a subject who does or does not have a condition such as CNV or RNV (or both), e.g., at approximately predetermined time intervals such as, for example, approximately every 4 weeks, approximately every 6 weeks, approximately every 8, 10, 12, 16, 20, 24 weeks, approximately every 6, 8, 10, or 12 months, etc. It will be understood that in any of the methods of this invention, the composition should be administered in an amount effective to achieve the indicated result, within sound medical judgment. It should also be understood that the result need not be achieved in every instance.

Ancillary therapies may also be used concurrently, prior to, or following treatment using the compositions and methods of the invention. Such therapies include, but are not limited to, administration of antioxidant vitamin and/or mineral therapy, photodynamic therapy (e.g., with verteporfin or other agents), administration of antiinflammatory agents, antiangiogenic therapy (e.g., administration of one or more angiogenesis inhibitors such as anecortave acetate or other angiostatic steroids; anti-VEGF or anti-VEGFR antibody, antibody fragment, siRNA, antisense RNA, or aptamer; or any other antiangiogenic agent including but not limited to a small molecule, siRNA, antisense RNA, or aptamer targeted to any proangiogenic gene), growth factor administration, implantation of cells (e.g., neural stem cells, RPE stems cells, RPE cells) into the eye, laser photocoagulation, radiation therapy, thermal therapy, and surgery (e.g., submacular surgery or macular translocation). In certain embodiments of the invention a growth factor for RPE cells is administered, e.g., REF-1/TFPI-2 (Tanaka, Y, et al., *Invest Opthalmol Vis Sci.* 45(1): 245-52, 2004).

It may be desirable to treat an eye that already suffers from choroidal and/or retinal neovascularization (e.g., in a subject with diabetic retinopathy or ARMD) using photocoagulation or surgery and to also administer a composition of the invention to the subject to preserve vision in the other eye and/or prevent a recurrence of CNV and/or RNV in the eye treated with photocoagulation or surgery.

EXAMPLES

Example 1

Prevention of Choroidal Neovascularization in a Mouse Model by Administration of VCP Recombinant VCP is produced in and purified from a *Pichia pastoris* expression system as described in Sahu, 1998. VCP is dissolved in physiological saline at various concentrations.

Mice (3 groups, N=10 in each group) are anesthetized and their pupils dilated. Krypton red laser photocoagulation is used to generate multiple (e.g., 3-20) laser spots in each eye as described in Bora, 2003. For the first group, various doses of VCP (e.g., 0.01-100 μg) are administered by injection to one eye in each mouse at days 1 and 4 following laser treatment. The other eye serves as a control. For the second group, various doses of VCP (e.g., 0.01-100 mg/kg) are administered intravenously. Mice in the third group serve as a control. In another experiment, various doses of VCP are administered at different time points following laser treatment.3

Mice are sacrificed at various time points, perfused with saline containing fluorescein-labeled dextran (FITC-dextran, Sigma), their eyes enucleated, and scleral-choroidal-RPE flat mounts are prepared and stained with a mAB against elastin (Sigma) and a CY3-conjugated secondary antibody (Sigma) and examined with a confocal microscope and with light microscopy. The CNV stains green, while elastin in Bruch's membrane stains red. The number of CNV-positive laser spots is determined. A reduced number of spots in the treated eyes versus untreated eyes or mice indicates that the recombinant VCP is effective in preventing and/or treating CNV. Flat mounts are also stained for various drusen constituents and lipofuscin. Expression of various drusen constituents and growth factors thought to play a role in CNV is assessed in samples obtained from the eyes by RT-PCR and ELISA assay.

Example 2

Prevention of Choroidal Neovascularization in a Mouse Model by Administration of VCP Materials and Methods Recombinant VCP was produced in and purified from a *Pichia pastoris* expression system as described in Sahu, 1998. VCP was dissolved in physiological saline at various concentrations.

CNV Induction in Mice

C57BL/6 mice (The Jackson Laboratory) were anesthetized with a mixture of ketamine/xylazine (8:1) and the pupils were dilated with a single drop of 1% tropicamide. Krypton red laser photocoagulation (50-μm spot size, 0.05 s duration, 250 mW) will be used to generate laser spots in bothounding the optic nerve by using a hand-held coverslip as a contact lens. Formation of a bubble at the laser spot indicated rupture of Bruch's membrane. Multiple laser spots were generated in each eye.

Injection of VCP in the Eyes of Mice

Mice in which CNV has been previously laser-induced were administered VCP solutions by intravitreal injection. Different groups of mice were injected with different quantities of this molecule or of mouse albumin (as a control) to determine the effect of dosage on the efficacy and toxicity of VCP. Briefly, after anesthesia and dilation of the pupil, the anterior chamber was entered via the limbus with a 28-gauge needle to decompress the eye. Under an operating microscope, which allows visualization of the retina, a 32-gauge (blunt) needle was passed through a scleral incision, just behind the limbus, into the vitreous cavity. A Hamilton syringe was used to inject 1 μl of a solution containing either VCP or albumin.

Determination of Incidence and Size CNV

Seven days after CNV induction incidence of CNV was determined. Briefly, the mice were perfused with a FITC-dextran (Sigma-Aldrich) solution just prior to sacrifice. After the eyes were excised and fixed for 1 h in 10% phosphate-buffered formalin, RPE-choroid-scleral flat mounts were prepared as follows. The cornea and the lens were removed and the neurosensory retina carefully dissected from the eyecup. Five radial cuts were from the edge of the eyecup to the equator; the sclera-choroidretinal pigment epithelium (RPE) complex was flat-mounted, with the sclera facing down, on a glass slide in Aquamount. The flat mounts were stained with an anti-elastin specific monoclonal antibody (Sigma-Aldrich) and then with a CY3-conjugated secondary antibody (Sigma-Aldrich) at a suitable concentration, e.g., at a $\frac{1}{200}$ dilution of a 1.0 mg/ml stock solution. Mounts were observed under confocal microscopy (LSM510, Zeiss). The prominent neovascular growth stained green whereas the underlying elastin in the Bruch's membrane stained red within a laser spot. Images were analyzed with the image analysis software AxioVision (Zeiss). The amount of CNV was determined by measuring the total green-fluorescent surface area in each picture. A mean green-fluorescent area was obtained for the table and the graph, administration of 30 μg VCP caused a statistically significant reduction in the mean area of CNV relative to either no treatment or administration of albumin.

TABLE 2

Effect of VCP on Development of CNV in a Mouse Model
Multiple Comparisons
Dependent Variable: FldAreaGreen
Tamhane

| (I) Group | (J) Group | Mean Difference (I − J) | Std. Error | Sig. | 95% Confidence Interval Lower Bound | 95% Confidence Interval Upper Bound |
|---|---|---|---|---|---|---|
| No-treatment control | No-treatment control | | | | | |
| | Mouse Albumin Control | 1909.00993 | 1090.44317 | .601 | −1325.1110 | 5143.1309 |
| | VCP 10 ug | −666.84488 | 1151.10903 | 1.000 | −4015.6447 | 2681.9549 |
| | VCP 30 ug | 4877.53314* | 848.72770 | .000 | 2345.4558 | 7409.6105 |
| | Compstatin 30 ug | 5194.92113* | 846.05120 | .000 | 2668.9363 | 7720.9060 |
| Mouse Albumin Control | No-treatment control | −1909.00993 | 1090.44317 | .601 | −5143.1309 | 1325.1110 |
| | Mouse Albumin Control | | | | | |
| | VCP 10 ug | −2575.85481 | 1053.13838 | .182 | −5733.0303 | 581.3207 |
| | VCP 30 ug | 2968.52321* | 710.20220 | .013 | 533.9807 | 5403.0657 |
| | Compstatin 30 ug | 3285.91120* | 707.00147 | .006 | 853.1175 | 5718.7049 |
| VCP 10 ug | No-treatment control | 666.84488 | 1151.10903 | 1.000 | −2681.9549 | 4015.6447 |
| | Mouse Albumin Control | 2575.85481 | 1053.13838 | .182 | −581.3207 | 5733.0303 |
| | VCP 10 ug | | | | | |
| | VCP 30 ug | 5544.37802* | 800.23300 | .000 | 3101.1268 | 7987.6293 |
| | Compstatin 30 ug | 5861.76601* | 797.39374 | .000 | 3424.3034 | 8299.2287 |
| VCP 30 ug | No-treatment control | −4877.53314* | 848.72770 | .000 | −7409.6105 | −2345.4558 |
| | Mouse Albumin Control | −2968.52321* | 710.20220 | .013 | −5403.0657 | −533.9807 |
| | VCP 10 ug | −5544.37802* | 800.23300 | .000 | −7987.6293 | −3101.1268 |
| | VCP 30 ug | | | | | |
| | Compstatin 30 ug | 317.38799 | 176.41849 | .574 | −214.1787 | 848.9547 |
| Compstatin 30 ug | No-treatment control | −5194.92113* | 846.05120 | .000 | −7720.9060 | −2668.9363 |
| | Mouse Albumin Control | −3285.91120* | 707.00147 | .006 | −5718.7049 | −853.1175 |
| | VCP 10 ug | −5861.76601* | 797.39374 | .000 | −8299.2287 | −3424.3034 |
| | VCP 30 ug | −317.38799 | 176.41849 | .574 | −848.9547 | 214.1787 |
| | Compstatin 30 ug | | | | | |

*The mean difference is significant at the .05 level.

various groups and compared using student t-test for comparisons between groups and ANOVA for comparison among multiple groups. The number of spots studied was as follows: No treatment control: 35 spots); mouse albumin control: 12 spots; VCP (10 μg): 26 spots; VCP (30 μg): 14 spots. Deposition of a variety of different complement components is also measured using immunological techniques and/or RT-PCR.

Results

Figure 7:
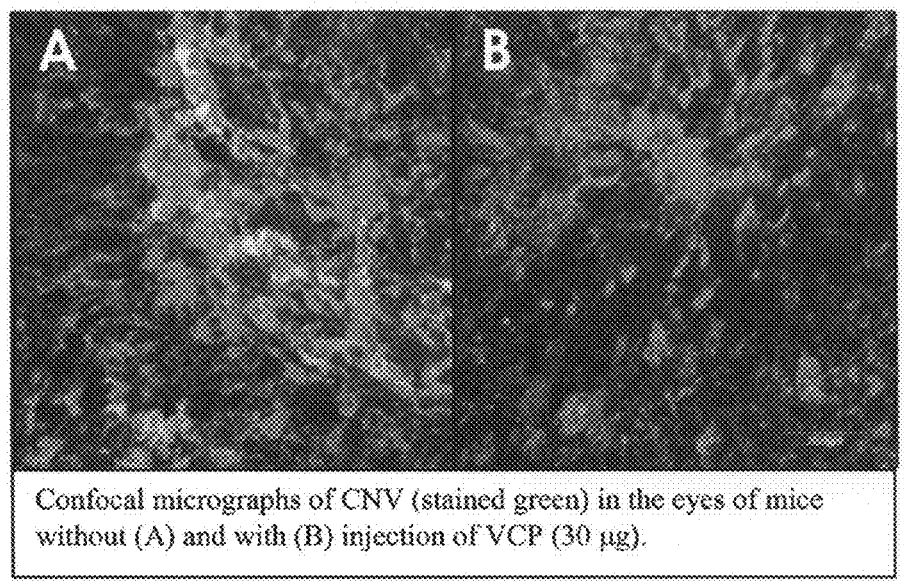
FIG. 7 shows confocal micrographs of CNV (stained green) in the eyes of mice without (A) and with (B) injection of VCP.
Figure 8:
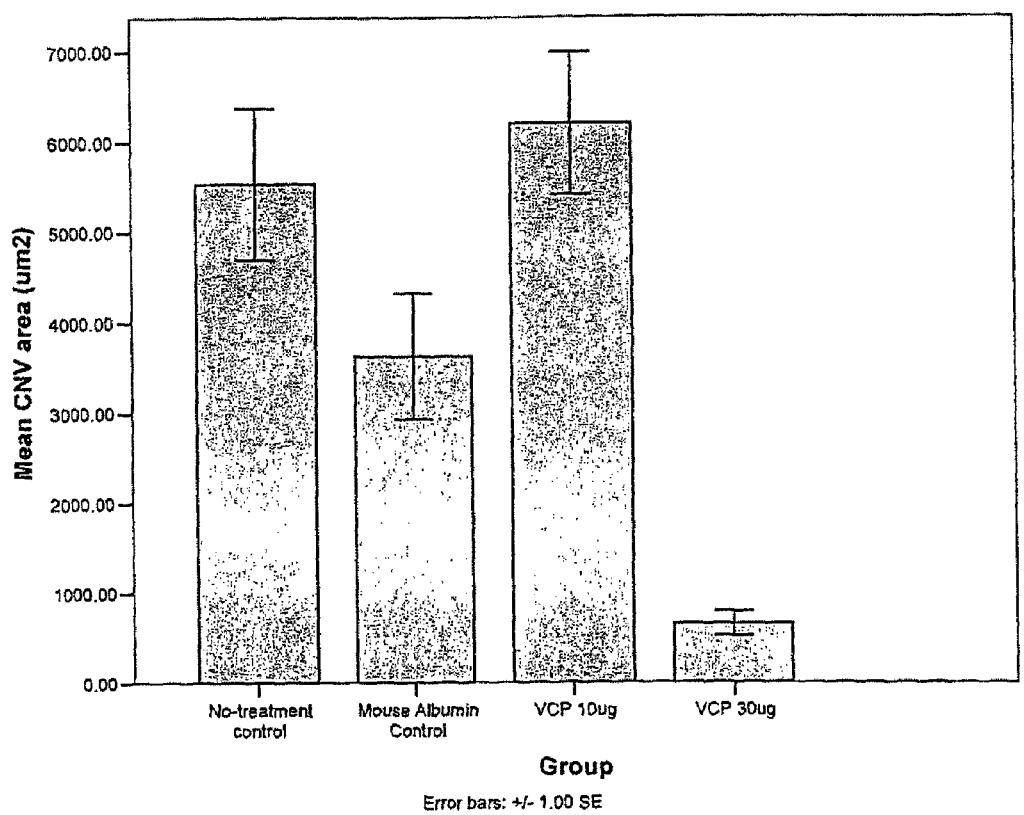
FIG. 8 is a graph showing a comparison of the mean CNV area (in μm$^2$) in mice that received either no treatment or received an intravitreal injection of albumin, or an intravitreal injection of VCP (either 10 μg or 30 μg).

The effects of VCP on the development of CNV was tested in a murine model of laser-induced CNV. Briefly, VCP (either 10 μg/eye or 30 μg/eye) was injected in the vitreous 24 hrs after laser induction. Seven days after CNV induction, incidence of CNV was determined. Just prior to sacrifice, the mice were perfused with a FITC-dextran (Sigma-Aldrich) solution. After the eyes were excised and fixed in 10% phosphate-buffered formalin, RPE-choroid-scleral flat mounts were prepared and stained with an anti-elastin specific monoclonal antibody (Sigma-Aldrich) and then with a CY3-conjugated secondary antibody (Sigma-Aldrich). Mounts were observed under confocal microscopy (LSM510, Zeiss). The prominent neovascular growth stained green whereas the underlying elastin in the Bruch's membrane stained red within a laser spot (FIG. 7). Images were analyzed with the image analysis software AxioVision (Zeiss). The amount of CNV was determined by measuring the total green-fluorescent surface area in each picture. A mean green-fluorescent area was obtained for both groups and compared using student t-test for comparisons between groups and ANOVA for comparison among multiple groups. Results are described in Table 2 and in the graph in FIG. 8. As is evident both from the Example 3

Treatment with SPICE in a Mouse Model of Age Related Macular Degeneration

Expression vectors suitable for expression of recombinant SPICE in mammalian or insect cells are generated, and SPICE is produced in and purified from 293T cells or *Spodoptera frugiperda* cells as described in Rosengard, 2002.

SPICE is administered to 15, 16, or 18 month old normal mice and age-matched mice deficient in Ccl-2 and/or Ccr-2 (Ambati, et al.). Administration is performed by injection to one eye. The other eye serves as a control. In another experiment SPICE is administered intravenously. Various doses (as in Example 1) and treatment regimens are used. For example, in some groups SPICE is injected every 3 days. In other groups SPICE is injected weekly. The mice are sacrificed at various time points and their eyes are processed and analyzed as described in Example 2. The ability of SPICE to prevent, inhibit, and/or treat CNV or other features of ARMD such as photoreceptor atrophy, drusen and lipofuscin accumulation, etc., is assessed.

Example 4

Prevention of Choroidal Neovascularization in a Mouse Model by Administration of SPICE Example 2 is repeated using SPICE instead of VCP. Amounts ranging from 1-30 μg are tested.

Example 5

Preparation of Collagen Solutions for a Gel-Forming Composition

Stock Collagen Preparation.

Collagen for all formulations will be prepared from porcine corium. Split porcine hide will be procured from Lampire Biological Laboratories (Pipersville, Pa.). Split hide will be rinsed with reagent alcohol and placed in frozen storage prior to receipt. Sections of split corium will be cut into small pieces (about 1 cm$^2$) and soaked in reagent alcohol and then washed extensively with sterile water. The washed pieces will be placed in 20 volumes of 0.5M HCl for 30 minutes, washed with sterile water and then placed in 20 volumes of 0.5N NaOH for 30 minutes. Both treatments have been shown to be effective in reducing viral titers by up to 6 logs. In addition, both treatments have been shown to have significant bactericidal effects, reducing bacterial loads by up to 9 logs. The chemically disinfected corium will be washed extensively in sterile water, weighed and placed in 20 volumes (v/w) of 0.5M acetic acid. The pieces will be stirred for 72 hours and porcine mucosal pepsin added to the partially swollen corium.

Pepsin will be added at 2% (w/w wet corium) and stirred for 48 hours. An additional aliquot of pepsin will be added at 1% (w/w wet corium) and stirred for another 24 hours. At this point, the corium should be "dissolved" in acetic acid. Small, undissolved pieces will be removed by filtering the thick slurry through cheesecloth. The filtrate will be diluted with 0.5M acetic acid and dialyzed against 0.5N acetic acid using dialysis tubing having a 50,000 dalton nominal cut-off. An alternate dialysis method will utilize ultrafiltration/diafiltration cartridges procured from Amersham Biotech. The dialysis process removes pepsin and degraded pepsin. The retained liquid containing collagen will be subjected to differential NaCl precipitation to isolate predominantly Type I collagen. Purified Type I collagen at about 5 mg/mL will be then dialyzed against 0.1N acetic acid to remove residual salts (about 5,000 nominal molecular weight cut-off). The retained collagen solution will subsequently be filtered through 0.45 µm and 0.2 µm filters and placed in sterile, 2-liter glass bottles. Collagen concentration will be approximately 5 mg/mL. All steps will be conducted at room temperature. Stock solutions will be stored at 2-8° C.

Process Controls and Quality Control Tests: Final Stock Collagen Will be Examined by the following methods.

Analysis by SDS-PAGE to determine collagen purity;

Analysis of uronic acid to determine amounts of residual glycosaminoglycan

Assay of hydroxyproline to determine total collagen concentration;

Differential Scanning Calorimetry to measure temperature of phase transition (pure, undenatured telopeptide-poor collagen has a transition onset of about 39° C.)

Sterility using USP methods

Endotoxin using LAL methods

Preparation of In Situ Gelling Collagen Solutions.

Purified, pepsin-digested collagen will be precipitated by addition of solid NaCl to 0.8M. The resultant precipitate will be recovered by centrifugation at 3500 RPM, a wet weight determined, and the precipitate placed in dialysis tubing having a NMW cut-off of 50,000 daltons. Attempts will be made to add enough precipitate to produce final collagen solutions at 30 and 50 mg/mL (3 and 5%). The tubing will be placed in 20 volumes of 0.035M EDTA in deionized water, pH 5.0 and dialyzed with agitation for 24 hours. At this point, the dialysis tubing will be transferred to another 20 volumes of 0.035 M EDTA, pH 5.5. Dialysis will be conducted again for 24 hours after which the tubing will be placed in 0.035M EDTA, pH 6.0. This sequence will be continued until dialysis in a final EDTA solution at pH 7.5. This slow increase in pH during EDTA dialysis results in a collagen preparation that remains "soluble" at neutral pH. This is in contrast to standard collagen solutions that spontaneously undergo fibrillogenesis at neutral pH and room temperature. The neutral pH, EDTA-treated collagen solution will remain in solution during storage and will rapidly undergo gelation and fibril formation when exposed to physiological fluids.

Example 6

In Vitro Release of SPICE from Different Collagen Compositions

The release rates of SPICE from collagen plugs produced from collagen prepared as described in Example 5 will be measured daily for a period of 150 days. Five different in-situ gel-forming collagen-matrix preparations will be tested:

Collagen 1: 30 mg/ml (3% w/v) of collagen Type 1

Collagen 2: 50 mg/ml (5% w/v) of collagen Type 1

Collagen 3: 30 mg/ml (3% w/v) of collagen Type 1 mixed with 3 mg/ml of fibrillar collagen Collagen 4: 30 mg/ml (3% w/v) of collagen Type 1 mixed with 6 mg/ml of fibrillar collagen Collagen 5: 50 mg/ml (5% w/v) of collagen Type 1 mixed with 5 mg/ml of fibrillar collagen Each collagen preparation will be mixed with either unmodified SPICE or biotinylated SPICE at a final concentration ranging from 1-10 mg/ml. Plugs will be generated by injecting 0.5 ml of the collagen/protein (3 mg of protein/plug) preparation into the wells of a 24-well plate containing 1 ml of incubation medium. The incubation medium will be either PBS or PBS/50% plasma. The plugs will be incubated at 37° C. with constant agitation. The medium will be replaced every day and the amount of SPICE in the supernatant will be measured.

Levels of SPICE will be measured using standard indirect ELISA for unmodified SPICE and with the EZ Biotin Quantitation Kit (Pierce Biotechnology) for biotinylated SPICE. Antibodies to SPICE suitable for use in the ELISA assay are described in U.S. Pat. No. 6,783,759.

Example 7

Inhibition of CNV by Transscleral Delivery of SPICE

We will test whether SPICE can prevent or inhibit CNV when delivered transsclerally using the collagen formulation. Laser induction of CNV in the Yucatan pig is a well-established model to study exudative ARMD. A laser is used to create ruptures in Bruch's membrane, which trigger neovascularization in the retina surrounding the ruptured membrane over the course of 7 days (>95% reliability). Approximately 50 spots per eye can thus be created and used for analysis. Two eyes in two different pigs are generally accepted as statistically relevant per study group. Three collagen preparations will be chosen for this experiment. Preferred collagen preparations can be selected by measuring the rate of release of SPICE from collagen plugs when such plugs are incubated in vitro in a fluid approximating physiological conditions, e.g., phosphate buffered saline, optionally including 50% plasma by volume, as described in the previous example.

Preparations that provide sustained amounts of SPICE for a reasonable period of time (e.g., at least several days) in reasonable concentrations (e.g., at least in the μg/ml range) are selected. Of course all of the formulations can be tested and an optimum formulation selected based upon the results in vivo. Twenty four (48 eyes) animals will be allotted in 4 groups (12 eyes/group) as follow:
Group 1: Treatment on day 0, Laser induction of CNV on day 14, CNV incidence measurement on day 21
Group 2: Treatment on day 0, Laser induction of CNV on day 30, CNV incidence measurement on day 37
Group 3: Treatment on day 0, Laser induction of CNV on day 60, CNV incidence measurement on day 67
Group 4: Treatment on day 0, Laser induction of CNV on day 90, CNV incidence measurement on day 97
Of the 12 eyes assigned to each group, two eyes will be randomly assigned one of the following treatments:
Treatment 1: Collagen preparation 1. Chosen as one of three optimal formulations as determined by earlier experiments.
Treatment 2: Collagen preparation 2. Chosen as one of three optimal formulations as determined by earlier experiments.
Treatment 3: Collagen preparation 3. Chosen as one of three optimal formulations as determined by earlier experiments.
Treatment 4: Retrobulbar SPICE. In this group, pigs will receive bilateral retrobulbar injections of 3 ml of PBS containing 6 mg of SPICE.
Treatment 5: Intravitreal SPICE. In this group, pigs will receive bilateral intravitreal injections of 500 μl of PBS containing 6 mg of SPICE
Treatment 6: Positive control. In this group, pigs will be left pharmacologically untreated in one eye for the duration of the study and simply receive bilateral retrobulbar injections of 3 ml of PBS. It is a positive control because neovascularization is expected in >95% of cases following laser treatment.

CNV Induction in Pigs.

Ten to twelve weeks old Yucatan pigs (The Jackson Laboratory) will be anesthetized with sodium pentobarbital and the pupils will be dilated with a single drop of 1% tropicamide. Krypton red laser photocoagulation (50 μm spot size, 0.05 s duration, 250 mW) will be used to generate laser spots surrounding the optic nerve by using a handheld coverslip as a contact lens. A bubble should form at the laser spot indicating rupture of Bruch's membrane. Fifty laser spots will be generated in each eye. Therefore, 100 laser spots per treatment condition will be studied (50 spots/eye×2 eyes/condition).

Retrobulbar Injection of Collagen/SPICE.

The animals will be anesthetized with sodium pentobarbital. Using a 30-gauge needle a subconjunctival injection will be made in the superior temporal region of the eye, carefully avoiding extraocular muscles. Three ml of either the collagen/SPICE or PBS/SPICE solution will be injected. Formation of the collagen plug in situ will be evaluated by visual and tactile inspection.

Intravitreal Injection of SPICE in the Eyes of Pigs.

After anesthesia and dilation of the pupil, the anterior chamber will be entered via the limbus with a 28-gauge needle to decompress the eye. Under an operating microscope, which allows visualization of the retina, a 32-gauge (blunt) needle will be passed through a scleral incision, just behind the limbus, into the vitreous cavity. A Hamilton syringe will be used to inject 500 μl of a SPICE solution.

RPE-Choroid-Scleral Flat Mounts Preparation.

Pigs will be anesthetized (Sodium pentobarbital) and perfused through with PBS containing fluorescein-labeled dextran (FITC-Dextran, 2 million average molecular weight, Sigma) prior to sacrifice. The eyes will be removed and fixed for 1 h in 10% phosphate-buffered formalin. The cornea and the lens will be removed and the neurosensory retina will be carefully dissected from the eyecup. Five radial cuts will made from the edge of the eyecup to the equator; the sclera-choroidretinal pigment epithelium (RPE) complex will be flat-mounted, with the sclera facing down, on a glass slide in Aquamount. Flat mounts will be stained with a mAb against elastin (Sigma) and a CY3-conjugated secondary antibody (Sigma) and examined with a confocal microscope (Zeiss LSM510). The CNV will be stained green whereas the elastin in the Bruch's membrane will be stained red. A laser spot with green vessels will be scored CNV-positive, and a laser spot lacking green vessels will be scored CNV-negative.

Determination of Incidence and Size CNV

Seven days after CNV induction, incidence of CNV will be determined. Briefly, the pigs will be perfused with a FITC-dextran (Sigma-Aldrich) solution just prior to sacrifice. After the eyes are excised and fixed in 10% phosphate-buffered formalin, RPE-choroid-scleral flat mounts will be prepared as described above. The flat mounts will be stained with an anti-elastin specific monoclonal antibody (Sigma-Aldrich) and then with a CY3-conjugated secondary antibody (Sigma-Aldrich). Both antibodies will be used at a 1/200 dilution of a 1.0 mg/ml stock solution. Mounts will be observed under confocal microscopy (LSM510, Zeiss). The prominent neovascular growth will stain green whereas the underlying elastin in the Bruch's membrane will stain red within a laser spot.

Interpretation of Results

For determining incidence of CNV, flat mounts will be observed under confocal microscopy (LSM510, Zeiss). Size of the CNV complex (e.g., mean CNV area) will be graded by morphometric image analysis (Axiovision; Zeiss). Differences between groups will optionally be evaluated by ANOVA and/or other suitable statistical methods. A statistically significant difference in the size and/or incidence of CNV complexes, or a trend towards such a difference, in which the treated eyes show a reduction in size and/or incidence relative to untreated eyes, is an indication of effectiveness over the time period tested. For example, a statistically significant difference in the size and/or incidence of CNV complexes, or a trend towards such a difference, in which the treated eyes show a reduction in size and/or incidence relative to untreated eyes, when any of the compositions (treatment 1-5) is administered to Group 4, is an indication that the effect of the composition persists over at least 90 days.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims is introduced into another claim. Any claim that is dependent on another claim can be modified to include one or more limitations, elements, clauses, descriptive terms, etc., found in any other claim that is dependent on the same base claim. Furthermore, where the claims recite a composition, it is to be understood that methods of administering the composition according to any of the methods disclosed herein, and methods of using the composition for any of the purposes disclosed herein are included, and methods of making the composition according to any of the methods of making disclosed herein are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

The inclusion of a "providing" step in certain methods of the invention is intended to indicate that the composition is administered to treat an eye disorder. Thus the subject will have or be at risk of an eye disorder and the composition is administered to treat the disorder, typically upon the sound recommendation of a medical or surgical practitioner, e.g., an ophthalmologist, who may or may not be the same individual who administers the composition. The invention includes embodiments in which a step of providing is not explicitly included and embodiments in which a step of providing is included. The invention also includes embodiments in which a step of identifying the subject as being at risk of or suffering from an eye disorder characterized by macular degeneration, CNV, RNV, ocular inflammation, or any combination of these, is included.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion or specific embodiment is not set forth explicitly herein. Any particular embodiment of the compositions of the invention (e.g., any VCCP or VCIP or fragment or variant of either), any method of administration, any eye disorder or condition or characteristic(s) thereof, or any subject characteristic(s) can be excluded from any one or more claims at the discretion of the inventors.

We claim:

1. A method of treating an eye disorder characterized by macular degeneration, choroidal neovascularization, retinal neovascularization, or ocular inflammation comprising:

administering an effective amount of a viral complement control protein (VCCP) or VCCP variant comprising a sequence at least 90% identical to SEQ ID NO: 2 to a subject in need thereof, wherein the VCCP or VCCP variant is locally administered to the eye or in the vicinity of the eye.

2. The method of claim 1, wherein a VCCP is administered.

3. The method of claim 1, wherein the VCCP is selected from the group consisting of vaccinia complement control protein (VCP), smallpox inhibitor of complement enzymes (SPICE), inflammation modulatory protein (IMP), and monkeypox viral complement control protein (MPVCP).

4. The method of claim 1, wherein the VCCP or VCCP variant is locally administered in an ocular or periocular implant or insert or in a plurality of microparticles or nanoparticles.

5. The method of claim 1, wherein the VCCP or VCCP variant is locally administered in a solution that forms a gel after introduction into the body.

6. The method of claim 1, wherein the VCCP is a poxvirus complement control protein (PVCCP).

7. The method of claim 1, wherein the VCCP is VCP or SPICE.

8. The method of claim 1, wherein the VCCP or VCCP variant is administered by intravitreal injection.

9. A method of inhibiting neovascularization in the eye of a subject in need thereof comprising administering a VCCP or VCCP variant comprising a sequence at least 90% identical to SEQ ID NO: 2 to or in close proximity to the posterior segment of the subject's eye.

10. The method of claim 9, wherein a VCCP is administered.

11. The method of claim 10, wherein the VCCP is selected from the group consisting of VCP, SPICE, IMP, and MPVCP.

12. The method of claim 9, wherein the VCCP or VCCP variant is administered in an ocular or periocular implant or insert or in a plurality of microparticles or nanoparticles.

13. The method of claim 9, wherein the VCCP or VCCP variant is administered in a solution that forms a gel after introduction into the body.

14. The method of claim 9, wherein the subject is suffering from age-related macular degeneration (ARMD).

* * * * *

SEQUENCE LISTING

```
<160> NUMBER OF SEQ ID NOS: 13

<210> SEQ ID NO 1
<211> LENGTH: 263
<212> TYPE: PRT
<213> ORGANISM: Vaccinia virus
<220> FEATURE:
<221> NAME/KEY: MISC_FEATURE
<222> LOCATION: (1)..(263)
<223> OTHER INFORMATION: Complement control protein precursor

<400> SEQUENCE: 1

Met Lys Val Glu Ser Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
            20                  25                  30

Lys Asn Ser Val Glu Thr Asp Ala Asn Ala Asn Tyr Asn Ile Gly Asp
        35                  40                  45

Thr Ile Glu Tyr Leu Cys Leu Pro Gly Tyr Arg Lys Gln Lys Met Gly
    50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly Gln
                85                  90                  95

Leu Asp Ile Gly Gly Val Asp Phe Gly Ser Ser Ile Thr Tyr Ser Cys
            100                 105                 110

Asn Ser Gly Tyr His Leu Ile Gly Glu Ser Lys Ser Tyr Cys Glu Leu
        115                 120                 125
```

```
Gly Ser Thr Gly Ser Met Val Trp Asn Pro Glu Ala Pro Ile Cys Glu
            130                 135                 140

Ser Val Lys Cys Gln Ser Pro Pro Ser Ile Ser Asn Gly Arg His Asn
145                 150                 155                 160

Gly Tyr Glu Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asp Pro Pro Thr Cys Gln Ile Val Lys Cys Pro His
                195                 200                 205

Pro Thr Ile Ser Asn Gly Tyr Leu Ser Ser Gly Phe Lys Arg Ser Tyr
210                 215                 220

Ser Tyr Asn Asp Asn Val Asp Phe Lys Cys Lys Tyr Gly Tyr Lys Leu
225                 230                 235                 240

Ser Gly Ser Ser Ser Ser Thr Cys Ser Pro Gly Asn Thr Trp Lys Pro
                245                 250                 255

Glu Leu Pro Lys Cys Val Arg
            260

<210> SEQ ID NO 2
<211> LENGTH: 244
<212> TYPE: PRT
<213> ORGANISM: Vaccinia virus
<220> FEATURE:
<221> NAME/KEY: MISC_FEATURE
<222> LOCATION: (1)..(244)
<223> OTHER INFORMATION: mature complement control protein

<400> SEQUENCE: 2

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
                20                  25                  30

Tyr Leu Cys Leu Pro Gly Tyr Arg Lys Gln Lys Met Gly Pro Ile Tyr
            35                  40                  45

Ala Lys Cys Thr Gly Thr Gly Trp Thr Leu Phe Asn Gln Cys Ile Lys
50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
            115                 120                 125

Cys Gln Ser Pro Pro Ser Ile Ser Asn Gly Arg His Asn Gly Tyr Glu
130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
```

```
                210                 215                 220
Ser Ser Ser Thr Cys Ser Pro Gly Asn Thr Trp Lys Pro Glu Leu Pro
225                 230                 235                 240

Lys Cys Val Arg

<210> SEQ ID NO 3
<211> LENGTH: 244
<212> TYPE: PRT
<213> ORGANISM: Vaccina virus
<220> FEATURE:
<221> NAME/KEY: MISC_FEATURE
<222> LOCATION: (1)..(244)
<223> OTHER INFORMATION: Copenhagen strain - mature complement control
      protein (VAC-COP C3L)

<400> SEQUENCE: 3

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 4
<211> LENGTH: 244
<212> TYPE: PRT
<213> ORGANISM: Vaccinia virus
<220> FEATURE:
<221> NAME/KEY: MISC_FEATURE
<222> LOCATION: (1)..(244)
<223> OTHER INFORMATION: Western Reserve strain - mature complement
      control protein (VAC-WR C21L)

<400> SEQUENCE: 4
```

-continued

```
Cys Cys Thr Ile Pro Ser Arg Pro Ile Asn Met Lys Phe Lys Asn Ser
1               5                  10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 5
<211> LENGTH: 244
<212> TYPE: PRT
<213> ORGANISM: Cowpox virus
<220> FEATURE:
<221> NAME/KEY: MISC_FEATURE
<222> LOCATION: (1)..(244)
<223> OTHER INFORMATION: Russian isolate from human patient - mature
      complement  control protein (CPV-GRI C17L)

<400> SEQUENCE: 5

Cys Cys Thr Ile Pro Ser Arg Pro Ile Asn Met Lys Phe Lys Asn Ser
1               5                  10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110
```

Gly Ser Met Val Trp Asn Pro Glu Ala Pro Ile Cys Glu Ser Val Lys
            115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 6
<211> LENGTH: 244
<212> TYPE: PRT
<213> ORGANISM: Cowpox virus
<220> FEATURE:
<221> NAME/KEY: MISC_FEATURE
<222> LOCATION: (1)..(244)
<223> OTHER INFORMATION: Brighton strain - mature complement control
      protein (CPV-BRI IMP)

<400> SEQUENCE: 6

Cys Cys Thr Ile Pro Ser Arg Pro Ile Asn Met Lys Phe Lys Asn Ser
1               5                   10                  15

Val Gly Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Lys Cys Pro Ser Pro Arg Asp Ile Asp Asn Gly Gln Ile Asp Ile
65                  70                  75                  80

Gly Gly Val Glu Phe Gly Ser Ser Ile Thr Tyr Ser Cys Asn Ser Gly
                85                  90                  95

Tyr Gln Leu Ile Gly Glu Ser Lys Ser Tyr Cys Glu Leu Gly Tyr Thr
            100                 105                 110

Gly Ser Met Val Trp Asn Pro Glu Ala Pro Ile Cys Glu Ser Val Lys
            115                 120                 125

Cys Pro Ser Pro Pro Ser Val Thr Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Ile Val Cys Ser Gly Gly Glu Trp
                165                 170                 175

Ser Asp Pro Pro Thr Cys Gln Ile Val Lys Cys Pro His Pro Ser Ile
            180                 185                 190

Thr Asn Gly Tyr Leu Ser Ser Gly Phe Lys Arg Ser Tyr Ser His Asn
        195                 200                 205

Asp Asn Val Asp Phe Lys Cys Arg His Gly Tyr Lys Leu Ser Gly Ser

```
              210                 215                 220
Ser Ser Ser Thr Cys Ser Pro Gly Asn Thr Trp Gln Pro Glu Leu Pro
225                 230                 235                 240

Lys Cys Val Arg

<210> SEQ ID NO 7
<211> LENGTH: 244
<212> TYPE: PRT
<213> ORGANISM: Variola virus
<220> FEATURE:
<221> NAME/KEY: MISC_FEATURE
<222> LOCATION: (1)..(244)
<223> OTHER INFORMATION: Bangladesh strain - mature complement control
      protein (VAR-BSH D15L)

<400> SEQUENCE: 7

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
            100                 105                 110

Gly Ser Met Val Trp Asn Pro Lys Ala Pro Ile Cys Glu Ser Val Lys
        115                 120                 125

Cys Gln Leu Pro Pro Ser Ile Ser Asn Gly Arg His Asn Gly Tyr Asn
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro His Pro Thr Ile
            180                 185                 190

Leu Asn Gly Tyr Leu Ser Ser Gly Phe Lys Arg Ser Tyr Ser Tyr Asn
        195                 200                 205

Asp Asn Val Asp Phe Thr Cys Lys Tyr Gly Tyr Lys Leu Ser Gly Ser
    210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 8
<211> LENGTH: 244
<212> TYPE: PRT
<213> ORGANISM: Variola virus
<220> FEATURE:
<221> NAME/KEY: MISC_FEATURE
<222> LOCATION: (1)..(244)
<223> OTHER INFORMATION: India strain - mature complement control
      protein (VAR-IND D12L)

<400> SEQUENCE: 8
```

```
Cys Cys Thr Ile Pro Ser Arg Pro Ile Asn Met Thr Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
            35                  40                  45

Ala Lys Cys Thr Gly Thr Gly Trp Thr Leu Phe Asn Gln Cys Ile Lys
50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
            100                 105                 110

Gly Ser Met Val Trp Asn Pro Lys Ala Pro Ile Cys Glu Ser Val Lys
            115                 120                 125

Cys Gln Leu Pro Pro Ser Ile Ser Asn Gly Arg His Asn Gly Tyr Asn
            130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro His Pro Thr Ile
            180                 185                 190

Leu Asn Gly Tyr Leu Ser Ser Gly Phe Lys Arg Ser Tyr Ser Tyr Asn
            195                 200                 205

Asp Asn Val Asp Phe Thr Cys Lys Tyr Gly Tyr Lys Leu Ser Gly Ser
            210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 9
<211> LENGTH: 244
<212> TYPE: PRT
<213> ORGANISM: Variola virus
<220> FEATURE:
<221> NAME/KEY: MISC_FEATURE
<222> LOCATION: (1)..(244)
<223> OTHER INFORMATION: Alastrim variola minor virus - Garcia strain -
      mature complement control protein (VAR-GAR 18L)

<400> SEQUENCE: 9

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
            35                  40                  45

Ala Lys Cys Thr Gly Thr Gly Trp Thr Leu Phe Asn Gln Cys Ile Lys
50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
            100                 105                 110
```

```
Gly Ser Met Val Trp Asn Pro Lys Ala Pro Ile Cys Glu Ser Val Lys
        115                 120                 125

Cys Gln Leu Pro Pro Ser Ile Ser Asn Gly Arg His Asn Gly Tyr Asn
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro Tyr Pro Thr Ile
            180                 185                 190

Leu Asn Gly Tyr Leu Ser Ser Gly Phe Lys Arg Ser Tyr Ser Tyr Asn
        195                 200                 205

Asp Asn Val Asp Phe Thr Cys Lys Tyr Gly Tyr Lys Leu Ser Gly Ser
210                 215                 220

Ser Ser Thr Cys Ser Pro Gly Asn Thr Trp Gln Pro Glu Leu Pro
225                 230                 235                 240

Lys Cys Val Arg

<210> SEQ ID NO 10
<211> LENGTH: 197
<212> TYPE: PRT
<213> ORGANISM: Mokeypox virus
<220> FEATURE:
<221> NAME/KEY: MISC_FEATURE
<222> LOCATION: (1)..(197)
<223> OTHER INFORMATION: mature complement control protein (MPV-ZAI
      D15L)

<400> SEQUENCE: 10

Tyr Cys Thr Ile Pro Ser Arg Pro Ile Asn Met Lys Phe Lys Asn Ser
1               5                   10                  15

Val Glu Thr Asp Ala Asn Tyr Asn Ile Gly Asp Thr Ile Glu Tyr Leu
            20                  25                  30

Cys Leu Pro Gly Tyr Arg Lys Gln Lys Met Gly Pro Ile Tyr Ala Lys
        35                  40                  45

Cys Thr Gly Thr Gly Trp Thr Leu Phe Asn Gln Cys Ile Lys Arg Arg
    50                  55                  60

Cys Pro Ser Pro Arg Asp Ile Asp Asn Gly Gln Leu Asp Ile Gly Gly
65                  70                  75                  80

Val Asp Phe Gly Ser Ser Ile Thr Tyr Ser Cys Asn Ser Gly Tyr His
                85                  90                  95

Leu Ile Gly Glu Ser Lys Ser Tyr Cys Glu Leu Gly Ser Thr Gly Ser
            100                 105                 110

Met Val Trp Asn Pro Glu Ala Pro Ile Cys Glu Ser Val Lys Cys Gln
        115                 120                 125

Ser Pro Pro Ser Ile Ser Asn Gly Arg His Asn Gly Tyr Glu Asp Phe
    130                 135                 140

Tyr Ile Asp Gly Ser Ile Val Thr Tyr Ser Cys Asn Ser Gly Tyr Ser
145                 150                 155                 160

Leu Ile Gly Asn Ser Gly Val Met Cys Ser Gly Gly Glu Trp Ser Asn
                165                 170                 175

Pro Pro Thr Cys Gln Ile Val Lys Cys Pro His Pro Ile Ser Asn Gly
            180                 185                 190

Lys Leu Leu Ala Ala
        195
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic (sequence used for exemplary purposes
      to define "identity")

<400> SEQUENCE: 11

Ala Lys Leu Ser Ile Gly
1               5

<210> SEQ ID NO 12
<211> LENGTH: 263
<212> TYPE: PRT
<213> ORGANISM: Variola virus
<220> FEATURE:
<221> NAME/KEY: MISC_FEATURE
<222> LOCATION: (1)..(263)
<223> OTHER INFORMATION: SPICE (smallpox inhibitor of complement
      enzymes)

<400> SEQUENCE: 12

Met Lys Val Glu Arg Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
            20                  25                  30

Lys Asn Ser Val Glu Thr Asp Ala Asn Ala Asn Tyr Asn Ile Gly Asp
        35                  40                  45

Thr Ile Glu Tyr Leu Cys Leu Pro Gly Tyr Arg Lys Gln Lys Met Gly
    50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly His
                85                  90                  95

Leu Asp Ile Gly Gly Val Asp Phe Gly Ser Ser Ile Thr Tyr Ser Cys
            100                 105                 110

Asn Ser Gly Tyr Tyr Leu Ile Gly Glu Tyr Lys Ser Tyr Cys Lys Leu
        115                 120                 125

Gly Ser Thr Gly Ser Met Val Trp Asn Pro Lys Ala Pro Ile Cys Glu
    130                 135                 140

Ser Val Lys Cys Gln Leu Pro Pro Ser Ile Ser Asn Gly Arg His Asn
145                 150                 155                 160

Gly Tyr Asn Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asn Pro Pro Thr Cys Gln Ile Val Lys Cys Pro His
        195                 200                 205

Pro Thr Ile Leu Asn Gly Tyr Leu Ser Ser Gly Phe Lys Arg Ser Tyr
    210                 215                 220

Ser Tyr Asn Asp Asn Val Asp Phe Thr Cys Lys Tyr Gly Tyr Lys Leu
225                 230                 235                 240

Ser Gly Ser Ser Ser Ser Thr Cys Ser Pro Gly Asn Thr Trp Gln Pro
                245                 250                 255

Glu Leu Pro Lys Cys Val Arg
            260

<210> SEQ ID NO 13
<211> LENGTH: 690
```

```
<212> TYPE: PRT
<213> ORGANISM: Homo sapiens
<220> FEATURE:
<221> NAME/KEY: MISC_FEATURE
<222> LOCATION: (1)..(690)
<223> OTHER INFORMATION: b2-GPI (apolipoprotein H, or apoH)

<400> SEQUENCE: 13

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys Met Ile Ser Pro Val Leu Ile
            340                 345                 350

Leu Phe Ser Ser Phe Leu Cys His Val Ala Ile Ala Gly Arg Thr Cys
        355                 360                 365

Pro Lys Pro Asp Asp Leu Pro Phe Ser Thr Val Val Pro Leu Lys Thr
370                 375                 380
```

```
Phe Tyr Glu Pro Gly Glu Ile Thr Tyr Ser Cys Lys Pro Gly Tyr
385                 390                 395                 400

Val Ser Arg Gly Gly Met Arg Lys Phe Ile Cys Pro Leu Thr Gly Leu
            405                 410                 415

Trp Pro Ile Asn Thr Leu Lys Cys Thr Pro Arg Val Cys Pro Phe Ala
            420                 425                 430

Gly Ile Leu Glu Asn Gly Ala Val Arg Tyr Thr Thr Phe Glu Tyr Pro
            435                 440                 445

Asn Thr Ile Ser Phe Ser Cys Asn Thr Gly Phe Tyr Leu Asn Gly Ala
            450                 455                 460

Asp Ser Ala Lys Cys Thr Glu Glu Gly Lys Trp Ser Pro Glu Leu Pro
465                 470                 475                 480

Val Cys Ala Pro Ile Ile Cys Pro Pro Ser Ile Pro Thr Phe Ala
            485                 490                 495

Thr Leu Arg Val Tyr Lys Pro Ser Ala Gly Asn Asn Ser Leu Tyr Arg
                500                 505                 510

Asp Thr Ala Val Phe Glu Cys Leu Pro Gln His Ala Met Phe Gly Asn
            515                 520                 525

Asp Thr Ile Thr Cys Thr Thr His Gly Asn Trp Thr Lys Leu Pro Glu
            530                 535                 540

Cys Arg Glu Val Lys Cys Pro Phe Pro Ser Arg Pro Asp Asn Gly Phe
545                 550                 555                 560

Val Asn Tyr Pro Ala Lys Pro Thr Leu Tyr Tyr Lys Asp Lys Ala Thr
                565                 570                 575

Phe Gly Cys His Asp Gly Tyr Ser Leu Asp Gly Pro Glu Glu Ile Glu
            580                 585                 590

Cys Thr Lys Leu Gly Asn Trp Ser Ala Met Pro Ser Cys Lys Ala Ser
            595                 600                 605

Cys Lys Val Pro Val Lys Lys Ala Thr Val Val Tyr Gln Gly Glu Arg
            610                 615                 620

Val Lys Ile Gln Glu Lys Phe Lys Asn Gly Met Leu His Gly Asp Lys
625                 630                 635                 640

Val Ser Phe Phe Cys Lys Asn Lys Glu Lys Lys Cys Ser Tyr Thr Glu
                645                 650                 655

Asp Ala Gln Cys Ile Asp Gly Thr Ile Glu Val Pro Lys Cys Phe Lys
            660                 665                 670

Glu His Ser Ser Leu Ala Phe Trp Lys Thr Asp Ala Ser Asp Val Lys
            675                 680                 685

Pro Cys
690
```